United States Patent
Jeon et al.

(10) Patent No.: US 9,024,304 B2
(45) Date of Patent: May 5, 2015

(54) NAPHTHALENE DERIVATIVE, ORGANIC MATERIAL INCLUDING THE SAME, AND ORGANIC ELECTROLUMINESCENT DEVICE INCLUDING THE SAME

(75) Inventors: Young Min Jeon, Ansan-si (KR); Chang Hyung Lee, Gyeongsangnam-do (KR); Jeong Gyu Park, Siheung-si (KR); Sang Jin Nam, Anyang-si (KR); Hyo Jin Min, Anyang-si (KR); Joon Woo Kim, Siheung-si (KR); Il Ji Lim, Seoul (KR)

(73) Assignee: Dae Joo Electronic Materials Co., Ltd., Gyeonggi-do (KR)

( * ) Notice: Subject to any disclaimer, the term of this patent is extended or adjusted under 35 U.S.C. 154(b) by 0 days.

(21) Appl. No.: 14/008,576

(22) PCT Filed: Mar. 29, 2012

(86) PCT No.: PCT/KR2012/002322
§ 371 (c)(1),
(2), (4) Date: Oct. 30, 2013

(87) PCT Pub. No.: WO2012/134191
PCT Pub. Date: Oct. 4, 2012

(65) Prior Publication Data
US 2014/0299849 A1    Oct. 9, 2014

(30) Foreign Application Priority Data

Mar. 29, 2011 (KR) .......................... 10-2011-0027969
Mar. 29, 2011 (KR) .......................... 10-2011-0027970

(51) Int. Cl.
*H01L 51/00* (2006.01)
*H01L 51/50* (2006.01)
(Continued)

(52) U.S. Cl.
CPC ........ *H01L 51/5056* (2013.01); *H01L 51/0052* (2013.01); *H01L 51/0054* (2013.01);
(Continued)

(58) Field of Classification Search
USPC .......................................................... 585/27
See application file for complete search history.

(56) References Cited

U.S. PATENT DOCUMENTS

| 2005/0175857 A1 | 8/2005 | Coggan et al. |
| 2006/0093857 A1 | 5/2006 | Nakashima et al. |

(Continued)

FOREIGN PATENT DOCUMENTS

| JP | 08-012600 | 1/1996 |
| JP | 2000-273056 | 10/2000 |

(Continued)

OTHER PUBLICATIONS

Derwent Abstract for JP 2009-212201 A, Iwawaki et al., published Sep. 17, 2009.*

(Continued)

*Primary Examiner* — Stephen W Smoot

(57) ABSTRACT

The present invention provides a compound represented by the following formula 1. The compound of the present invention has high luminance, high luminous efficiency, excellent color purity and excellent high-temperature stability, and thus can provide a material for an organic electroluminescent device and an organic electroluminescent device having a long lifetime.

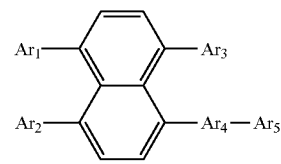

Formula 1

18 Claims, 9 Drawing Sheets

Molecular Formula=$C_{40}H_{26}$
Formula=506.63444

Molecular Formula=$C_{40}H_{26}$
Formula=506.63444

(51) Int. Cl.
*C07C 15/28* (2006.01)
*C09K 11/06* (2006.01)
*H05B 33/10* (2006.01)

(52) U.S. Cl.
CPC ........ *H01L51/0058* (2013.01); *H01L 51/5012* (2013.01); *C07C 15/28* (2013.01); *C09K 11/06* (2013.01); *H05B 33/10* (2013.01); *C09K 2211/1007* (2013.01); *C09K 2211/1011* (2013.01); *C07C 2103/24* (2013.01); *H01L 51/5072* (2013.01); *H01L 51/5088* (2013.01); *H01L 51/5092* (2013.01)

(56) References Cited

U.S. PATENT DOCUMENTS

| | | | | |
|---|---|---|---|---|
| 2008/0210930 | A1* | 9/2008 | Kamatani et al. | 257/40 |
| 2008/0224603 | A1 | 9/2008 | Hashimoto et al. | |
| 2009/0160327 | A1 | 6/2009 | Oda et al. | |
| 2011/0227057 | A1* | 9/2011 | Kosuge et al. | 257/40 |
| 2012/0319090 | A1* | 12/2012 | Shinkai et al. | 257/40 |
| 2013/0221332 | A1* | 8/2013 | Xia et al. | 257/40 |

FOREIGN PATENT DOCUMENTS

| | | |
|---|---|---|
| JP | 2005-222948 | 8/2005 |
| JP | 2006-151966 | 6/2006 |
| JP | 2007-084485 | 4/2007 |
| JP | 2008-255099 | 10/2008 |
| JP | 2009-158582 | 7/2009 |
| JP | 2009-212201 | 9/2009 |
| JP | 2010-087488 | 4/2010 |

OTHER PUBLICATIONS

Tang et al. "Organic Electroluminescent Diodes", Applied Physics Letters, 51(12): 913-915, Sep. 21, 1987.

Notification of Office Action Dated Jun. 16, 2014 From the State Intellectual Property Office of the People's Republic of China Re. Application No. 2012/80020856.4 and Its Translation Into English.

Ibuki et al. "Preparation and Conformational Properties of Several 1,8-Diarylnaphthalenes", Bulletin of the Chemical Society of Japan, 55: 845-851, Mar. 1982.

Iyoda et al. "A Cyclic Oligophenylene Containing Two 1,8-Naphthalene Units Bridged by Two Face-to-Face Biphenyl Linkages Exhibiting Unusual Strain and Pi-Pi Interaction", Organic Letters, 2(14): 2081-2083, Published on Web Jun. 9, 2000.

Lima et al. "Exploring the Selectivity of the Suzuki-Miyaura Cross-Coupling Reaction in the Synthesis of Arylnaphthalenes", Tetrahedron, 67: 689-697, Available Online Dec. 1, 2010.

* cited by examiner

Molecular Formula=$C_{40}H_{26}$
Formula=506.63444

Molecular Formula=$C_{40}H_{26}$
Formula=506.63444

NAPHTHALENE DERIVATIVE, ORGANIC MATERIAL INCLUDING THE SAME, AND ORGANIC ELECTROLUMINESCENT DEVICE INCLUDING THE SAME

RELATED APPLICATIONS

This application is a National Phase of PCT Patent Application No. PCT/KR2012/002322 having International filing date of Mar. 29, 2012, which claims the benefit of priority of Korean Patent Application Nos. 10 2011 0027970 filed on Mar. 29, 2011 and 10-2011-0027969 filed on Mar. 29, 2011. The contents of the above applications are all incorporated by reference as if fully set forth herein in their entirety.

FIELD AND BACKGROUND OF THE INVENTION

The present invention relates to the display field, and more particularly to a naphthalene derivative that can be used in the preparation of an organic electroluminescent device that is a kind of display, a material for an organic electroluminescent device, which includes the same, and an organic electroluminescent device including the same.

Organic semiconductors have been developed for application to various kinds of many electronic systems. Organic electroluminescent devices have a simple structure, various advantages in their preparation process, high luminance, excellent viewing angle characteristics, fast response speeds, and low driving voltages, compared to other flat panel display devices such as liquid crystal displays (LCDs), plasma display panels (PDPs) and field emission displays (FEDs). By virtue of these advantages, organic electroluminescent devices have been actively developed for use as light sources for backlight units for displays or flat panel displays such as wall-mounted televisions, lighting devices, advertizing boards and the like.

Generally, when voltage is applied to an organic electroluminescent device, a hole injected from the anode and an electron injected from the cathode are recombined to form an exciton that is an electron-hole pair, and the energy of the exciton is transferred to the light-emitting material and converted into light.

Since a low-voltage driving organic electroluminescent device including an organic thin film laminated between two opposite electrodes in order to increase the efficiency and stability of the organic electroluminescent device was reported by C. W. Tang et al. of Eastman Kodak Company (C. W. Tang, S. A. Vanslyke, Applied Physics Letters, Vol. 51, pp. 913, 1987), studies on organic materials for organic electroluminescent device having a multilayered thin film structure have been actively conducted. Further, Japanese Patent Laid-Open Publication No. 1996-012600 discloses a device including a phenyl anthracene derivative as a light-emitting material. This anthracene derivative is used as a blue light-emitting material, but more highly efficient light emission has been required.

Meanwhile, the stability of thin films has been required to increase the lifetime of devices, and improvement in conventional anthracene derivatives has been required, because these derivatives are frequently crystallized so that thin films including these derivatives are broken. For example, U.S. Pat. No. 0,593,571 discloses a dinaphthyl anthracene compound. However, because this compound has a horizontally and vertically symmetrical molecular structure, it is easily aligned and crystallized during high-temperature storage and high-temperature driving. In addition, Japanese Patent Laid-Open Publication No. 2000-273056 discloses a horizontally asymmetrical allyl anthracene compound, but this compound cannot be prevented from being crystallized, because a group that is substituted with anthracenediyl is a simple phenyl or biphenyl group.

Accordingly, the present inventors have conducted studies on aromatic compounds capable of achieving a low driving voltage, excellent color purity, high luminous efficiency, high heat resistance and a long lifetime, and as a result, have found that a 1,8-substituted naphthalene derivative has such characteristics, thereby completing the present invention.

SUMMARY OF THE INVENTION

It is an object of the present invention to provide an aromatic compound capable of achieving a low driving voltage, excellent color purity, high luminous efficiency, high heat resistance and a long lifetime, a material for an organic electroluminescent device, which includes the same, and an organic electroluminescent device including the same.

To achieve the above object, the present invention provides a compound represented by the following formula 1:

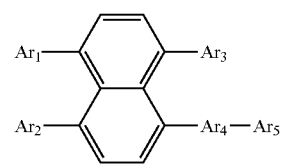

[Formula 1]

wherein $Ar_1$ is hydrogen or a $C_{6-10}$ monovalent aromatic group, wherein the $C_{6-10}$ monovalent aromatic group is unsubstituted or substituted with phenyl or naphthyl, $Ar_2$ is hydrogen or a $C_{6-10}$ monovalent aromatic group, wherein the $C_{6-10}$ monovalent aromatic group is unsubstituted or substituted with phenyl or naphthyl, $Ar_3$ is hydrogen or a $C_{6-10}$ monovalent aromatic group, wherein the $C_{6-10}$ monovalent aromatic group is unsubstituted or substituted with phenyl or naphthyl, $Ar_4$ is a $C_{6-16}$ divalent aromatic group, wherein the $C_{6-16}$ divalent aromatic group is unsubstituted or substituted with phenyl, and $Ar_5$ is a $C_{6-14}$ monovalent aromatic group, wherein the $C_{6-14}$ monovalent aromatic group is unsubstituted or substituted with naphthyl, phenyl, naphthyl-substituted phenyl, or biphenyl, with the proviso that when $Ar_3$ is a $C_{6-10}$ monovalent aromatic group, $Ar_1$ and $Ar_2$ are each hydrogen, and when $Ar_3$ is hydrogen, $Ar_1$ and $Ar_2$ are each a $C_{6-10}$ monovalent aromatic group.

The compound of formula 1 is characterized in that it has substituents at the 1,8-positions of naphthalene and in that the chemical structure thereof is significantly distorted by a steric effect because the distance between the substituents is close. As shown in FIGS. 1 and 2, two kinds of compounds have the same molecular formula, but the three-dimensional steric structure of 1,8-substituted naphthalene is significantly distorted compared to that of 1,4-substituted naphthalene. Due to the distorted steric structure, the intermolecular spatial distance can be increased, and when this compound is applied to an organic electroluminescent device, the device can have excellent color purity and a long lifetime.

Preferably, in formula 1 $Ar_1$ and $Ar_2$ are each hydrogen, $Ar_3$ is phenyl; or naphthyl unsubstituted or substituted with phenyl or naphthyl, $Ar_4$ is naphthylene; phenylene; pyrenylene;

phenanthryiene; or anthracenylene unsubstituted or substituted with phenyl, and Ar$_5$ is naphthyl; biphenyl; phenyl unsubstituted or substituted with naphthyl; or anthracenyl unsubstituted or substituted with naphthyl, phenyl, naphthyl-substituted phenyl, or biphenyl.

Preferably, Ar$_1$ and Ar$_2$ are each hydrogen, Ar$_3$ is naphthyl unsubstituted or substituted with phenyl or naphthyl, Ar$_4$ is naphthylene or anthracenylene, and Ar$_5$ is naphthyl; phenyl; or anthracenyl substituted with naphthyl or phenyl.

Preferably, Ar$_1$ and Ar$_2$ are each hydrogen, Ar$_3$ is phenyl, Ar$_4$ is phenylene, and Ar$_5$ is naphthyl; phenyl; phenyl substituted with naphthyl; or anthracenyl substituted with phenyl.

Preferably, Ar$_1$ and Ar$_2$ are each hydrogen, Ar$_3$ is phenyl, Ar$_4$ is pyrenyl; or henanthrylene, and Ar$_5$ is naphthyl; biphenyl; or phenyl unsubstituted or substituted with naphthyl.

Preferably, Ar$_1$ and Ar$_2$ are each hydrogen, Ar$_3$ is phenyl or naphthyl, Ar$_4$ is anthracenylene unsubstituted or substituted with phenyl, and Ar$_5$ is naphthyl; biphenyl; or phenyl unsubstituted or substituted with naphthyl.

Preferably, Ar$_1$ and Ar$_2$ are each hydrogen, and Ar$_3$ is phenyl; 1-naphthyl; 2-naphthyl; 6-phenyl-2-naphthyl; or 6-(1-naphthyl)-2-naphthyl.

Preferably, Ar$_1$ is phenyl; or naphthyl unsubstituted or substituted with phenyl or naphthyl, Ar$_2$ is phenyl; or naphthyl unsubstituted or substituted with phenyl or naphthyl, Ar$_3$ is hydrogen, Ar$_4$ is naphthylene; phenylene; pyrenylene; phenanthrylene; or anthracenylene unsubstituted or substituted with phenyl, and Ar$_5$ is naphthyl; biphenyl; phenyl unsubstituted or substituted with naphthyl; or anthracen unsubstituted or substituted with naphthyl, phenyl, naphthyl-substituted or biphenyl.

Preferably, Ar$_1$ is naphthyl unsubstituted or substituted with phenyl or naphthyl, Ar$_2$ is naphthyl unsubstituted or substituted with phenyl or naphthyl, Ar$_3$ is hydrogen, Ar$_4$ is naphthylene or anthracenylene, and Ar$_5$ is naphthyl; phenyl; or anthracenyl substituted with naphthyl or phenyl.

Preferably, Ar$_1$ is phenyl, Ar$_2$ is phenyl, Ar$_3$ is hydrogen, Ar$_4$ is phenylene, and Ar$_5$ is naphthyl; phenyl; phenyl substituted with naphthyl; or anthracenyl substituted with biphenyl.

Preferably, Ar$_1$ is phenyl, Ar$_2$ is phenyl, Ar$_3$ is hydrogen, Ar$_4$ is pyrenyl or phenanthrylene, and Ar$_5$ is naphthyl; biphenyl; or phenyl unsubstituted or substituted with naphthyl.

Preferably, Ar$_1$ is phenyl or naphthyl, Ar$_2$ is phenyl or naphthyl, Ar$_3$ is hydrogen, Ar$_4$ is anthracenylene unsubstituted or substituted with phenyl, and Ar$_5$ is naphthyl; biphenyl; or phenyl unsubstituted or substituted with naphthyl.

Preferably, Ar$_1$ and Ar$_2$ are each phenyl; 1-naphthyl; 2-naphthyl; 6-phenyl-2-naphthyl; or 6-(1-naphthyl)-2-naphthyl, and Ar$_3$ is hydrogen.

Preferably, Ar$_1$ and Ar$_2$ are phenyl, and Ar$_3$ is hydrogen.

Preferably, Ar$_4$ is 1,4-naphthylene; 2,6-naphthylene; 1,4-pentylene; 1,6-pyrenylene; 2,7-phenanthrylene; 9,10-anthracenylene; or 9-phenyl-2,10-anthracenylene.

Preferably, Ar$_5$ is 1-naphthyl; 2-naphthyl; biphenyl-4-yl; phenyl; 4-(1-naphthyl)-phenyl; 4-(2-naphthyl)-phenyl; 10-(1-naphthyl)-9-anthracenyl; 10-(2-naphthyl)-9-anthracenyl; 10-phenyl-9-anthracenyl; 10-(4-(1-naphthyl)phenyl)-9-anthracenyl; 10-(4-(2-naphthyl)phenyl)-9-anthracenyl; or 10-(biphenyl-4-yl)-9-anthracenyl.

Examples of the compound represented by formula 1 are as follows:

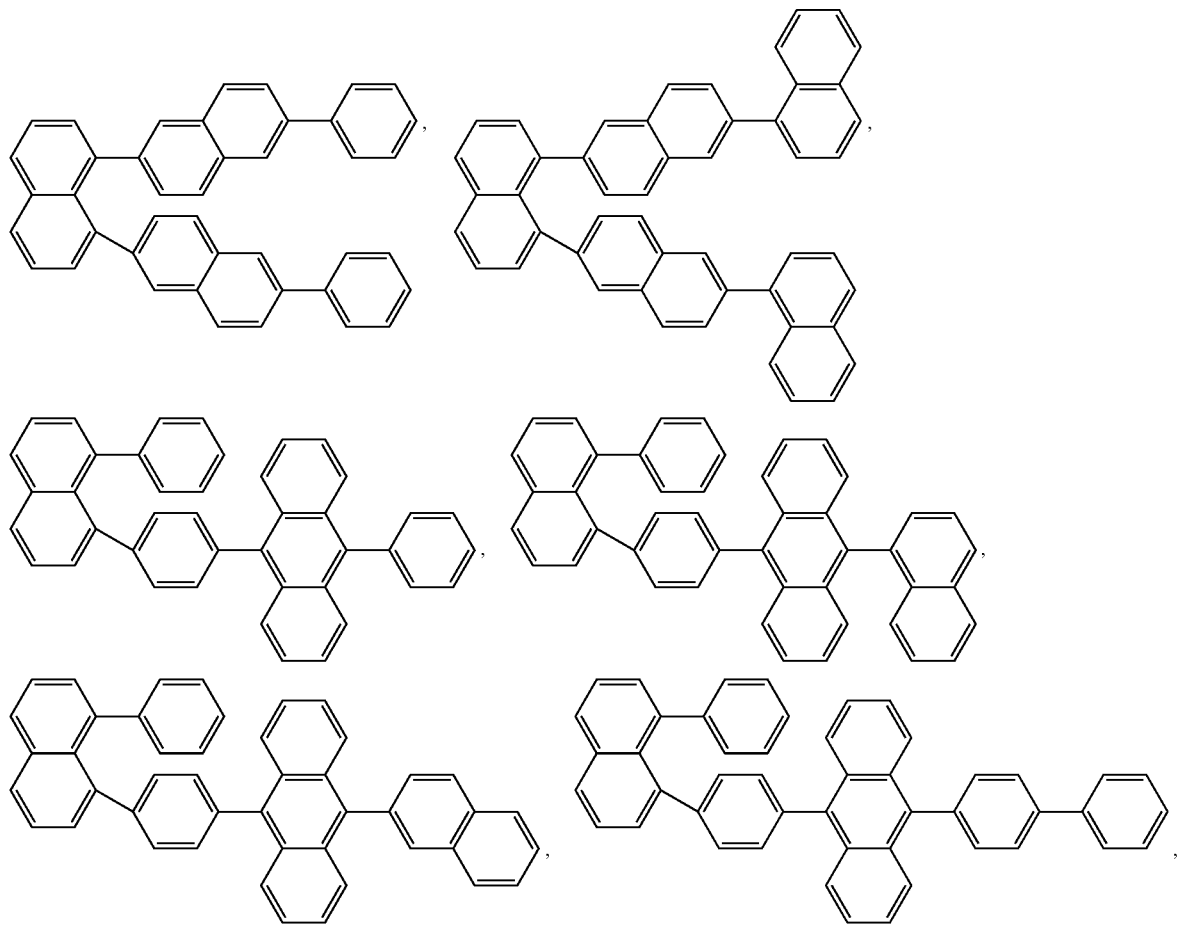

-continued
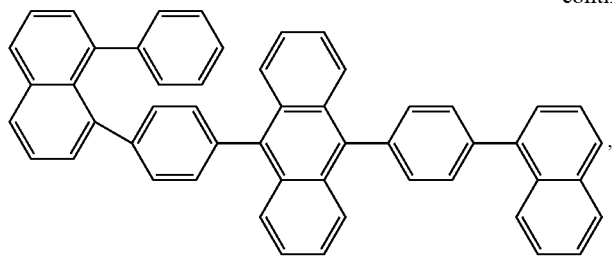
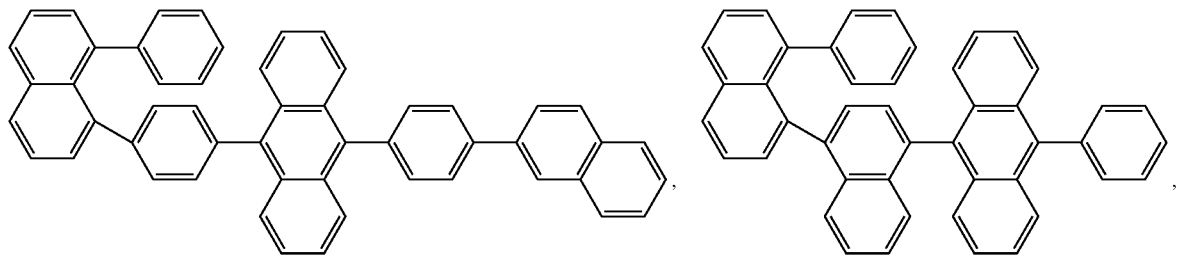
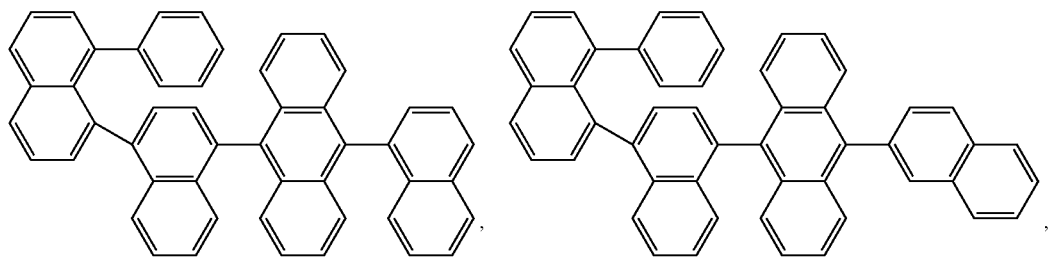
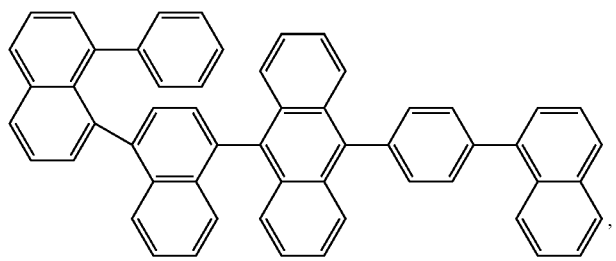
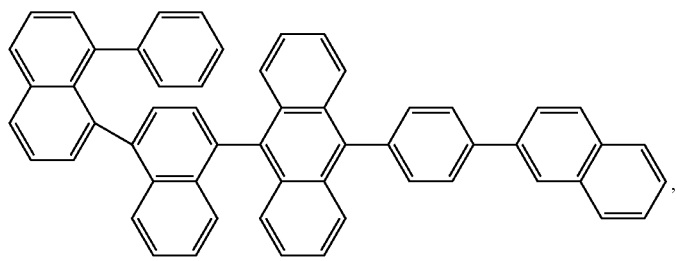
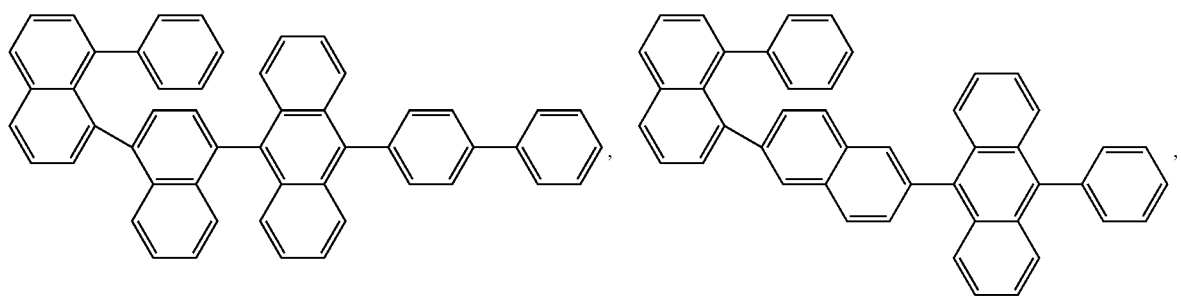

-continued
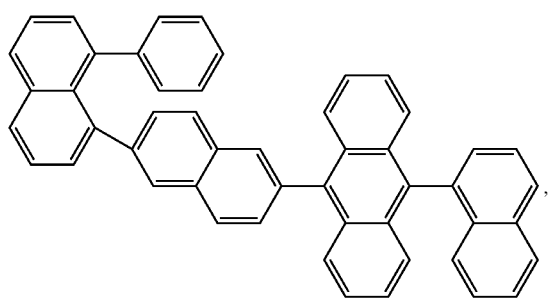
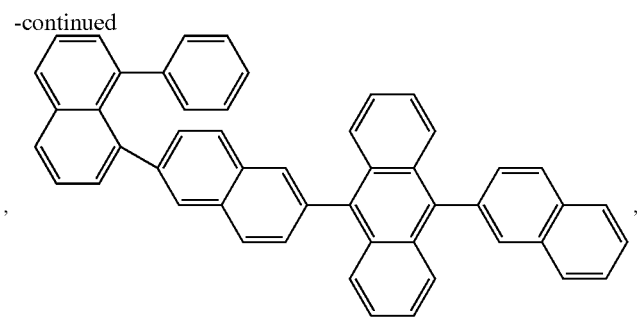
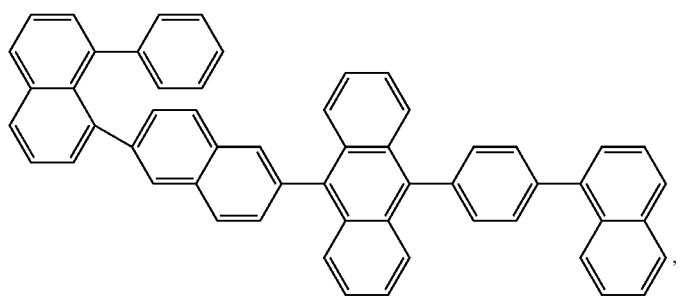
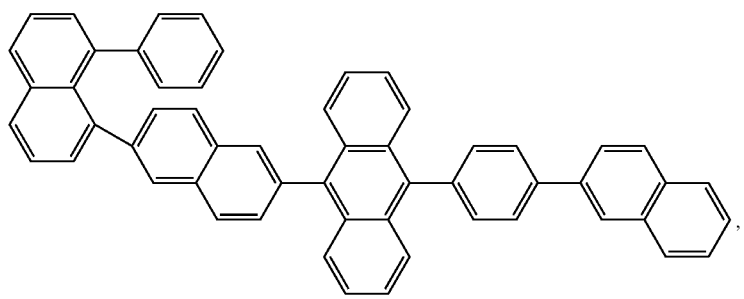
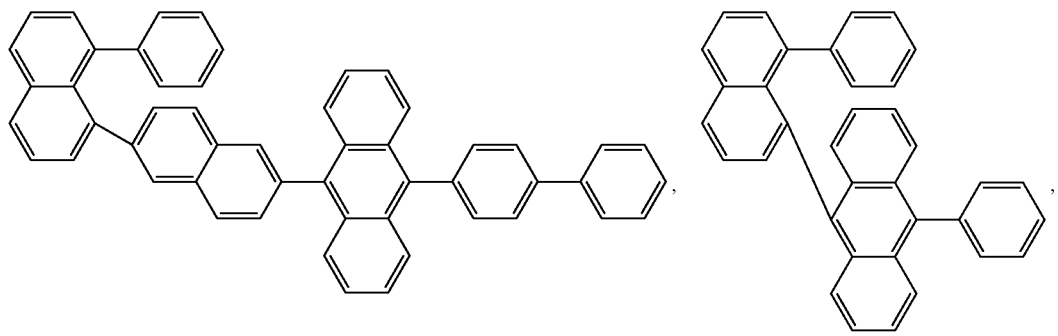
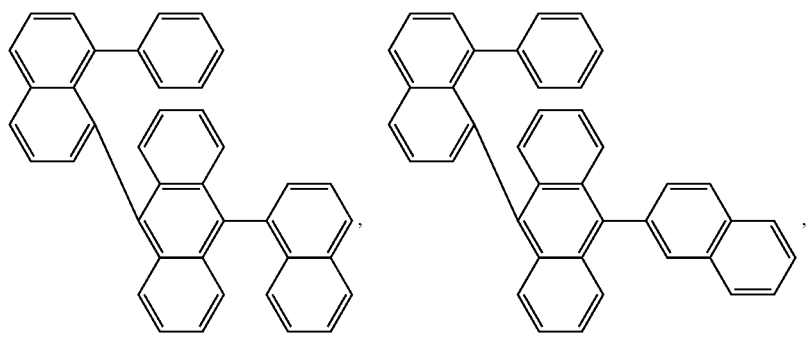

-continued
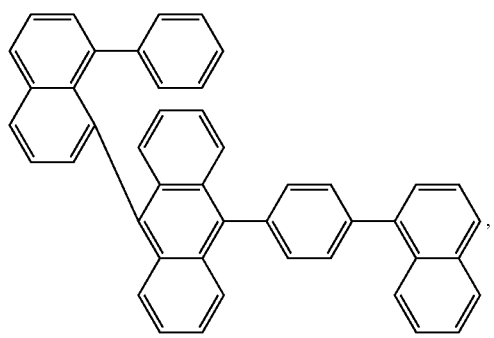
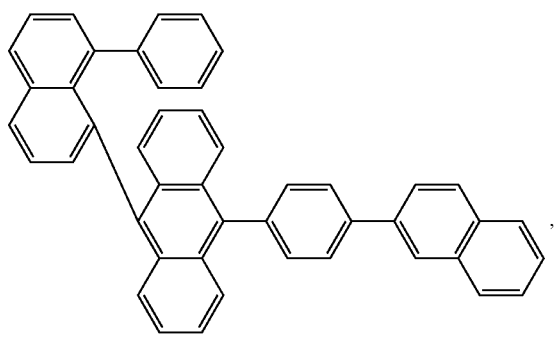
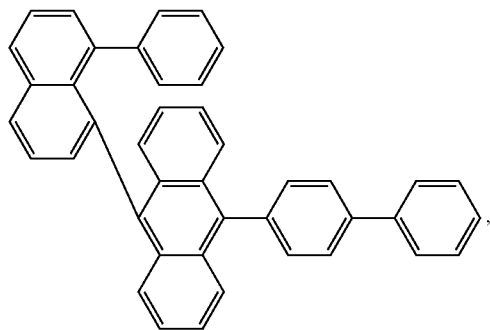
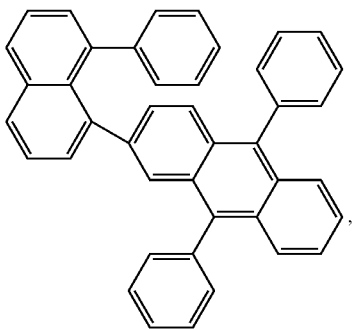
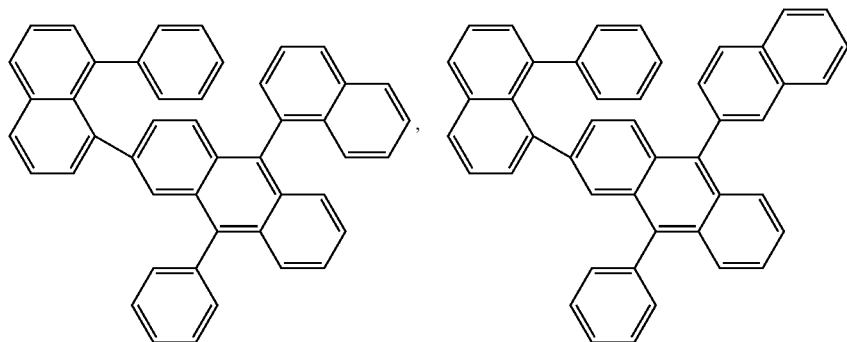
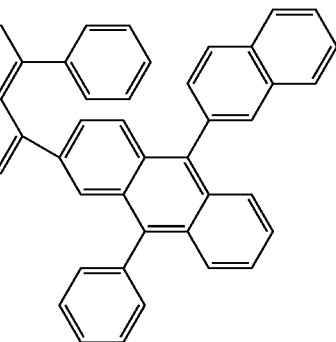
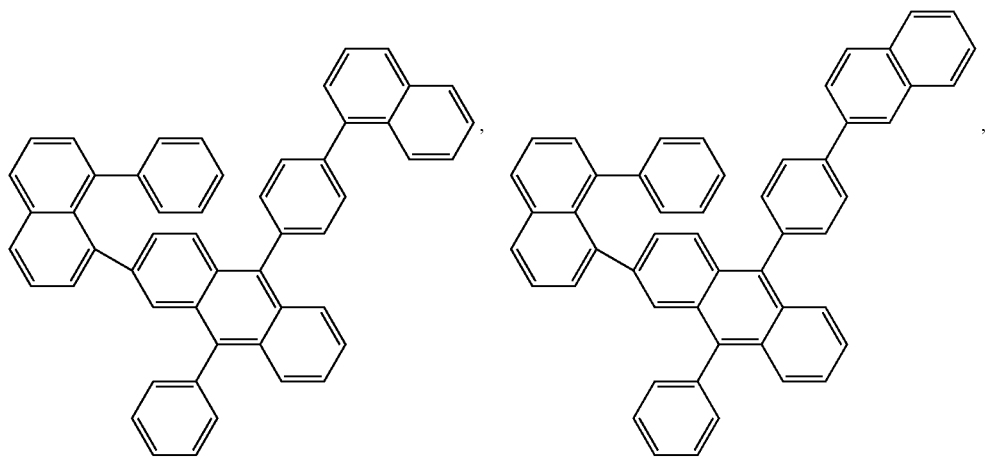
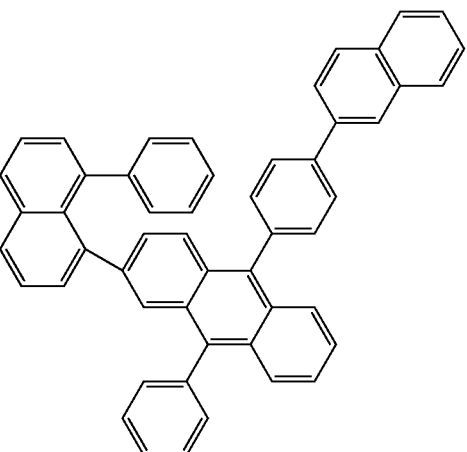

-continued
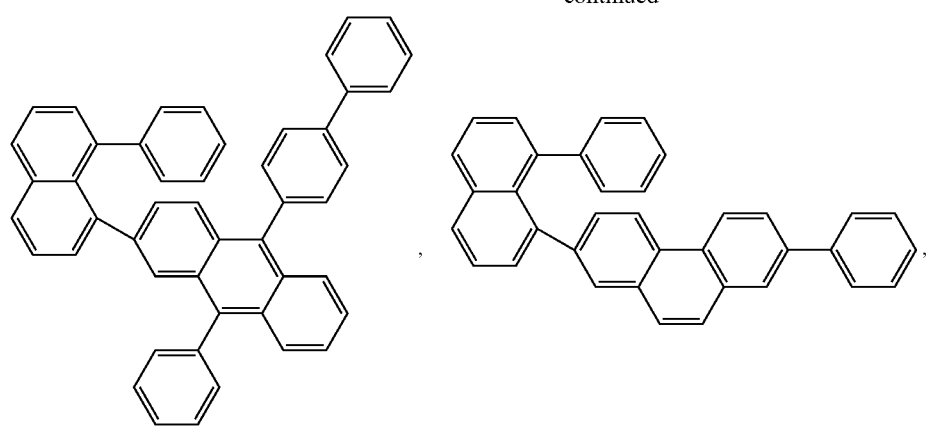
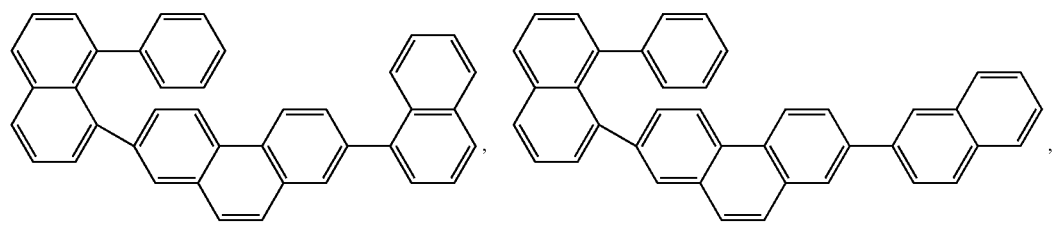
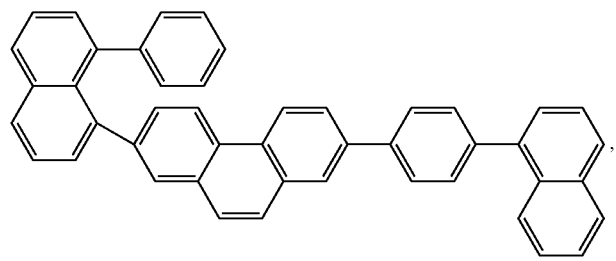
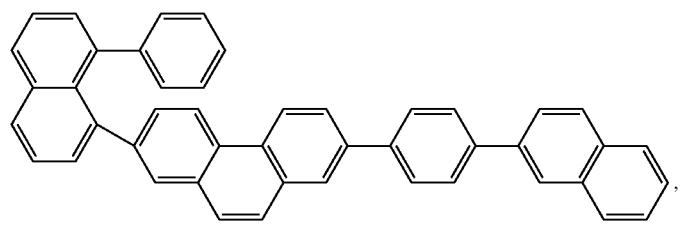
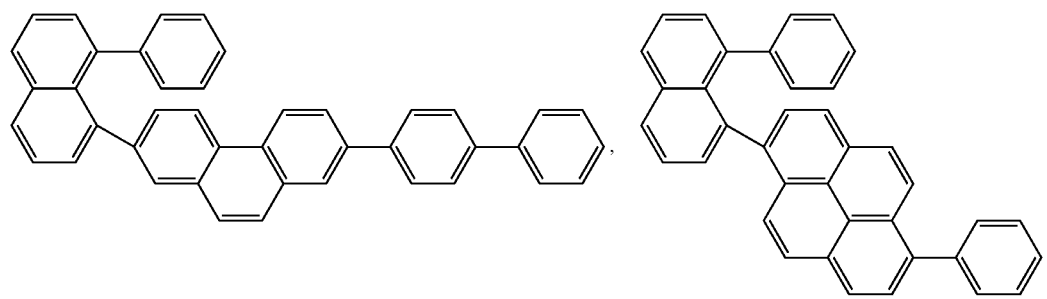

-continued
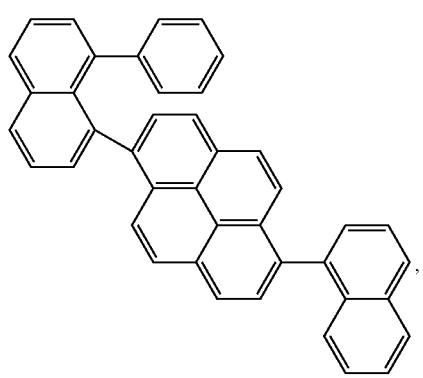
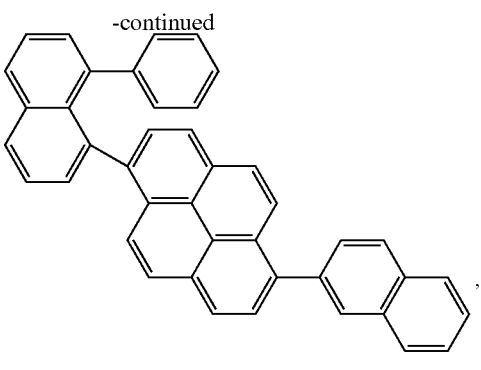
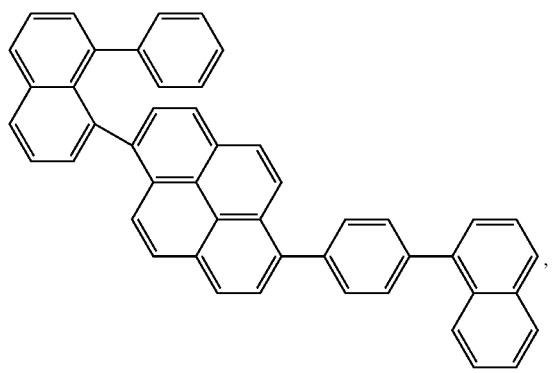
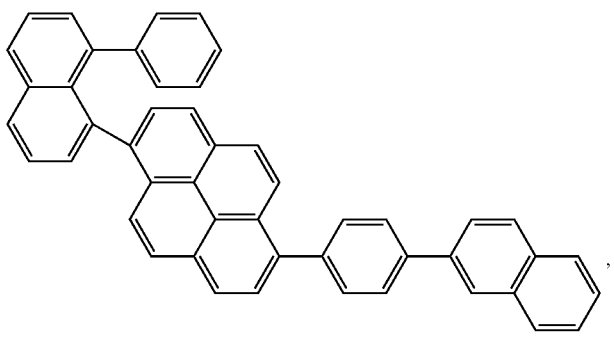
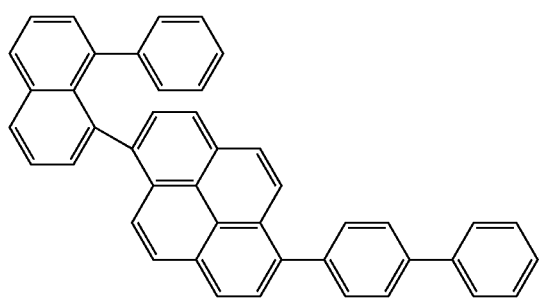
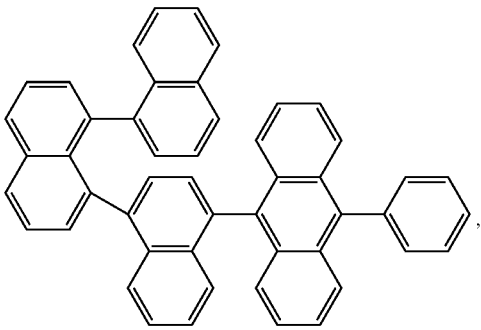
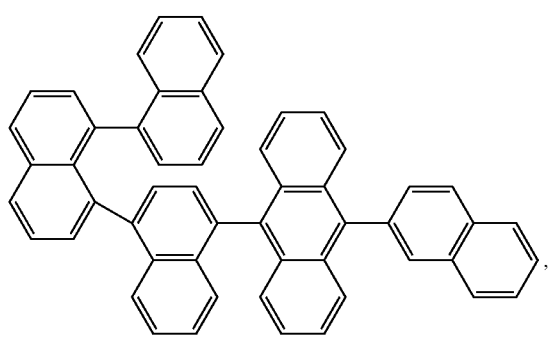
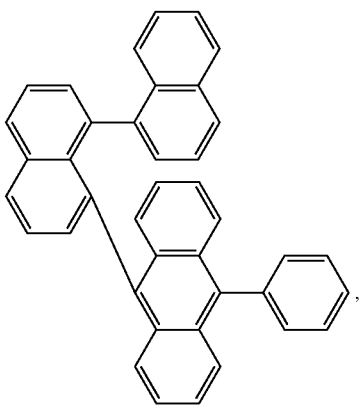

-continued
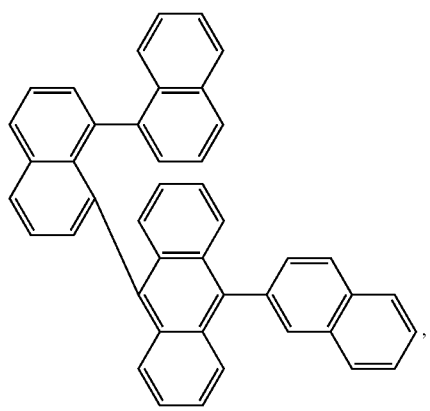
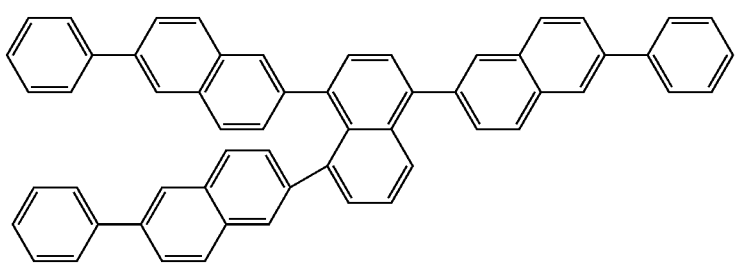
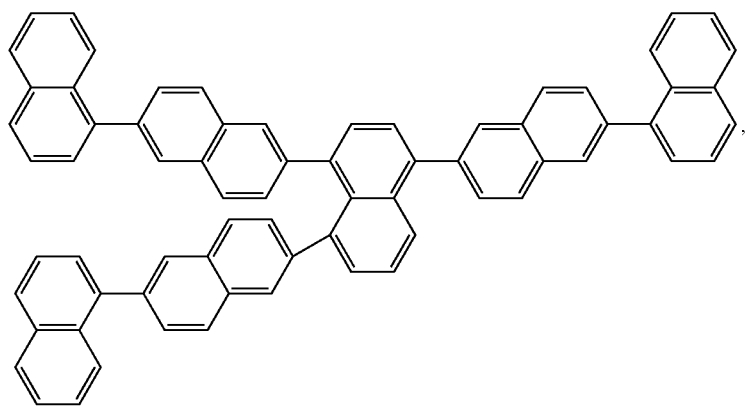
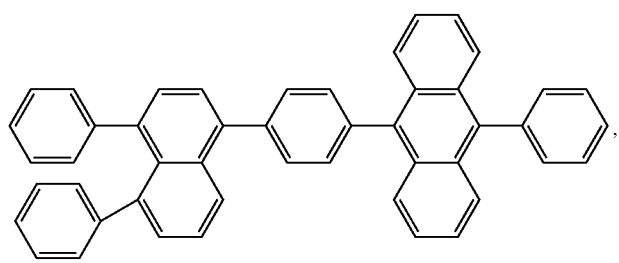
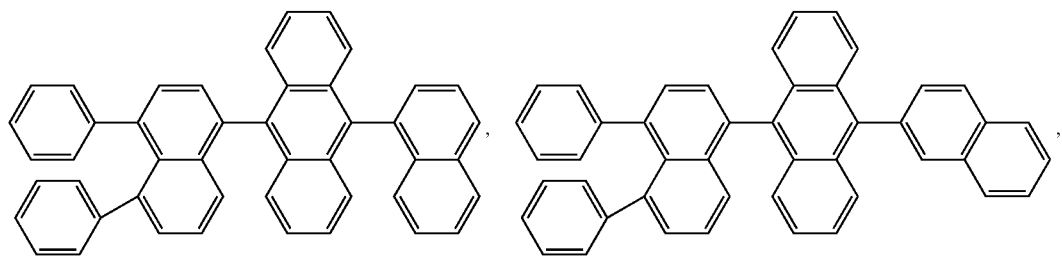
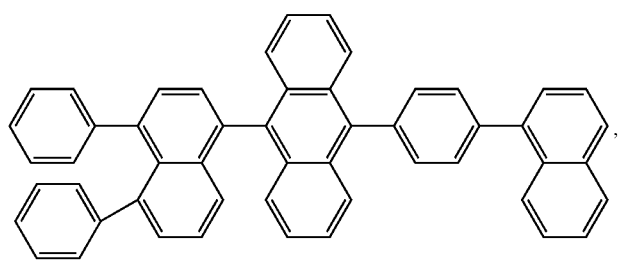

-continued
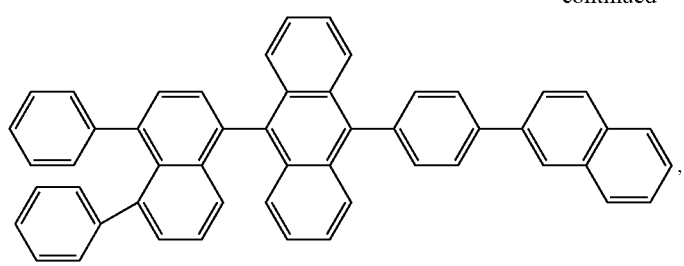
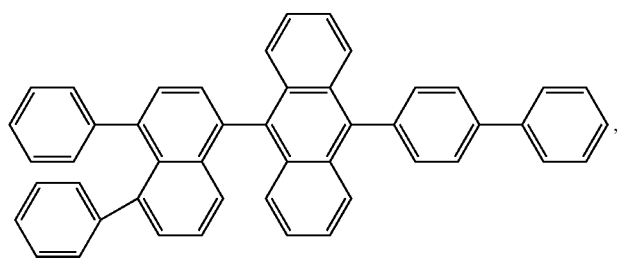
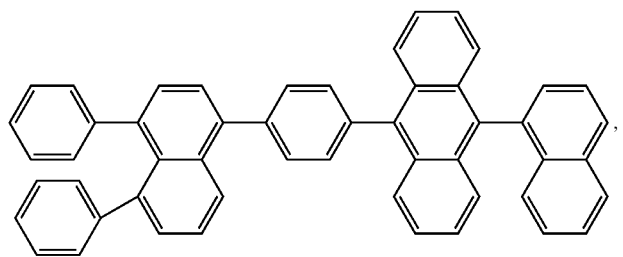
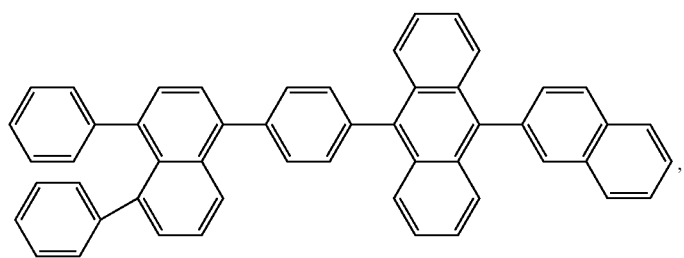
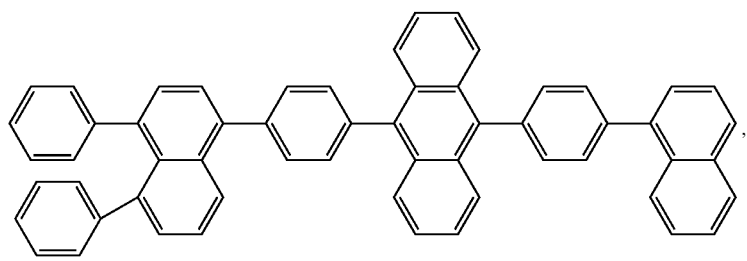
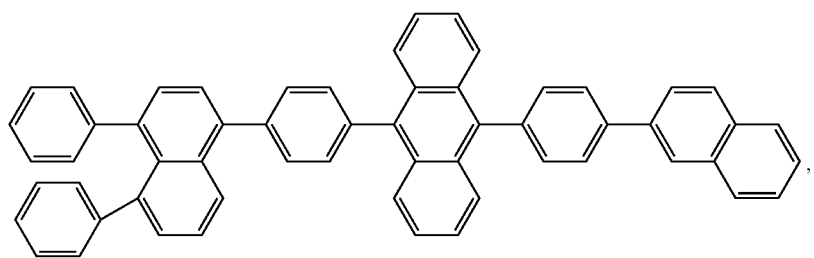

-continued
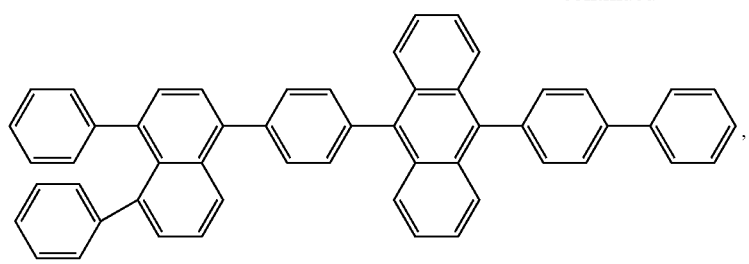
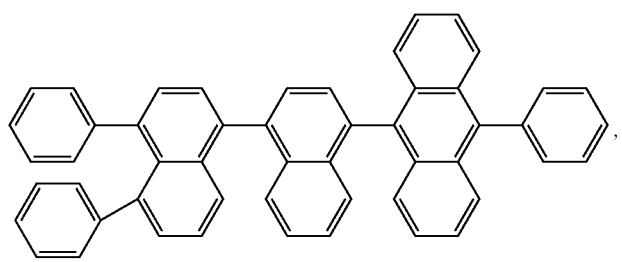
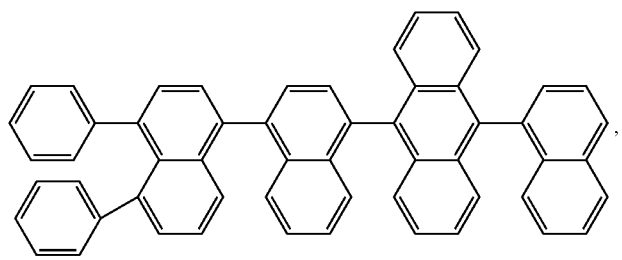
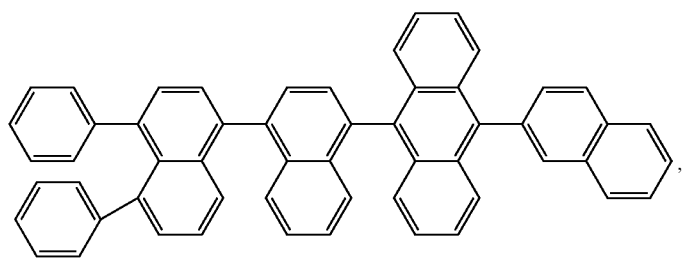
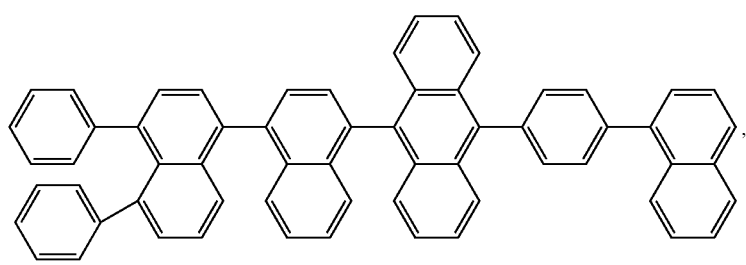
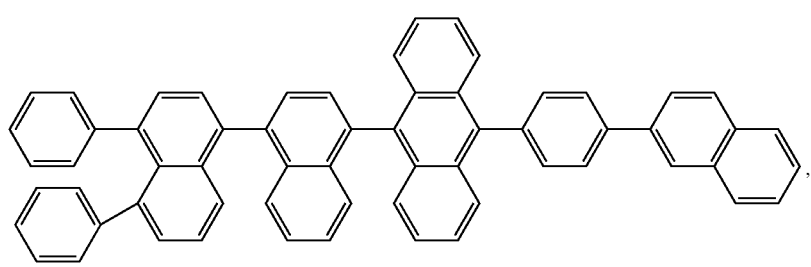

-continued
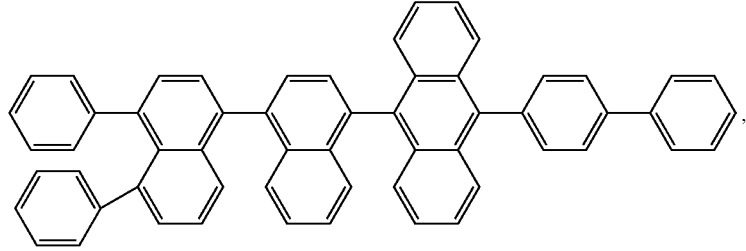
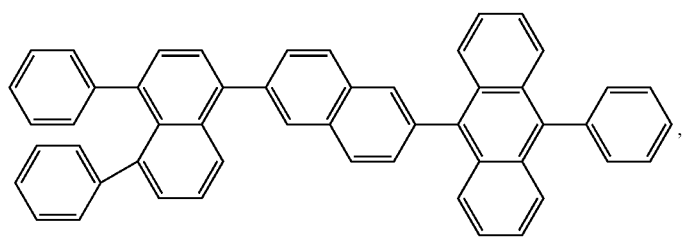
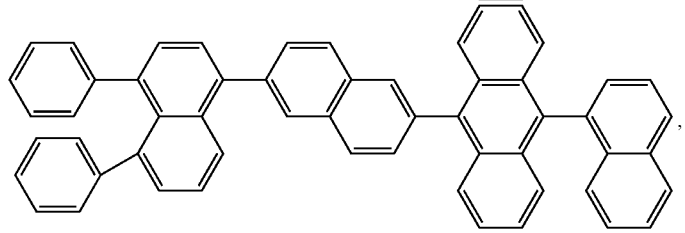
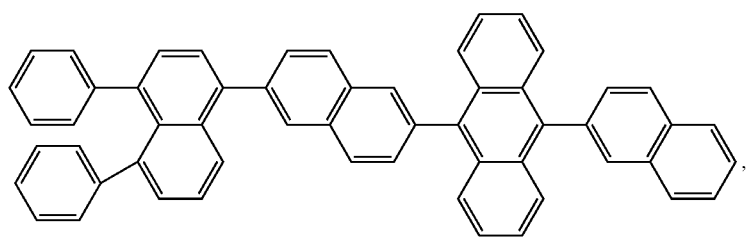
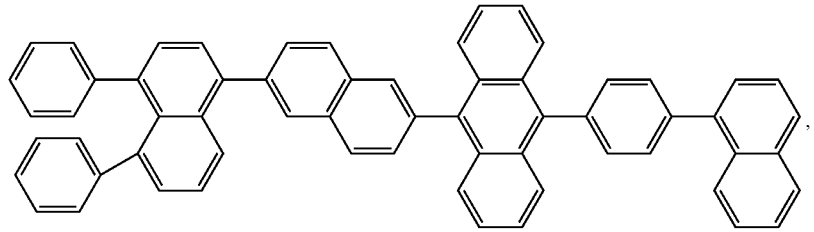
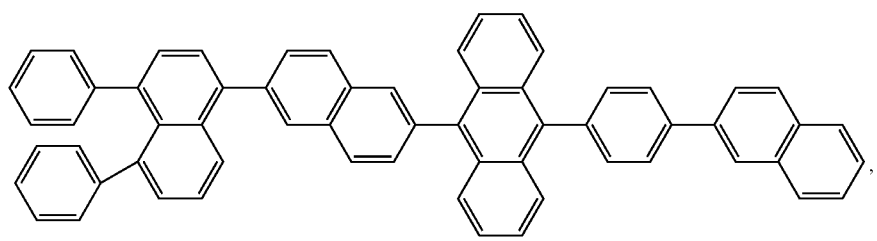
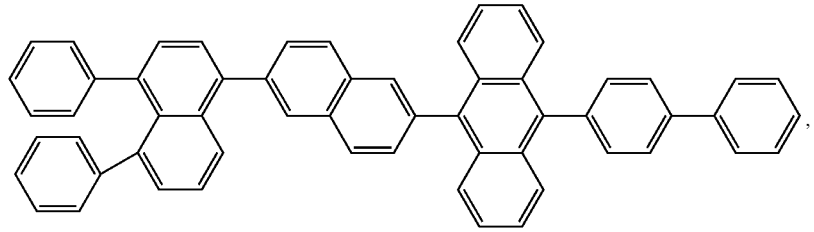

-continued
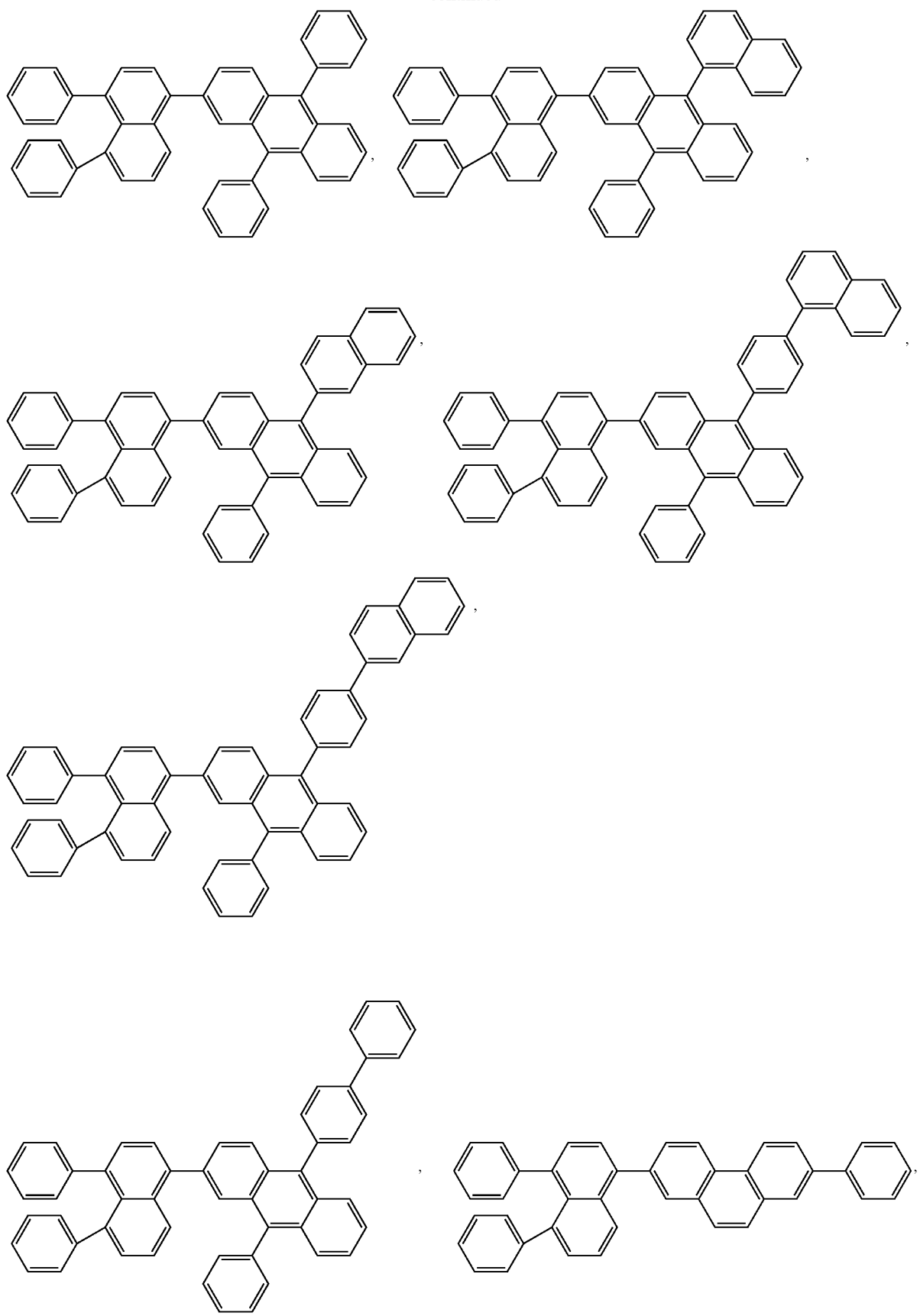

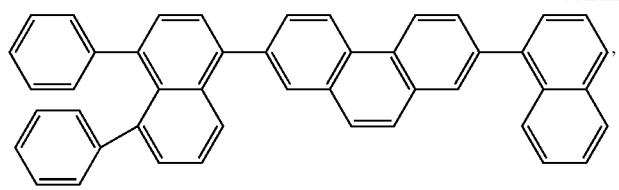
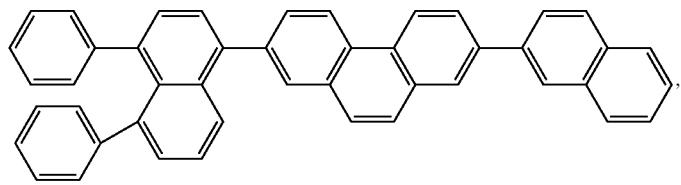
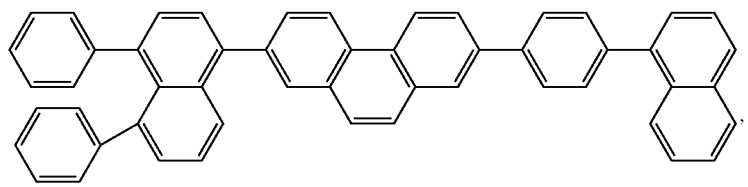
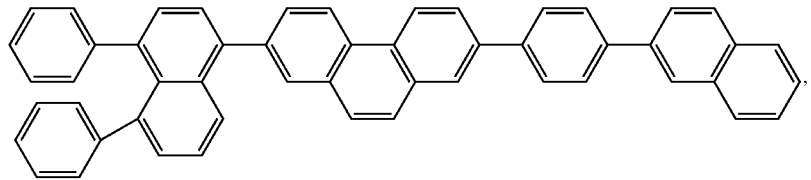
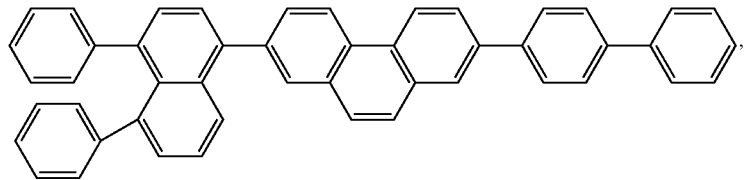
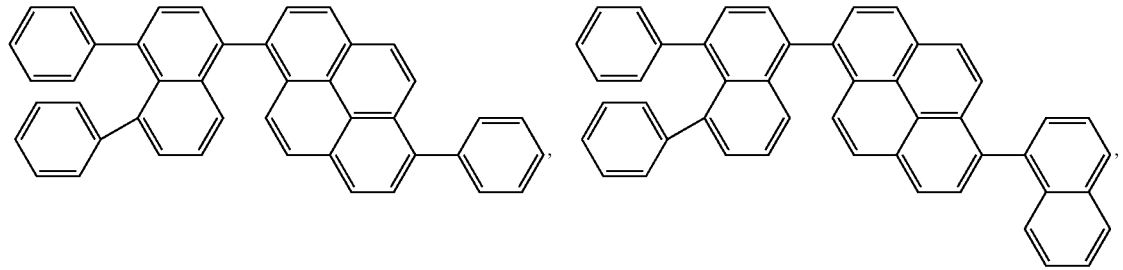
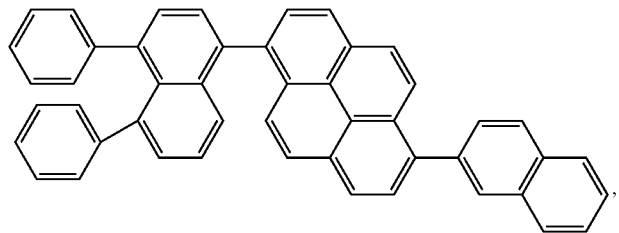

-continued
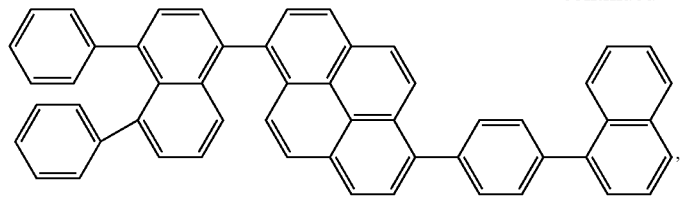
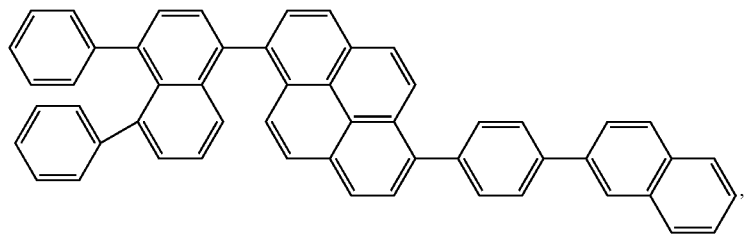
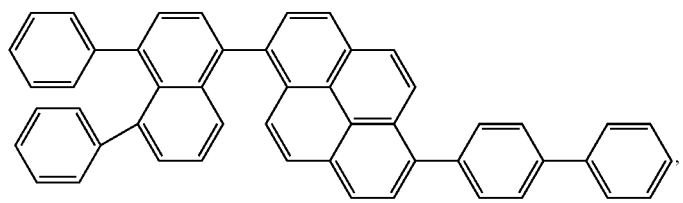
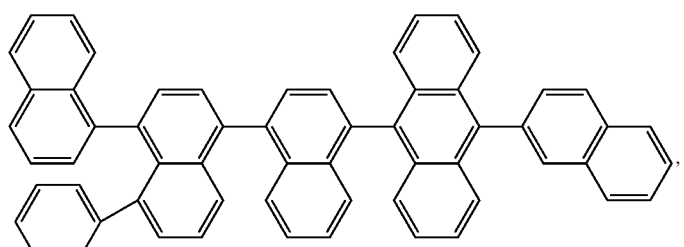
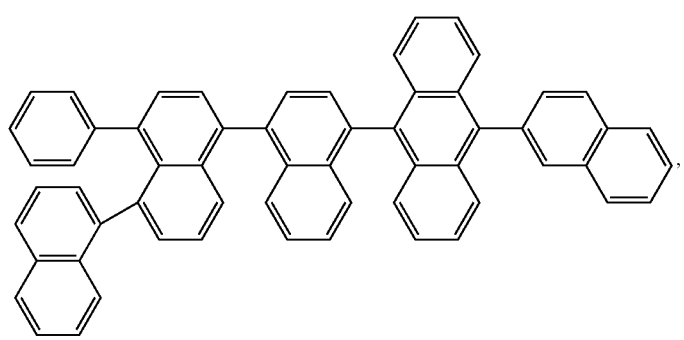
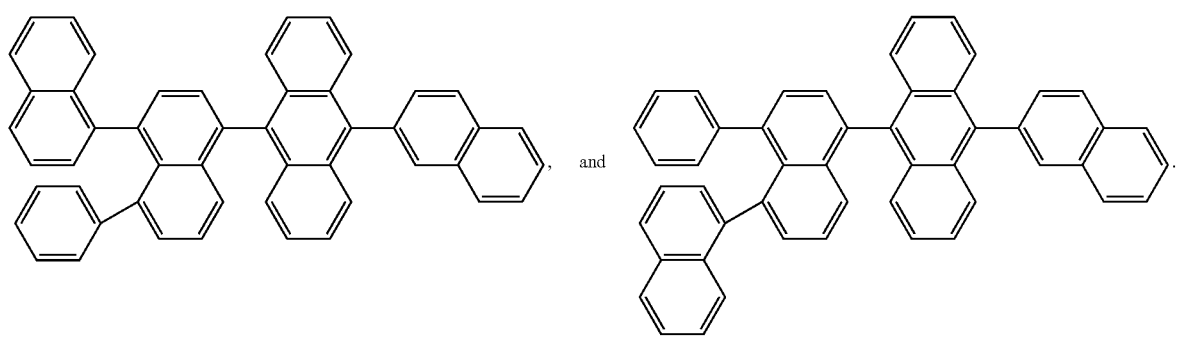
and The present invention also provides a method for preparing a compound of formula 1 wherein $Ar_2$ and $Ar_2$ are each hydrogen and $Ar_3$ is a $C_{6-10}$ monovalent aromatic group, the method being, for example, as shown in the following reaction scheme 1. $Ar_3$, $Ar_4$ and $Ar_5$ in the following reaction scheme 1 are as defined above.

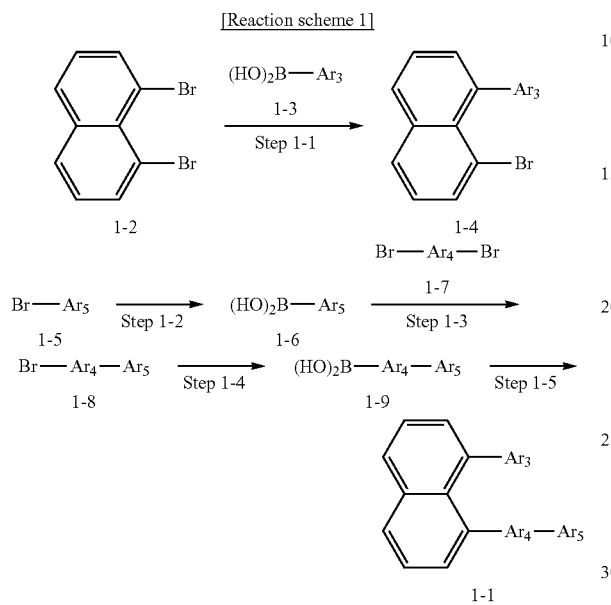

Step 1-1 in reaction scheme 1 is a step of reacting a compound represented by formula 1-2 with a compound represented by formula 1-3 to prepare a compound represented by formula 1-4. In this step, as a solvent, tetrahydrofuran may be used, and as a catalyst, tetrakis(triphenylphosphine)palladium(0) may be used together with a 2N aqueous solution of potassium carbonate.

Step 1-2 in reaction scheme 1 is a step of replacing the Br group of a compound represented by formula 1-5 with a $B(OH)_2$ group to prepare a compound represented by formula 1-6. In this step, tetrahydrofuran may be used as a solvent, and n-butyl lithium and triethyl borate may be added for the reaction.

Step 1-3 in reaction scheme 1 is a step of reacting a compound represented by formula 1-6 with a compound represented by formula 1-7 to prepare a compound represented by formula 1-8. In this step, as a solvent, tetrahydrofuran may be used, and as a catalyst, tetrakis(triphenylphosphine)palladium(0) may be used together with a 2N aqueous solution of potassium carbonate.

Step 1-4 in reaction scheme 1 is a step of replacing the Br group of a compound represented by formula 1-8 with a $B(OH)_2$ group to prepare a compound represented by formula 1-9. In this step, tetrahydrofuran may be used as a solvent, and n-butyl lithium and triethyl borate may be added for the reaction.

Step 1-5 in reaction scheme 1 is a step of reacting a compound represented by formula 1-9 with the compound of formula 1-4, prepared in step 1-1, to prepare a compound represented by formula 1-1. In this step, as a solvent, tetrahydrofuran may be used, and as a catalyst, tetrakis(triphenylphosphine)palladium(0) may be used together with a 2N aqueous solution of potassium carbonate.

In addition, when $Ar_3$ and $Ar_4$—$Ar_5$ of the compound represented by formula 1-1 are the same substituents, the compound represented by formula 1 can be prepared through step 1 alone by controlling the molar ratio of the reactants that are used in step 1.

The present invention also provides a method for preparing a compound of formula 1 wherein $Ar_2$ and $Ar_2$ are each a $C_{6-10}$ monovalent aromatic group and $Ar_3$ is hydrogen, the method being, for example, as shown in the following reaction scheme 2. $Ar_1$, $Ar_2$, $Ar_4$ and $Ar_5$ in the following reaction scheme 2 are as defined above.

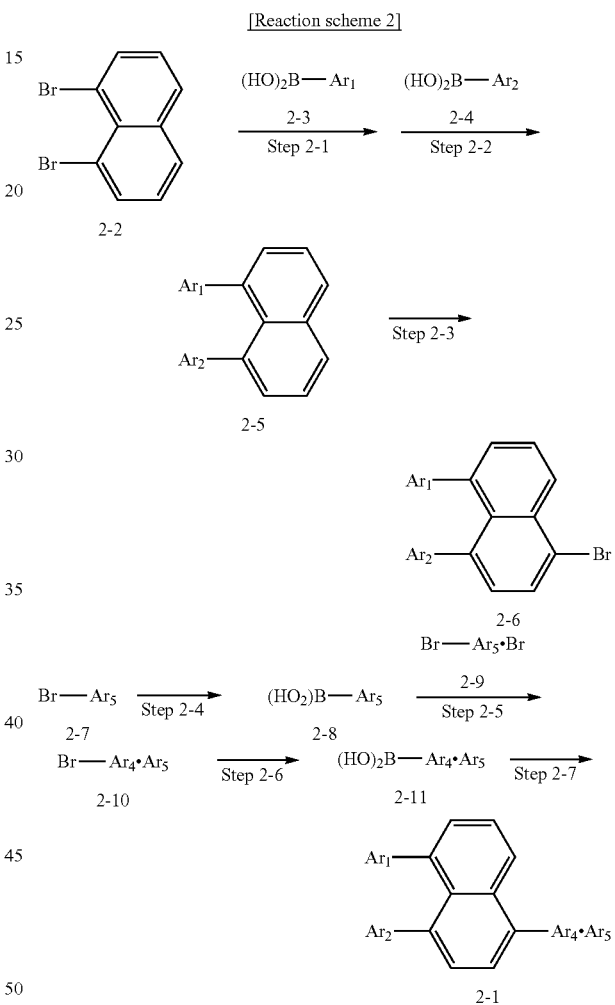

Steps 2-1 and 2-2 in reaction scheme 2 are the steps of reacting a compound represented by formula 2-2 sequentially with compounds represented by formulas 2-3 and 2-4 to prepare a compound represented by formula 2-5. In these steps, as a solvent, tetrahydrofuran may be used, and as a catalyst, tetrakis(triphenylphosphine)palladium(0) may be used together with a 2N aqueous solution of potassium carbonate. When the substituents $Ar_1$ and $Ar_2$ are the same, the compound represented by formula 2-5 can be prepared through a single step by controlling the molar ratio of the reactants.

Step 2-3 in reaction scheme 2 is a step of reacting a compound represented by formula 2-5 with bromine to prepare a compound represented by formula 2-6. In this step, chloroform may be used as a solvent.

Step 2-4 in reaction scheme 2 is a step of replacing the Br group of a compound represented by formula 2-7 with a B(OH)$_2$ group to prepare a compound represented by formula 2-8. In this step, tetrahydrofuran may be used as a solvent, and n-butyl lithium and triethyl borate may be added for the reaction.

Step 2-5 in reaction scheme 2 is a step of reacting the compound represented by formula 2-8 with a compound represented by formula 2-9 to prepare a compound represented by formula 2-10. In this step, as a solvent, tetrahydrofuran may be used, and as a catalyst, tetrakis(triphenylphosphine)palladium(0) may be used together with a 2N aqueous solution of potassium carbonate.

Step 2-6 in reaction scheme 2 is a step of replacing the Br group of the compound represented by formula 2-10 with a B(OH)$_2$ group to prepare a compound represented by formula 2-11. In this step, tetrahydrofuran may be used as a solvent, and n-butyl lithium and triethyl borate may be added for the reaction.

Step 2-7 in reaction scheme 2 is a step of reacting the compound represented by formula 2-11 with the compound represented by formula 2-6, prepared in step 2-3, to prepare a compound represented by formula 2-1. In this step, as a solvent, tetrahydrofuran may be used, and as a catalyst, tetrakis(triphenylphosphine)palladium(0) may be used together with a 2N aqueous solution of potassium carbonate.

The present invention also provides a material for an organic electroluminescent device, which comprises the compound represented by formula 1. The compound represented by formula 1 may be used as a hole injection material, a hole transport material, a light-emitting material, an electron transport material and an electron injection material in an organic electroluminescent device, depending on the kind of substituents and characteristics thereof. In particular, the compound represented by formula 1 can be used as a host or dopant material for a light-emitting layer, and when it is used in a device, it can improve the driving voltage, thermal stability, lifetime, color purity and luminous efficiency of the device.

The present invention also provides an organic electroluminescent device which includes one or more organic thin film layers including at least one light-emitting layer and sandwiched between a cathode and an anode, wherein at least one of the organic thin film layers contains the compound represented by formula 1.

An organic electroluminescent device having a monolayer structure comprises a substrate, an anode, a cathode, and a light-emitting layer between the anode and the cathode. A organic electroluminescent device having a multilayer structure has a structure in which a combination of two or more of a hole-injecting layer, a hole-transporting layer, an electron blocking layer, an organic light-emitting layer, a hole blocking layer, an electron-transporting layer and an electron-injecting layer, which are formed of an organic material, an organometallic complex, a metal salt or the like, is sandwiched between an anode and a cathode. Herein, the combination of the layers is selected according to the kind and characteristics of the constituent materials.

The organic electroluminescent device having a multilayer structure has an advantage in that a decrease in luminance or lifetime due to quenching can be prevented or a voltage that is applied thereto can be lowered. A layer into which holes are injected from an anode is referred to as "hole-injecting layer", and a layer for receiving holes from the hole-injecting layer and transporting the holes to a light-emitting layer is referred to as "hole-transporting layer", and an electron blocking layer for blocking the movement of an electron to the hole-transporting layer may also be formed between the organic light-emitting layer and the hole-transporting layer. If necessary, a material capable of performing both the injection and transport of holes may be selected so that the hole-injecting layer and the hole-transporting layer are not individually formed. Similarly, a layer into which electrons are injected from a cathode is referred to as "electron-injecting layer", and a layer for receiving electrons from the electron-injecting layer and transporting the electrons to the light-emitting layer is referred to as "electron-transporting layer". In addition, a hole blocking layer for blocking the movement of a hole to the electron-transporting layer may also be formed between the organic light-emitting layer and the electron-transporting layer. The light-emitting layer is a layer that emits light by recombination of a hole and an electron and may be composed of a single material or 2 to 5 different materials. When the light-emitting layer is composed of two or more different materials, the light-emitting materials are referred to according to their role. Specifically, the main constituent material of the light-emitting layer is referred to as "host", and other material(s) is referred to as "dopant".

The inventive compound represented by formula 1 may be used as a host or dopant material. In addition, the inventive compound represented by formula 1 may be used as a host, and compounds other than the inventive compound represented by formula 1 may be used as a dopant. Conversely, compounds other than the inventive compound represented by formula 1 may be used as a host, and the inventive compound represented by formula 1 may be used as a dopant.

Further, according to the emission wavelength of the inventive compound represented by formula 1, a layer that emits blue light, green light, red light, or a combination thereof may be formed, or two or more light-emitting layers may also be formed so as to emit white light. Each of the layers is selected depending on the energy level or heat resistance of the material, the adhesion of the material to an organic layer or a metal electrode, or other factors. In a preferred embodiment of the present invention, an organic electroluminescent device comprises an anode, a hole-injecting layer, a hole-transporting layer, a light-emitting layer, an electron-transporting layer, an electron-injecting layer and a cathode, which are formed in that order on a substrate.

The substrate functions as a support during the preparation of the organic electroluminescent device and as a protective layer for the device. Generally, the substrate is required to have smoothness, mechanical strength, and thermal stability capable of withstanding various processes, emit no volatile compounds, and to be impermeable to air and moisture and transparent. However, in the case of devices requiring cathode directional emission or side emission, a highly reflective substrate may also be used. Examples of transparent materials include glass, quartz, a transparent resin film and the like. Examples of the transparent resin film include polyethylene, an ethylene-vinyl acetate copolymer, an ethylene-vinyl alcohol copolymer, polystyrene, polymethylmethacrylate, polyvinyl chloride, polyvinyl alcohol, polyvinyl butyral, nylon, polyether ether ketone, polysulfone, polyether sulfone, a tetrafluoroethylene-perfluoroalkyl vinyl ether copolymer, polyvinyl fluoride, a tetrafluoroethylene-ethylene copolymer, a tetrafluoroethylene-hexafluoropropylene copolymer, polychlorotrifluoroethylene, polyvinylidene fluoride, polyester, polycarbonate, polyurethane, polyether imide, polyimide, polypropylene and the like. Non-transparent substrate materials that may be used in the present invention include silicon wafers, ceramic materials, metals such as chromium or gold, and the like. The above substrate materials may be used to form a multilayer structure.

The anode of the organic electroluminescent device is a conductive thin film to which a power source can be connected, and it preferably has a relatively high work function (preferably, 4 eV or higher) so that holes can be easily injected. Examples of the material of the anode include carbon, aluminum, vanadium, iron, chromium, copper, zinc, cobalt, nickel, tungsten, silver, gold, platinum, palladium, and alloys thereof, metal oxides such as ITO, tin oxide or indium oxide, and organic conductive resins such as polythiophene or polypyrrole. The thickness of the anode is about 10 nm to about 1000 nm, preferably 10 nm to 500 nm.

A conductive material that is used for the cathode preferably has a relatively low work function (4 eV or lower) in order to inject electrons, and examples thereof include, but are not limited to, magnesium, calcium, tin, lead, titanium, yttrium, lithium, ruthenium, manganese, aluminum, and alloys thereof. Typical examples of the alloys include, but are not limited to, magnesium/silver, magnesium/indium, lithium/aluminum, and the like. The ratio of metals in the alloy is controlled by the temperature of a deposition source, an atmosphere, the degree of vacuum and selected to have a suitable ratio. The anode and the cathode may have a layer structure composed of two or more layers as required. For efficient light emission, at least one side of the organic electroluminescent device is preferably sufficiently transparent in the emission wavelength region of the device. The transparent electrode is formed using the above conductive material by a method such as deposition or sputtering such that a predetermined light transmittance is secured. The electrode on the light emission side preferably has a light transmittance of at least 10%.

The light-emitting material of the light-emitting layer preferably has a very high fluorescence quantum yield (about 1.0) and high charge transport ability and forms a uniform thin film. When the organic electroluminescent device has a multilayer structure, a decrease in luminance or lifetime due to quenching can be prevented. Depending on the need, the compounds represented by formula 1 may be used alone or in combination of two or more or may be used together with a known light-emitting host material or light-emitting dopant material. When this compound is used as a single light-emitting layer material or host material, it is preferably added to a concentration of 80-100 wt %. Further, when the compound is used as a light-emitting dopant material, it is preferably added to a concentration of 0.01-20 wt %. Examples of a light-emitting material or dopant material that may be used together with the inventive compound represented by formula 1 in the light-emitting layer include, but are not limited to, anthracene, naphthalene, phenanthrene, pyrene, tetracene, coronene, chrysene, fluorescein, perylene, phthaloperylene, naphthaloperylene, perynone, phthaloperynone, naphthaloperynone, diphenyl butadiene, tetraphenyl butadiene, coumarin, oxadiazole, aldazine, bisbenzoxazoline, bisstyryl, pyrazine, cyclopentadiene, quinoline metal complexes, aminoquinoline metal complexes, benzoquinoline metal complexes, imine, diphenylethylene, vinylanthracene, diaminocarbazole, pyran, thiopyran, polymethine, merocyanine, imidazole chelated oxinoid compounds, quinacridone, rubrene, and derivatives thereof. Criteria for selection of the light-emitting material that is used as a dopant material are as follows: 1) the dopant material should have high-efficiency fluorescence or phosphorescence; and 2) the dopant material should have a bandgap corresponding to about 60-100% (preferably 80-100%) of that of the host material.

The material of the hole-injecting layer is a material functioning to inject a plurality of holes from the anode in an applied electric field, and the hole-injecting layer is formed if the interfacial tension between the anode and the hole-transporting layer is not sufficiently high or if the work function of the anode significantly differs from the highest occupied molecular orbital (HOMO) of a layer adjacent thereto. The hole-injecting layer efficiently lowers the potential barrier of hole injection, and as a result, reduces the driving voltage of the organic electroluminescent device. Thus, the hole-injecting layer should be formed of a compound which has the ability to transport holes, has high efficiency with which holes are injected from the anode, maintains a stable interface with the anode, and essentially has excellent thermal stability. Thus, the hole-injecting layer may be made of the inventive compound represented by formula 1 or an already known material. Examples of the known material include, but are not limited to, a phthalocyanine derivative, a naphthalocyanine derivative, a porphyrin derivative, oxazole, oxadiazole, triazole, imidazole, imidazolone, imidazolethione, pyrazoline, pyrazolone, tetrahydroimidazole, hydrazone, acylhydrazone, polyarylalkane, stilbene, butadiene, benzidine type triphenylamine, styrylamine type triphenylamine, diamine type triphenylamine, derivatives thereof, and polymer materials such as polyvinyl carbazole, polysilane, and a conductive polymer (PEDOT/PSS). Of hole-injecting materials that may be used in the organic electroluminescent device of the present invention, a more effective hole-injecting material is an aromatic tertiary amine derivative or a phthalocyanine derivative. Specific examples of the aromatic tertiary amine derivative include, but are not limited to, triphenylamine, tritolylamine, tolyldiphenylamine, N,N'-diphenyl-N,N'-(3-methylphenyl)-1,1'-biphenyl-4,4'-diamine, N,N,N',N'-(4-methylphenyl)-1,1'-phenyl-4,4'-diamine, N,N,N',N'-(4-methylphenyl)-1,1'-biphenyl-4,4'-diamine, N,N'-diphenyl-N,N'-dinaphthyl-1,1'-biphenyl-4,4'-diamine, 4,4'-bis{N-[4-(N,N-di-m-tolylamino)phenyl]-N-phenylamino}biphenyl, N,N'-biphenyl-N,N'-bis-[4-(phenyl-m-tolyl-amino)-phenyl]-biphenyl-4,4'-diamine, N,N'-(methylphenyl)-N,N'-(4-n-butylphenyl)phenanthrene-9,10-diamine, N,N-bis(4-di-4-tolylaminophenyl)-4-phenylcyclohexane, and an oligomer or polymer having the aromatic tertiary amine skeleton. Specific examples of the phthalocyanine (Pc) derivative include, but are not limited to, phthalocyanine derivatives such as $H_2Pc$, CuPc, CoPc, NiPc, ZnPc, PdPc, FePc, MnPc, ClAlPc, ClGaPc, ClInPc, ClSnPc, $Cl_2SiPc$, (HO)AlPc, (HO)GaPc, VOPc, TiOPc, MoOPc, GaPc-O—GaPc, and naphthalocyanine derivatives.

The hole-transporting layer functions to smoothly transport holes from the hole-injecting layer or the anode to the light-emitting layer. Further, the hole-transporting layer has high hole mobility, and stability against holes, and functions to block electrons. In addition to these general requirements, the hole-transporting layer requires heat resistance when being applied in display devices for cars and is preferably made of a material having a glass transition temperature (Tg) of 80° C. or higher. Materials satisfying such requirements include 4,4'-bis[N-(1-naphthyl)-N-phenylamino]biphenyl (NPB), a spiro-arylamine-based compound, a perylene-arylamine-based compound, an azacycloheptatriene compound, bis(diphenylvinylphenyl)anthracene, a silicon germanium oxide compound, a silicon-based arylamine compound, and the like. Meanwhile, a typical organic single molecular material for the hole-transporting layer is an arylamine compound having high hole transport rate and excellent electrical stability. In the past, N,N'-diphenyl-N,N'-bis(3-methylphenyl)-1,1'-diphenyl-4,4'-diamine (TPD) was frequently used as an organic material for a hole-transporting layer. However, because TPD is unstable at a temperature of 60° C. or higher, N-naphthyl-N-phenyl-1,1'-diphenyl-4,4'-diamine (NPB)- based materials or amine compounds substituted with a greater number of aromatic groups that have a higher glass transition temperature are used at the present time. Particularly, because organic single molecules for a hole-transporting layer should have a high hole transport rate and form an interface with a light emitting layer, they should have an adequate ionization potential value of between that of a hole-injecting layer and that of a light-emitting layer so as to inhibit the generation of exitons at the interface between the hole-transporting layer and the light emitting layer. Further, the organic single materials for the hole transporting layer are required to have the ability to control the electrons transported from the light-emitting layer.

The material of the electron-transporting layer is preferably a compound that has the ability to transport electrons, the ability to transport electrons from the cathode to the light emitting layer or the light emitting material, the ability to prevent the excitons produced in the light emitting layer from moving to the hole-transporting layer, and an excellent ability to form a thin film. Specific examples of the material of the electron-transporting layer include, but are not limited to, fluorenone, anthraquinodimethane, diphenoquinone, thiopyran dioxide, oxazole, oxadiazole, triazole, imidazole, perylenetetracarboxylic acid, fluorenylidenemethane, anthrone, and derivatives thereof, and the inventive compound represented by formula 1.

A more effective electron-transporting material for use in the organic electroluminescent device of the present invention is a metal complex compound or a nitrogen-containing five-membered ring derivative. Specific examples of the metal complex compound include, but are not limited to, (8-quinolinol) lithium, bis(8-quinolinol)zinc, bis(8-quinolinol)copper, bis(8-quinolinol)manganese, tris(8-quinolinol) aluminum, tris(2-methyl-8-quinolinol)aluminum, tris(8-quinolinol)gallium, bis(10-hydroxybenzo[h]quinolinate) beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, and bis(2-methyl-8-quinolinato)(2-naphtholato)gallium. Also, the nitrogen-containing five-membered-ring derivative is preferably an oxazole derivative, a thiazole derivative, an oxadiazole derivative, a thiadiazole derivative, and a triazole derivative. Specific examples of the derivative include, but are not limited to, 2,5-bis(1-phenyl)-1,3,4-oxazole, 2,5-bis(1-phenyl)-1,3,4-thiazole, 2,5-bis(1-phenyl)-1,3,4-oxadiazole, 2-(4'-tert-butylphenyl)-5-(4"-biphenyl)-1,3,4-oxadiazole, 2,5-bis(1-naphthyl)-1,3,4-oxadiazole, 1,4-bis[2-(5-phenyloxadiazolyl)]benzene, 1,4-bis[2-(5-phenyloxadiazolyl)-4-tert-butylbenzene], 2-(4'-tert-butylphenyl)-5-(4"-biphenyl)-1,3,4-thiadiazole, 2,5-bis(1-naphthyl)-1,3,4-thiadiazole, 1,4-bis[2-(5-phenylthiadiazolyl)]benzene, 2-(4'-tert-butylphenyl)-5-(4"-biphenyl)-1,3,4-triazole, 2,5-bis(1-naphthyl)-1,3,4-triazole, and 1,4-bis[2-(5-phenyltriazolyl)]benzene.

In the present invention, an inorganic compound layer may be disposed between the light emitting layer and the electrode in order to improve charge injection. Examples of the material of the inorganic compound layer include alkali metal compounds (fluoride, oxide, etc.), alkaline earth metal compounds, and the like, and specific examples include LiF, $Li_2O$, BaO, SrO, $BaF_2$, $SrF_2$ and the like.

In order to increase the stability and lifetime of the inventive organic electroluminescent device against a temperature and humidity atmosphere, a protective layer may be formed on the surface of the device, or the device may be protected by coating with silicone oil or resin.

Each layer of the organic electroluminescent device may be formed using any method of dry film formation methods such as vacuum deposition, sputtering, plasma or ion plating, and wet film formation methods such as spin coating, dip coating or flow coating. The thickness of the film is not specifically limited, but a suitable film thickness needs to be set. If the film thickness is too thick, a high voltage will be required to obtain a specific light output, resulting in a decrease in efficiency. If the film thickness is too thin, pin holes or the like will occur, and thus sufficient luminance will not be obtained even when an electric field is applied. The film thickness is preferably 5 nm to 10 µm, and more preferably 10 nm to 0.2 µm. In the case of the wet film formation method, a thin film is formed by dissolving or dispersing a material for each layer in a suitable solvent such as ethanol, chloroform, tetrahydrofuran or dioxane, but the solvent is not limited. Further, a suitable resin or additive for improving film formation and preventing the occurrence of pin holes in the film may be used in any organic thin film layer. Examples of resin that may be used for this purpose include insulating resins, such as polystyrene, polycarbonate, polyarylate, polyester, polyamide, polyurethane, polysulfone, polymethyl methacrylate, polymethyl acrylate, or cellulose, and copolymers thereof; photoconductive resins such as poly-N-vinylcarbazole or polysilane; and conductive resins such as polythiophene or polypyrrole. In addition, examples of the additive include antioxidants, UV absorbers, plasticizers and the like.

DESCRIPTION OF SPECIFIC EMBODIMENTS OF THE INVENTION

Figure 1:
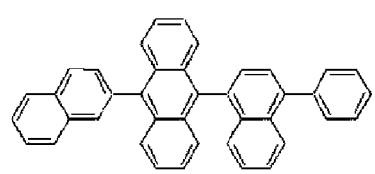
FIG. 1 shows the three-dimensional structures of a general anthracene compound and a compound of Example 23.
Figure 1:
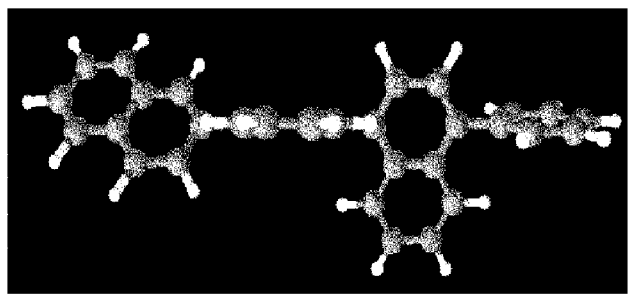
Figure 1:
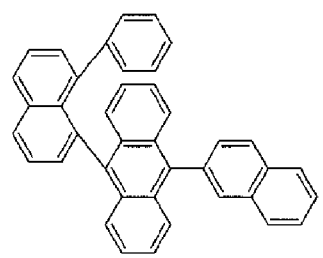
Figure 1:
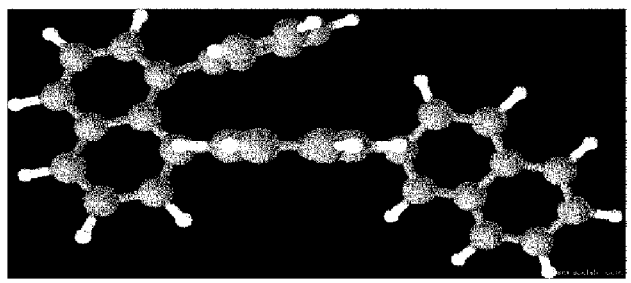
Figure 2:
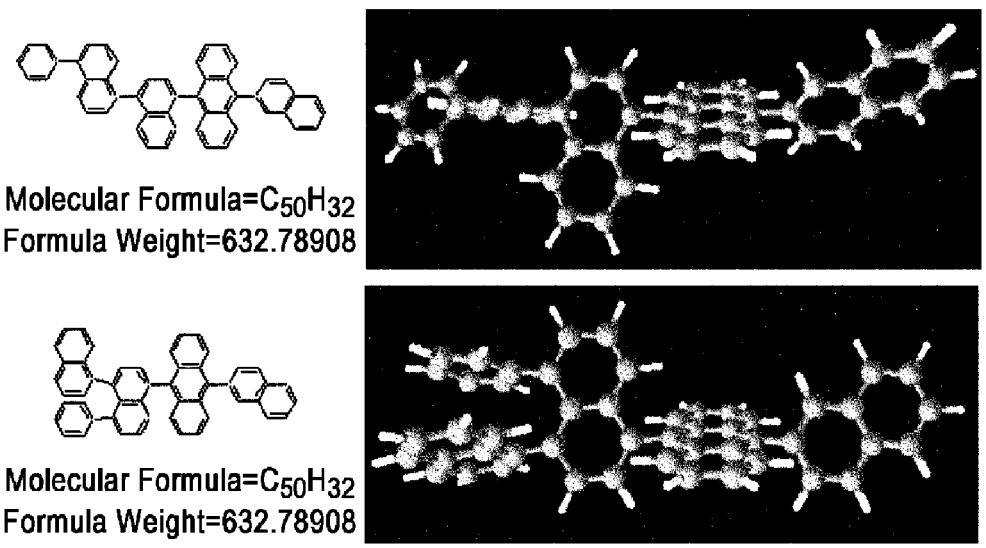
FIG. 2 shows that the three-dimensional structure of 1,8-substituted naphthalene (Example 95) is more distorted than that of 1,4-substituted naphthalene.

Hereinafter, the present invention will be described in further detail with reference to examples. It is to be understood, however, that these examples are for illustrative purposes only and are not intended to limit the scope of the present invention.

Example 1

A compound of Example 1 was prepared according to the following preparation method.

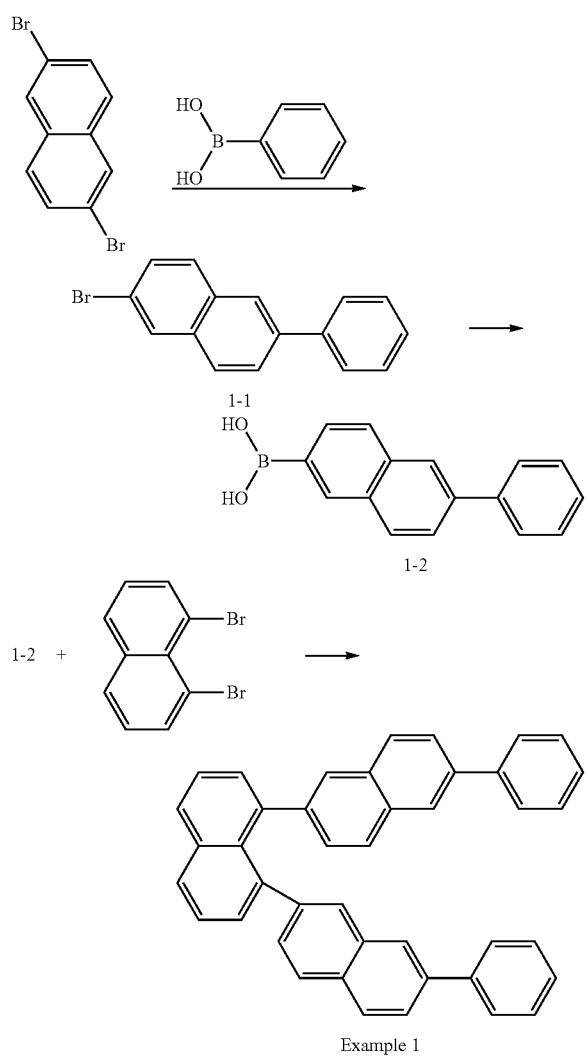

Example 1

Step 1: Preparation of Intermediate 1-1

2,6-dibromonaphthalene (50 g, 170 mmol), phenylboronic acid (23 g, 190 mmol) and tetrakis(triphenylphosphine)palladium(0) (6.1 g, 10 mmol) were dissolved in 500 mL of tetrahydrofuran, and 260 mL of a 2N aqueous solution of potassium carbonate was added thereto. Then, the mixture was allowed to react under reflux for 24 hours. After completion of the reaction, the reaction solution was extracted with ethyl acetate, and the organic layer was dried using anhydrous magnesium sulfate, and then purified through a hexane column, thereby obtaining intermediate 1-1 at a yield of 75% (37 g).

Step 2: Preparation of Intermediate 1-2

Intermediate 1-1 (50 g, 180 mmol) was dissolved in 1000 mL of tetrahydrofuran under an argon atmosphere, and 1.6 M n-butyl lithium (121 mL) was added thereto at −78° C., followed by stirring for about 1 hour. At the same temperature, triethyl borate (36 mL, 210 mmol) was slowly added dropwise thereto, and the mixture was stirred for 2 hours, and then stirred at room temperature for 12 hours. After completion of the reaction, the reaction solution was extracted with ethyl acetate, and the organic layer was dried using anhydrous magnesium sulfate, and then purified through a dichloromethane column, thereby obtaining intermediate 1-2 at a yield of 78% (34 g).

Step 3: Preparation of Compound of Example 1

1,8-dibromonaphthalene (10 g, 30 mmol), intermediate 1-2 (20 g, 80 mmol) and tetrakis(triphenylphosphine)palladium(0) (2 g, 1.7 mmol) were dissolved in 500 mL of tetrahydrofuran, and 70 mL of a 2N aqueous solution of potassium carbonate was added thereto. Then, the mixture was allowed to react under reflux for 24 hours. After completion of the reaction, the reaction solution was extracted with ethyl acetate, and the organic layer was dried using anhydrous magnesium sulfate, and then purified through a hexane column, thereby obtaining a compound of Example 1 at a yield of 70% (13 g).

$^1$H NMR (200 MHz, CDCl$_3$): d 7.44-7.51 (m, 6H), 7.56-7.67 (m, 8H), 7.71-7.78 (m, 8H), 7.88-7.95 (m, 4H), 8.32-8.41 (m, 2H)

Example 2

The following compound was prepared in the same manner as described in Example 1, except that 1,6'-binaphthyl-2'-ylboronic acid was used instead of intermediate 1-2.

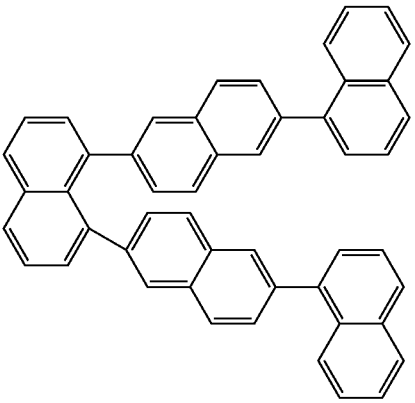 [SMILES: c1ccc2c(-c3ccc4cc(-c5cccc6cccc(-c7ccc8cc(-c9cccc%10ccccc9%10)ccc8c7)c56)ccc4c3)cccc2c1]

$^1$H NMR (200 MHz, CDCl$_3$): d 7.28-7.32 (t, 2H), 7.43-7.46 (t, 2H), 7.57-7.71 (m, 18H), 7.88-7.93 (m, 4H), 8.40-8.46 (m, 4H), 8.50-8.56 (m, 2H)

Example 3

A compound of Example 3 was prepared according to the following method.

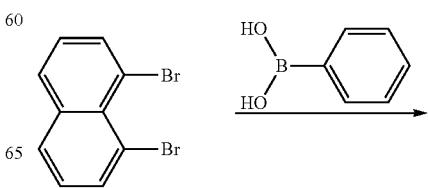

-continued

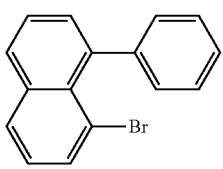

3-1

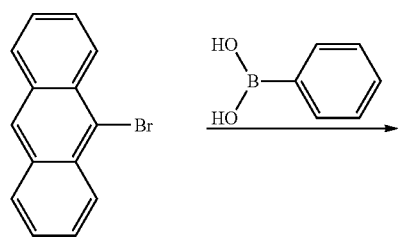

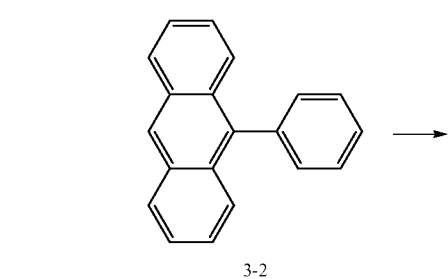

3-2

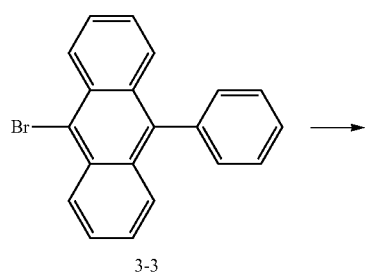

3-3

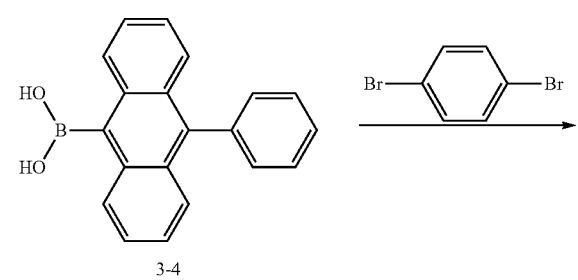

3-4

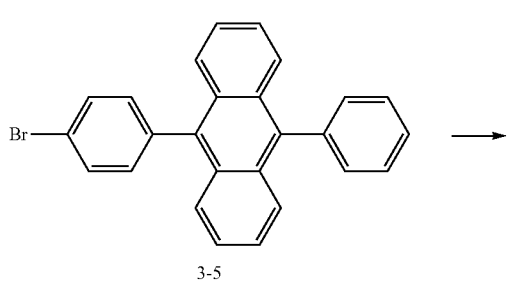

3-5

-continued

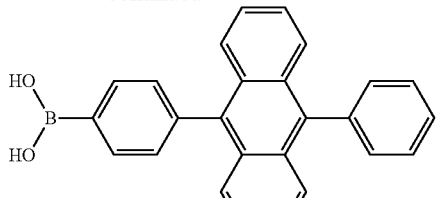

3-6

3-1 + 3-6 ⟶

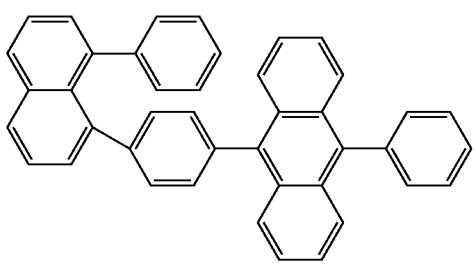

Example 3

Step 1: Preparation of Intermediate 3-1

1,8-dibromonaphthalene (50 g, 170 mmol), phenylboronic acid (23 g, 190 mmol) and tetrakis(triphenylphosphine)palladium(0) (6.1 g, 10 mmol) were dissolved in 500 mL of tetrahydrofuran, and 260 mL of a 2N aqueous solution of potassium carbonate was added thereto. Then, the mixture was allowed to react under reflux for 24 hours. After completion of the reaction, the reaction solution was extracted with ethyl acetate, and the organic layer was dried using anhydrous magnesium sulfate, and then purified through a hexane column, thereby obtaining intermediate 3-1 at a yield 63% (31 g).

Step 2: Preparation of Intermediate 3-2

9-bromoanthracene (50 g, 190 mmol), phenylboronic acid (31 g, 250 mmol) and tetrakis(triphenylphosphine)palladium (0) (6.7 g, 10 mmol) were dissolved in 1000 mL of tetrahydrofuran, and 291 mL of a 2N aqueous solution of potassium carbonate was added thereto. Then, the mixture was allowed to react under reflux for 24 hours. After completion of the reaction, the reaction solution was extracted with ethyl acetate, and the organic layer was dried using anhydrous magnesium sulfate, and then purified through a hexane column, thereby obtaining intermediate 3-2 at a yield of 91% (45 g).

Step 3: Preparation of Intermediate 3-3

Intermediate 3-2 (50 g, 200 mmol) was added to 500 mL of dimethylformamide, and NBS (45 g, 260 mmol) was added, followed by stirring at room temperature for 4 hours. 200 mL of water was added to the reaction solution and stirred for 2 hours, and then the produced solid material was filtered. The filtrate was washed with 100 mL of methanol, thereby obtaining intermediate 3-3 at a yield of 95% (62 g).

Step 4: Preparation of Intermediate 3-4

Intermediate 3-3 (50 g, 150 mmol) was dissolved in 1000 mL of tetrahydrofuran under an argon atmosphere, and 1.6M n-butyl lithium (103 mL) was added thereto at −78° C., followed by stirring for about 1 hour. Triethyl borate (31 mL, 180 mmol) was slowly added dropwise thereto at the same temperature, and the solution was stirred for 2 hours, followed by stirring at room temperature for 12 hours. After completion of the reaction, the reaction solution was extracted with ethyl acetate, and the organic layer was dried using anhydrous magnesium sulfate, and then purified through a dichloromethane column, thereby obtaining intermediate 3-4 at a yield of 72% (32 g).

Step 5: Preparation of Intermediate 3-5

Intermediate 3-4 (50 g, 170 mmol), dibromobenzene (44 g, 180 mmol) and tetrakis(triphenylphosphine)palladium(0) (5.8 g, 10 mmol) were dissolved in 1000 mL of tetrahydrofuran, and 253 mL of a 2N aqueous solution of potassium carbonate was added thereto. Then, the mixture was allowed to react under reflux for 24 hours. After completion of the reaction, the reaction solution was extracted with ethyl acetate, the organic layer was dried using anhydrous magnesium sulfate, and the organic layer was purified through a hexane column, thereby obtaining intermediate 3-5 at a yield of 67% (46 g).

Step 6: Preparation of Intermediate 3-6

Intermediate 3-5 (50 g, 120 mmol) was dissolved in 1000 mL of tetrahydrofuran under an argon atmosphere, and 1.6 M n-butyl lithium (84 mL) was added thereto at −78° C., followed by stirring for about 1 hour. Then, triethyl borate (25 mL, 150 mmol) was slowly added dropwise thereto at the same temperature, and the solution was stirred for 2 hours, followed by stirring at room temperature for 12 hours. After completion of the reaction, the reaction solution was extracted with ethyl acetate, and the organic layer was dried using anhydrous magnesium sulfate, and then purified through a dichloromethane column, thereby obtaining intermediate 3-6 at a yield of 74% (34 g).

Step 7: Preparation of Compound of Example 3

Intermediate 3-1 (10 g, 40 mmol), intermediate 3-6 (16 g, 43 mmol) and tetrakis(triphenylphosphine)palladium(0) (1.2 g, 1.1 mmol) were dissolved in 1000 mL of tetrahydrofuran, and 54 mL of a 2N aqueous solution of potassium carbonate was added thereto. Then, the mixture was allowed to react under reflux for 24 hours. After completion of the reaction, the reaction solution was extracted with ethyl acetate, and the organic layer was dried using anhydrous magnesium sulfate, and then purified through a hexane column, thereby a compound of Example 3 at a yield of 64% (12 g).

Figure 3:
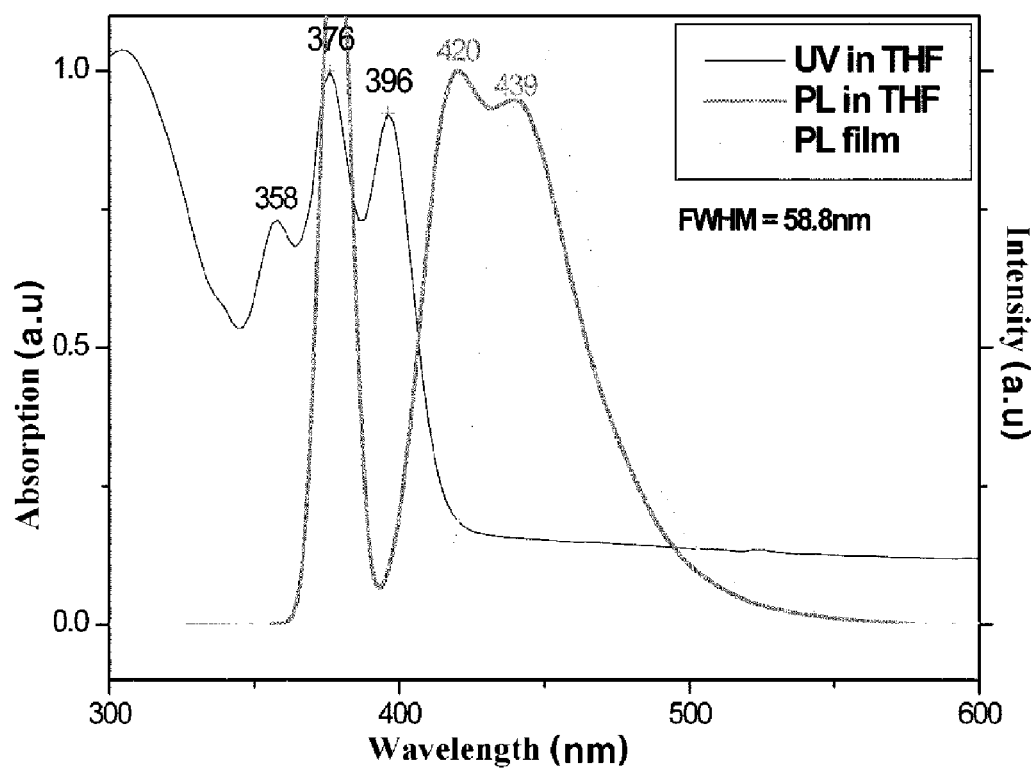
FIG. 3 shows the absorption and emission spectra of a compound of Example 3.
Figure 4:
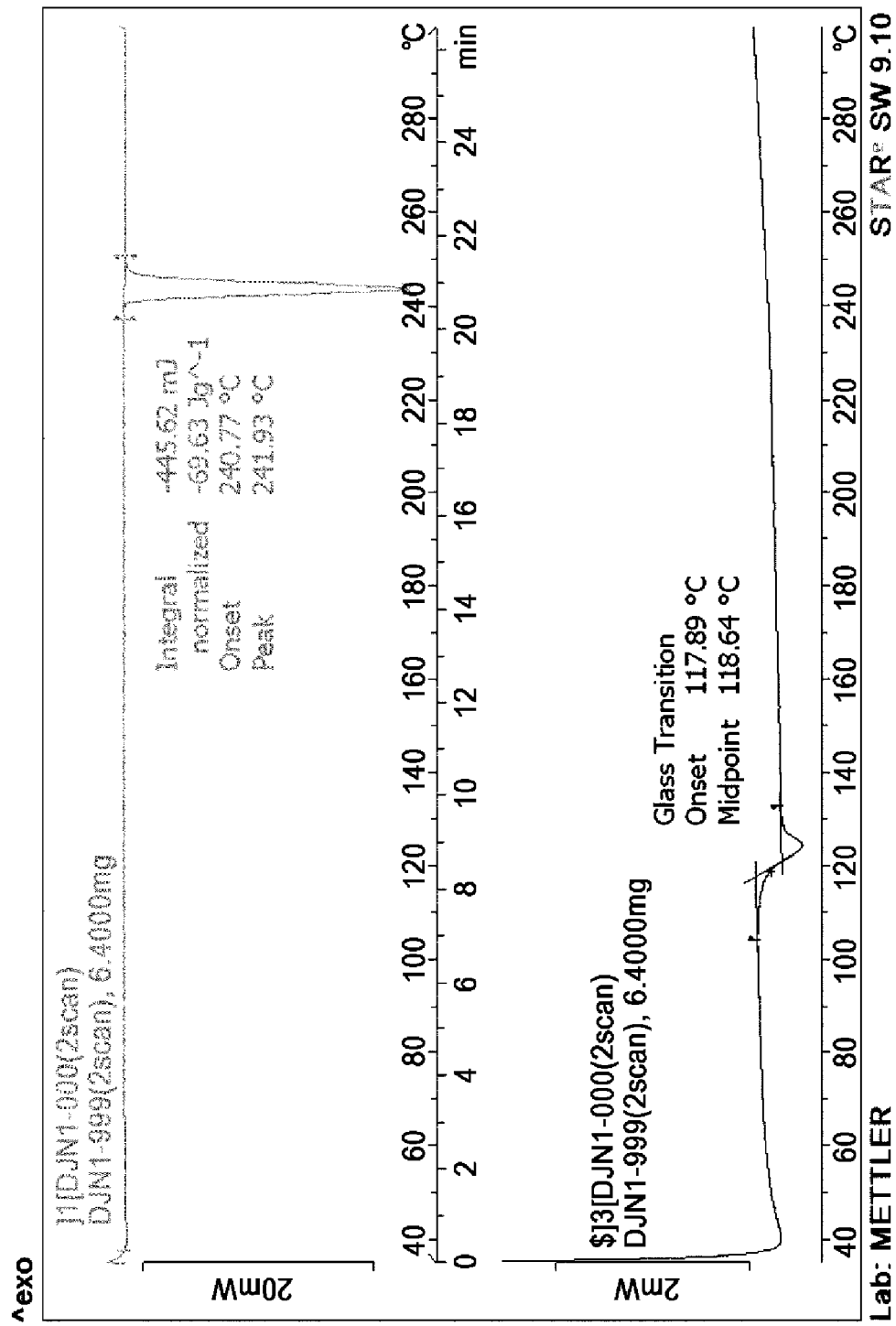
FIG. 4 is a graphic diagram showing the thermal characteristics of a compound of Example 3.
Figure 5:
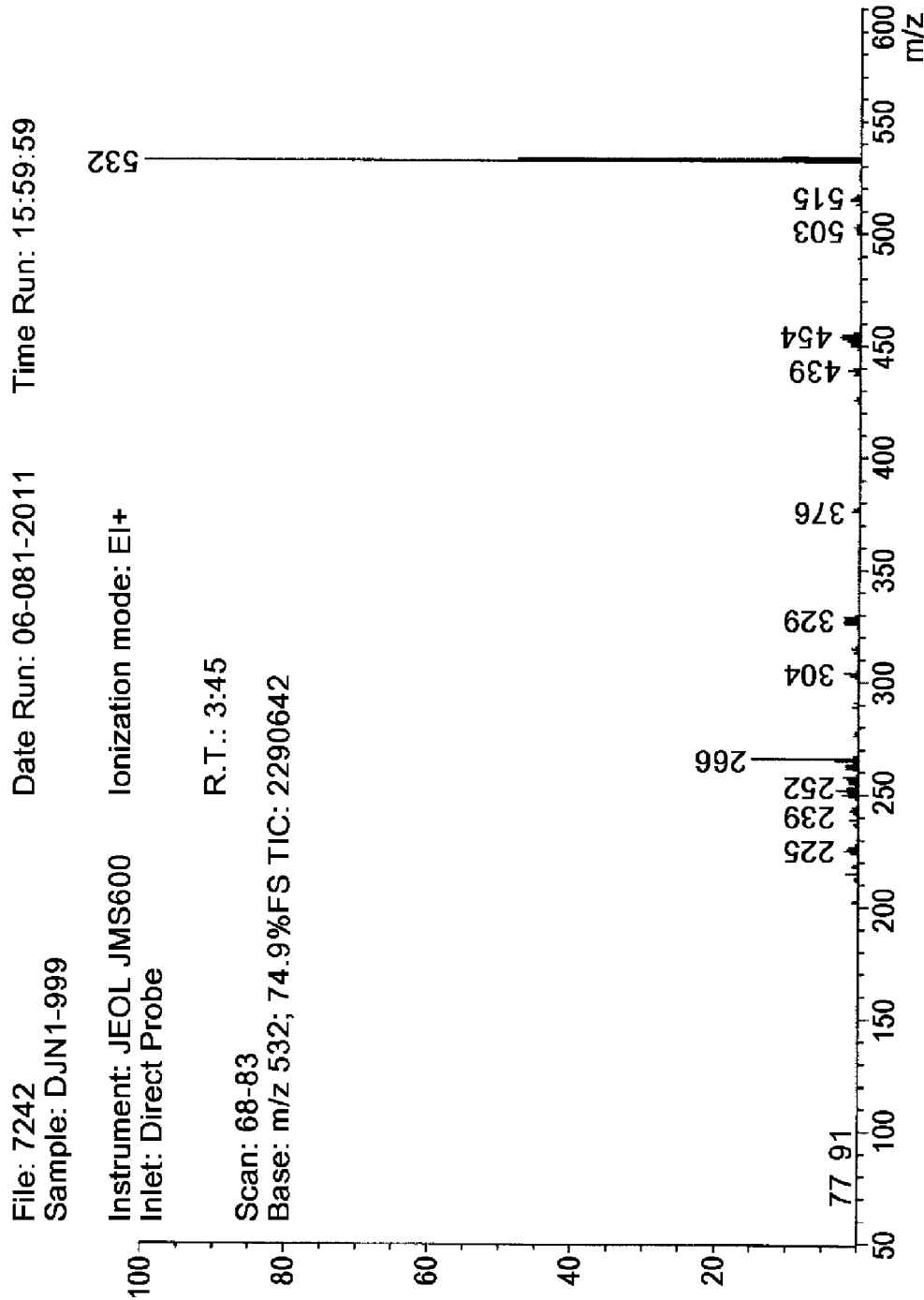
FIG. 5 shows the GC-mass spectrum of a compound of Example 3.
Figure 6:
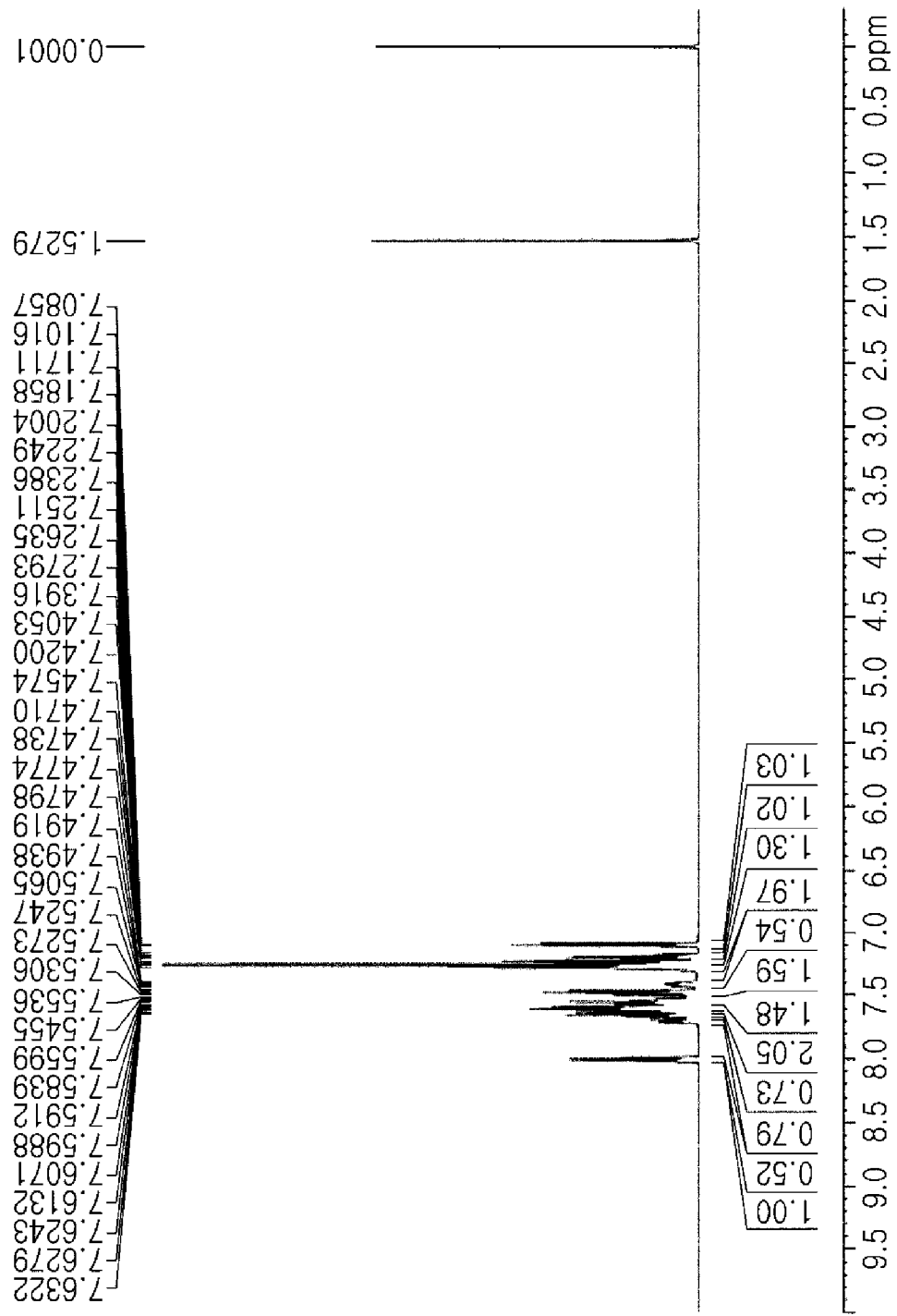
FIG. 6 shows the $^1$H-NMR spectrum of a compound of Example 3.
Figure 7:
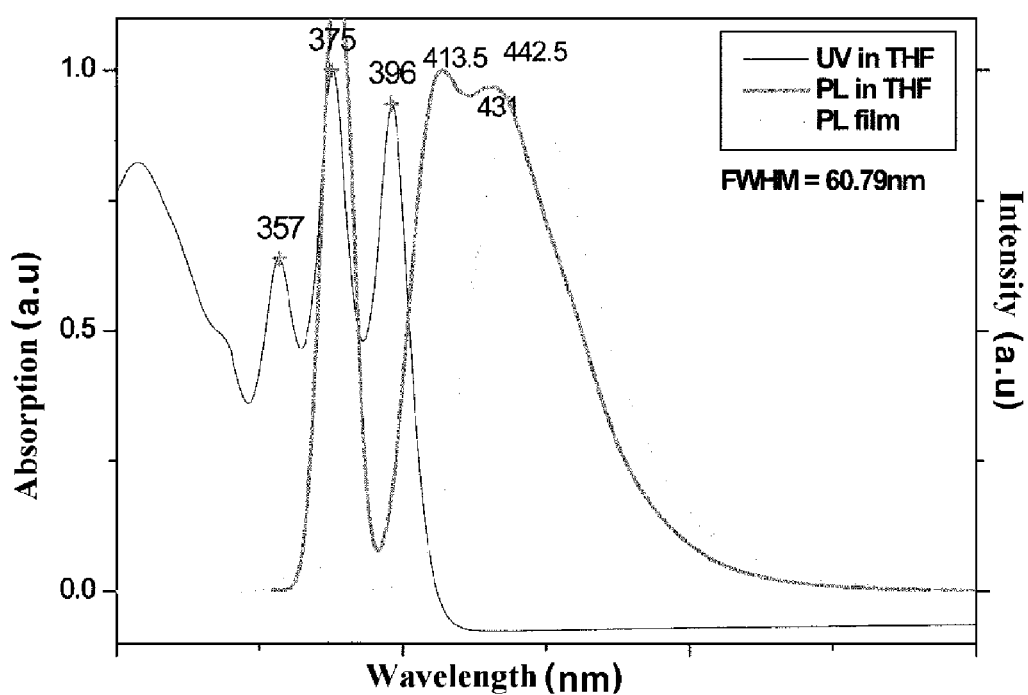
FIG. 7 shows the absorption and emission spectra of a compound of Example 51.
Figure 8:
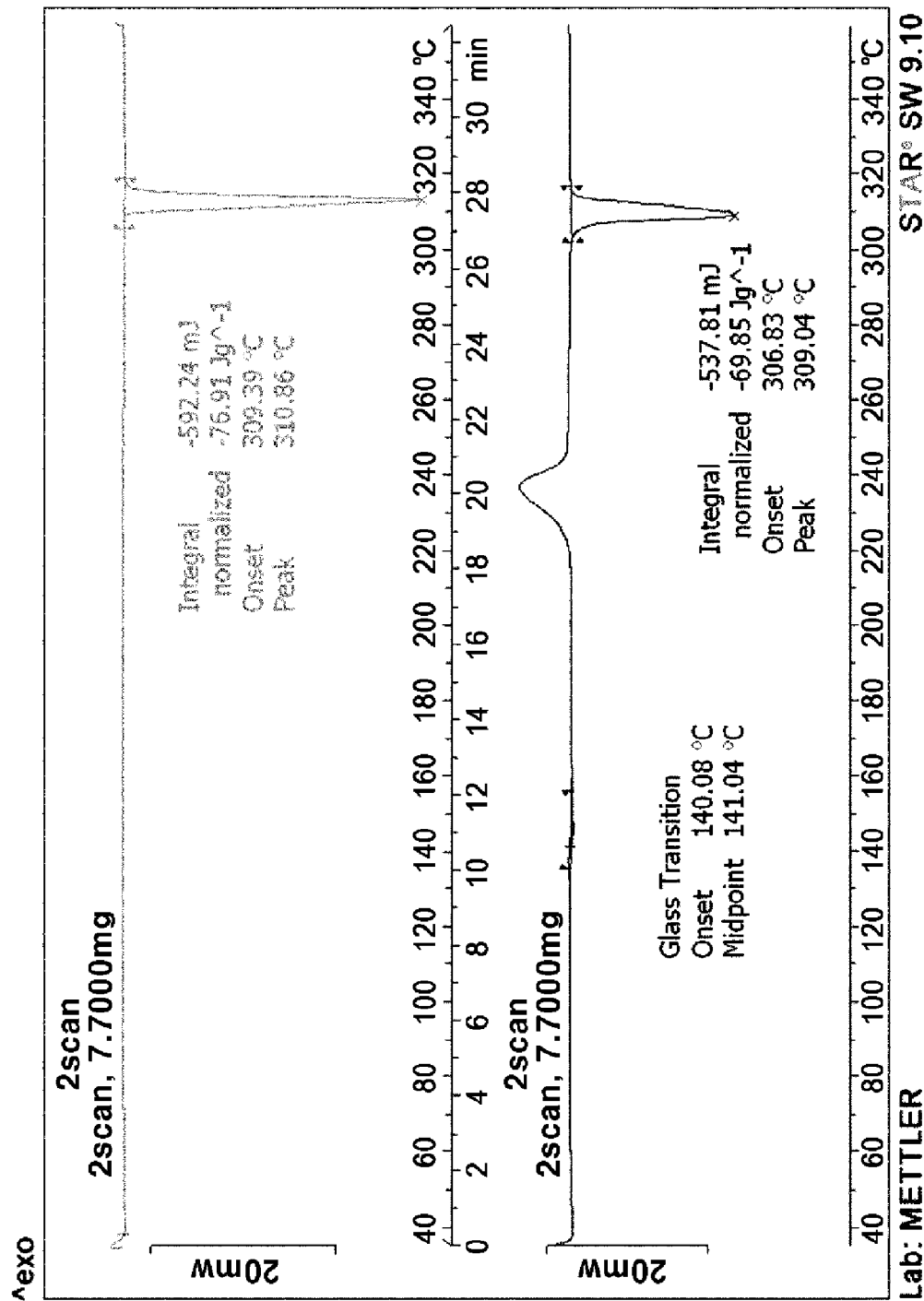
FIG. 8 is a graphic diagram showing the thermal characteristics of a compound of Example 51.
Figure 9:
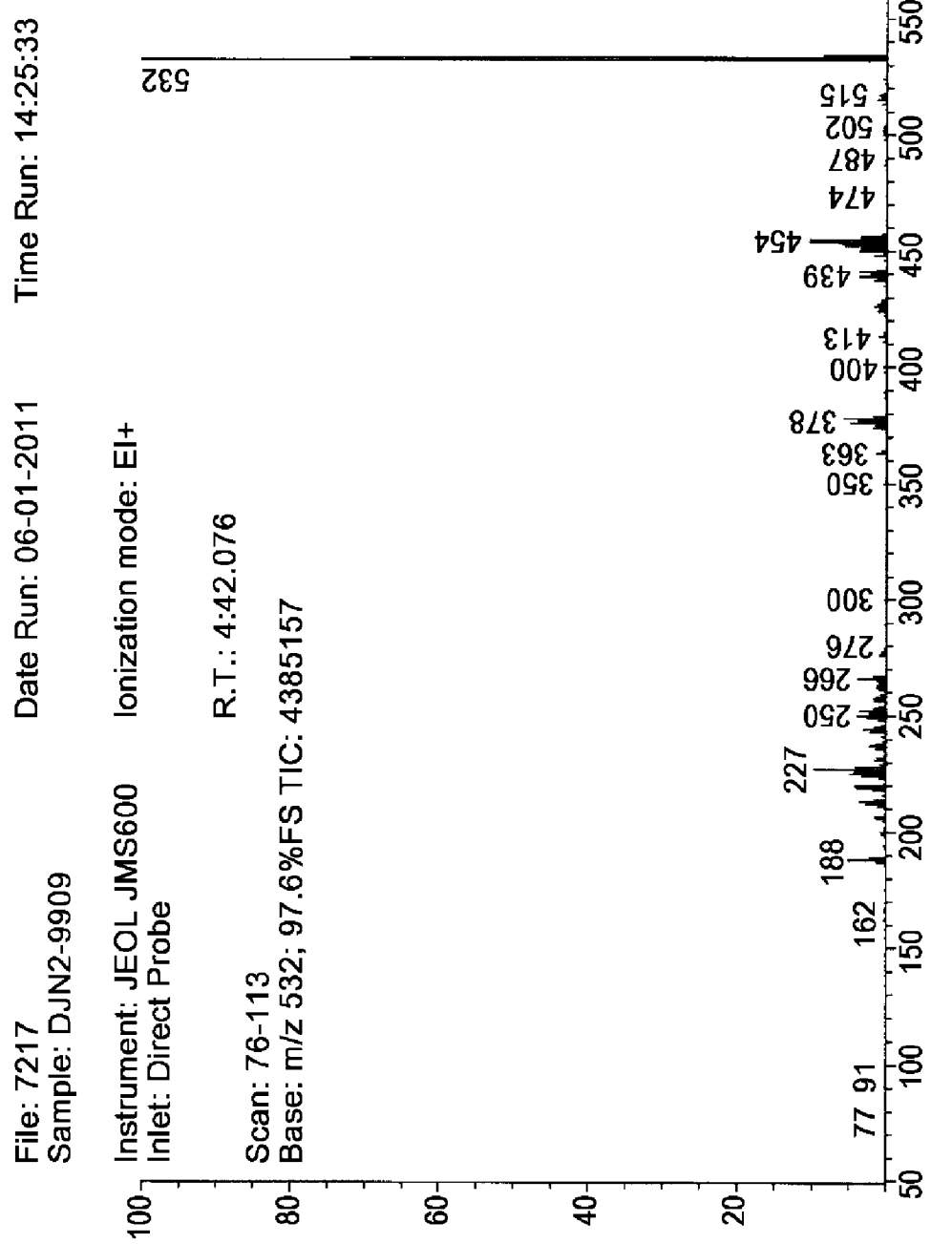
FIG. 9 shows the GC-mass of a compound of Example 51.

In addition, the compound of Example 3 was measured for light absorption and emission characteristics (FIG. 3), thermal characteristics (FIG. 4), GC-mass spectrum (FIG. 5) AND $^1$H-NMR spectrum (FIG. 6).

Examples 4 to 38

Compounds of Examples 4 to 38 were prepared in the same manner as described in Example 3, except that intermediates corresponding to the structures shown in Tables 1 to 9 below were used.

TABLE 1

| Example No. | Chemical structure | $^1$H NMR (CDCl$_3$, 200 MHz) |
|---|---|---|
| 4 | 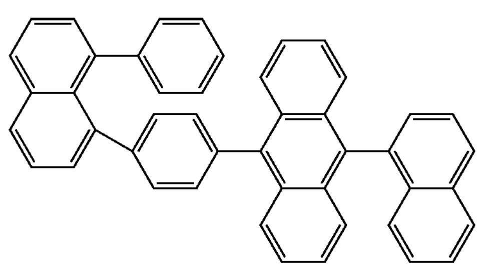 [SMILES: c1ccc(-c2cccc3cccc(-c4ccc(-c5c6ccccc6c(-c6cccc7ccccc67)c6ccccc56)cc4)c23)cc1] | δ 7.12~7.22 (m, 6H), 7.25~7.31 (m, 7H), 7.39~7.43 (m, 2H), 7.46~7.54 (m, 3H), 7.56~7.68 (m, 7H), 7.69~7.71 (t, 1H), 7.99~8.01 (m, 3H), 8.02~8.05 (d, 1H) |
| 5 | 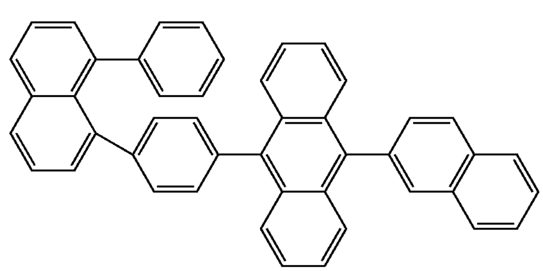 [SMILES: c1ccc(-c2cccc3cccc(-c4ccc(-c5c6ccccc6c(-c6ccc7ccccc7c6)c6ccccc56)cc4)c23)cc1] | δ 7.17~7.22 (m, 4H), 7.27~7.51 (m, 7H), 7.54~7.62 (m, 7H), 7.64~7.80 (m, 3H), 7.85~7.96 (m, 5H), 7.98~8.01 (m, 2H), 7.96~8.02 (d, 2H) |

TABLE 1-continued

| Example No. | Chemical structure | $^1$H NMR (CDCl$_3$, 200 MHz) |
|---|---|---|
| 6 | 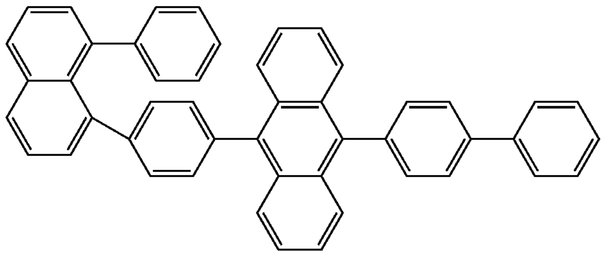 [SMILES: c1ccc(-c2ccc(-c3c4ccccc4c(-c4ccc(-c5cccc6cccc(-c7ccccc7)c56)cc4)c4ccccc34)cc2)cc1] | δ 7.18~7.22 (m, 8H), 7.22~7.41 (m, 7H), 7.54~7.67 (m, 5H), 7.69~7.78 (m, 4H), 7.81~7.92 (m, 6H), 8.01~8.04 (d, 2H) |
| 7 | 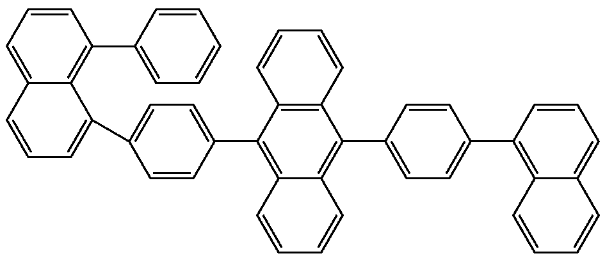 [SMILES: c1ccc(-c2cccc3cccc(-c4ccc(-c5c6ccccc6c(-c6ccc(-c7cccc8ccccc78)cc6)c6ccccc56)cc4)c23)cc1] | δ 7.11~7.22 (m, 7H), 7.23~7.27 (m, 10H), 7.34~7.36 (m, 2H), 7.46~7.54 (m, 3H), 7.54~7.66 (m, 5H), 7.68~7.72 (m, 2H), 7.98~8.02 (m, 3H), 8.04~8.07 (d, 2H) |

TABLE 2

| Example No. | Chemical structure | $^1$H NMR (CDCl$_3$, 200 MHz) |
|---|---|---|
| 8 | 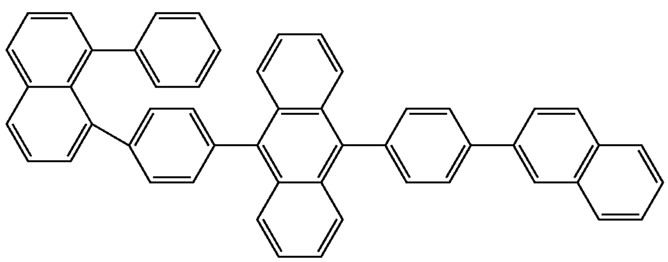 [SMILES: c1ccc(-c2cccc3cccc(-c4ccc(-c5c6ccccc6c(-c6ccc(-c7ccc8ccccc8c7)cc6)c6ccccc56)cc4)c23)cc1] | δ 7.21~7.25 (m, 8H), 7.25~7.47 (m, 7H), 7.58~7.63 (m, 7H), 7.69~7.82 (m, 3H), 7.88~7.94 (m, 5H), 7.99~8.01 (m, 2H), 8.03~8.06 (d, 2H) |
| 9 | 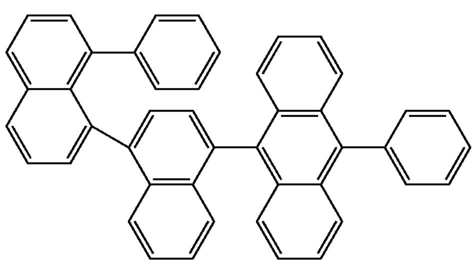 [SMILES: c1ccc(-c2c3ccccc3c(-c3ccc(-c4cccc5cccc(-c6ccccc6)c45)c4ccccc34)c3ccccc23)cc1] | δ 7.14~7.22 (m, 2H), 7.25~7.31 (m, 7H), 7.39~7.43 (m, 6H), 7.46~7.54 (m, 3H), 7.56~7.68 (m, 6H), 7.69~7.71 (m, 2H), 7.99~8.01 (m, 2H), 8.02~8.05 (d, 2H) |
| 10 | 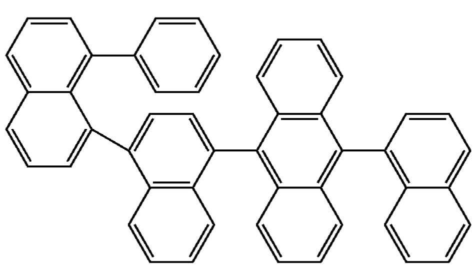 [SMILES: c1ccc(-c2cccc3cccc(-c4ccc(-c5c6ccccc6c(-c6cccc7ccccc67)c6ccccc56)c5ccccc45)c23)cc1] | δ 7.19~7.24 (m, 2H), 7.32~7.44 (m, 7H), 7.48~7.71 (m, 11H), 7.75~7.83 (m, 3H), 7.86~7.92 (m, 7H), 8.04~8.08 (d, 2H) |

TABLE 2-continued

| Example No. | Chemical structure | $^1$H NMR (CDCl$_3$, 200 MHz) |
|---|---|---|
| 11 | 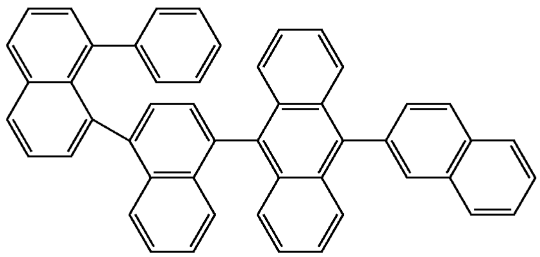 [SMILES: c1ccc(-c2cccc3cccc(-c4ccc(-c5c6ccccc6c(-c6ccc7ccccc7c6)c6ccccc56)c5ccccc45)c23)cc1] | δ 7.17~7.45 (m, 9H), 7.49~7.66 (m, 9H), 7.69~7.76 (m, 3H), 7.83~7.99 (m, 7H), 8.01~8.03 (d, 2H), 8.07~8.10 (d, 2H) |

TABLE 3

| Example No. | Chemical structure | $^1$H NMR (CDCl$_3$, 200 MHz) |
|---|---|---|
| 12 | 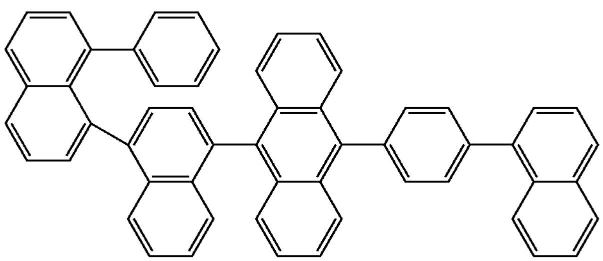 [SMILES: c1ccc(-c2cccc3cccc(-c4ccc(-c5c6ccccc6c(-c6ccc(-c7cccc8ccccc78)cc6)c6ccccc56)c5ccccc45)c23)cc1] | δ 7.13~7.49 (m, 13H), 7.51~7.68 (m, 9H), 7.72~7.79 (m, 5H), 7.86~7.94 (m, 5H), 7.96~8.02 (m, 2H), 8.08~8.11 (d, 2H) |
| 13 | 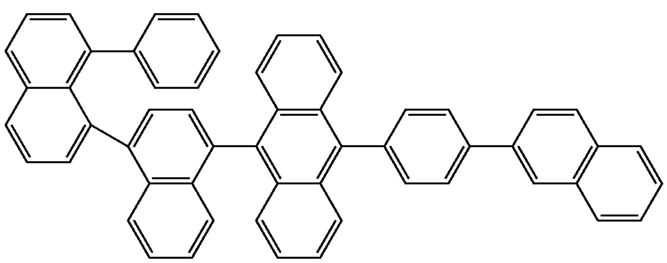 [SMILES: c1ccc(-c2cccc3cccc(-c4ccc(-c5c6ccccc6c(-c6ccc(-c7ccc8ccccc8c7)cc6)c6ccccc56)c5ccccc45)c23)cc1] | δ 7.12~7.47 (m, 13H), 7.51~7.68 (m, 9H), 7.72~7.79 (m, 3H), 7.86~7.94 (m, 5H), 7.96~8.02 (m, 2H), 8.03~8.06 (d, 2H), 8.08~8.11 (d, 2H) |
| 14 | 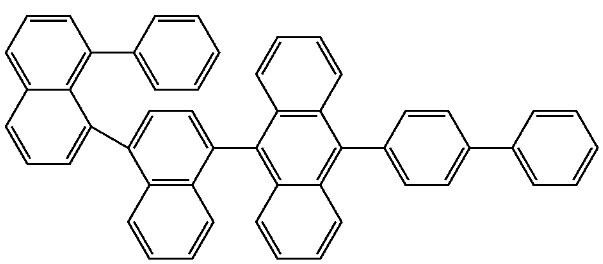 [SMILES: c1ccc(-c2ccc(-c3c4ccccc4c(-c4ccc(-c5cccc6cccc(-c7ccccc7)c56)c5ccccc45)c4ccccc34)cc2)cc1] | δ 7.12~7.24 (m, 4H), 7.32~7.47 (m, 8H), 7.51~7.68 (m, 9H), 7.72~7.79 (m, 3H), 7.86~7.94 (m, 6H), 7.96~8.02 (m, 2H), 8.08~8.11 (d, 2H) |
| 15 | 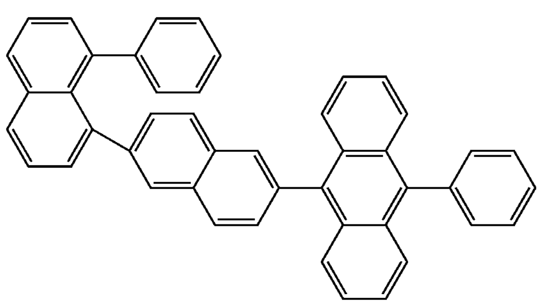 [SMILES: c1ccc(-c2c3ccccc3c(-c3ccc4cc(-c5cccc6cccc(-c7ccccc7)c56)ccc4c3)c3ccccc23)cc1] | δ 7.22~7.29 (m, 3H), 7.31~7.37 (m, 4H), 7.39~7.48 (m, 5H), 7.51~7.67 (m, 6H), 7.72~7.84 (m, 5H), 7.86~7.92 (m, 5H), 8.02~8.05 (d, 2H) |

TABLE 3-continued

| Example No. | Chemical structure | ¹H NMR (CDCl₃, 200 MHz) |
|---|---|---|
| 16 | 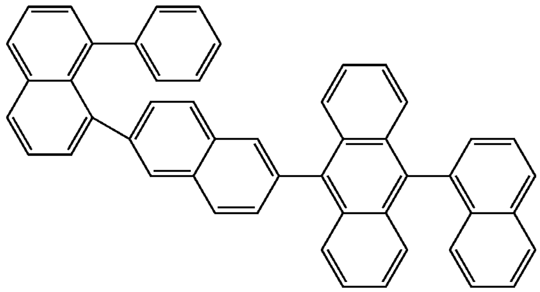 [SMILES: c1ccc(-c2cccc3cccc(-c4ccc5cc(-c6c7ccccc7c(-c7cccc8ccccc78)c7ccccc67)ccc5c4)c23)cc1] | δ 7.22~7.29 (m, 3H), 7.31~7.37 (m, 4H), 7.39~7.48 (m, 5H), 7.51~7.67 (m, 7H), 7.72~7.84 (m, 6H), 7.86~7.92 (m, 5H), 8.02~8.05 (d, 2H) |

TABLE 4

| Example No. | Chemical structure | ¹H NMR (CDCl₃, 200 MHz) |
|---|---|---|
| 17 | 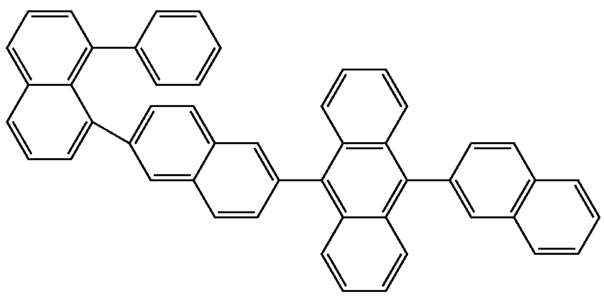 [SMILES: c1ccc(-c2cccc3cccc(-c4ccc5cc(-c6c7ccccc7c(-c7ccc8ccccc8c7)c7ccccc67)ccc5c4)c23)cc1] | δ 7.31~7.48 (m, 7H), 7.53~7.65 (m, 9H), 7.72~7.82 (m, 5H), 7.85~7.92 (m, 7H), 7.95~8.01 (m, 2H), 8.02~8.05 (d, 2H) |
| 18 | 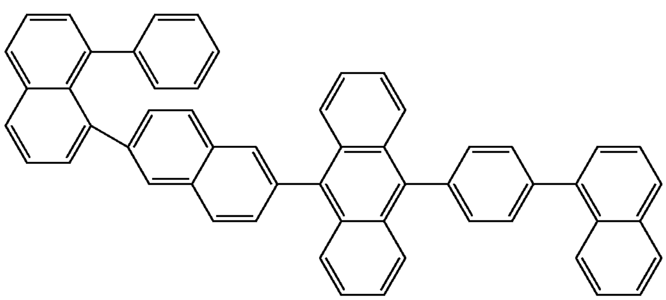 [SMILES: c1ccc(-c2cccc3cccc(-c4ccc5cc(-c6c7ccccc7c(-c7ccc(-c8cccc9ccccc89)cc7)c7ccccc67)ccc5c4)c23)cc1] | δ 7.16~7.25 (m, 4H), 7.30~7.43 (m, 8H), 7.51~7.66 (m, 10H), 7.75~7.84 (m, 6H), 7.86~7.92 (m, 6H), 8.02~8.05 (d, 2H) |
| 19 | 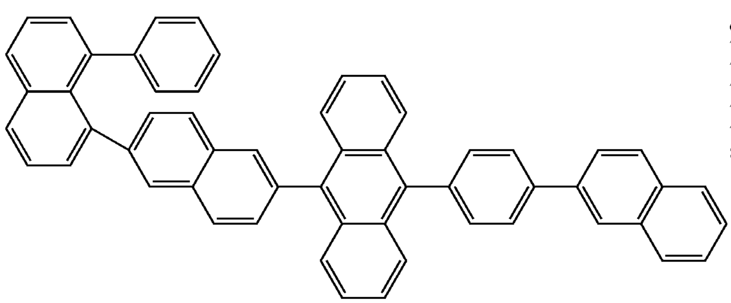 [SMILES: c1ccc(-c2cccc3cccc(-c4ccc5cc(-c6c7ccccc7c(-c7ccc(-c8ccc9ccccc9c8)cc7)c7ccccc67)ccc5c4)c23)cc1] | δ 7.18~7.28 (m, 4H), 7.34~7.48 (m, 7H), 7.57~7.68 (m, 9H), 7.72~7.84 (m, 5H), 7.86~7.92 (m, 7H), 7.99~8.01 (m, 2H), 8.02~8.05 (d, 2H) |

TABLE 5

| Example No. | Chemical structure | $^1$H NMR (CDCl$_3$, 200 MHz) |
|---|---|---|
| 20 | 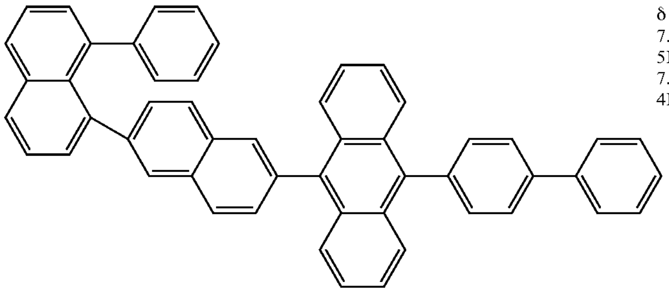 [SMILES: c1ccc(-c2ccc(-c3c4ccccc4c(-c4ccc5cc(-c6cccc7cccc(-c8ccccc8)c67)ccc5c4)c4ccccc34)cc2)cc1] | δ 7.18~7.24 (m, 4H), 7.30~7.44 (m, 6H), 7.48~7.52 (m, 5H), 7.55~7.67 (m, 7H), 7.75~7.84 (m, 6H), 7.86~7.92 (m, 4H), 8.01~8.04 (m, 2H) |
| 21 | 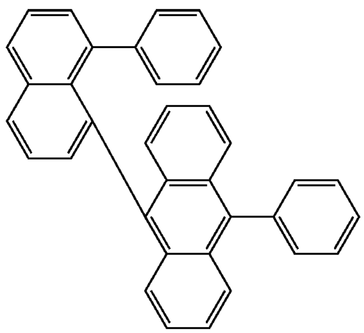 [SMILES: c1ccc(-c2c3ccccc3c(-c3cccc4cccc(-c5ccccc5)c34)c3ccccc23)cc1] | δ 7.13~7.26 (m, 2H), 7.33~7.42 (m, 2H), 7.48~7.57 (m, 5H), 7.64~7.79 (m, 7H), 7.82~7.94 (m, 6H), 8.03~8.09 (m, 2H) |
| 22 | 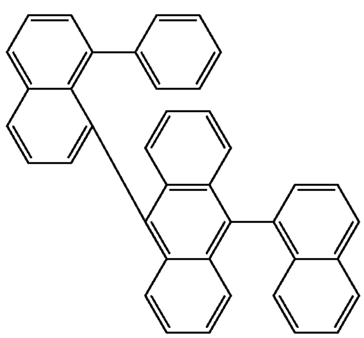 [SMILES: c1ccc(-c2cccc3cccc(-c4c5ccccc5c(-c5cccc6ccccc56)c5ccccc45)c23)cc1] | δ 7.13~7.26 (m, 2H), 7.33~7.46 (m, 3H), 7.51~7.62 (m, 6H), 7.69~7.82 (m, 7H), 7.84~7.96 (m, 6H), 8.03~8.09 (m, 2H) |
| 23 | 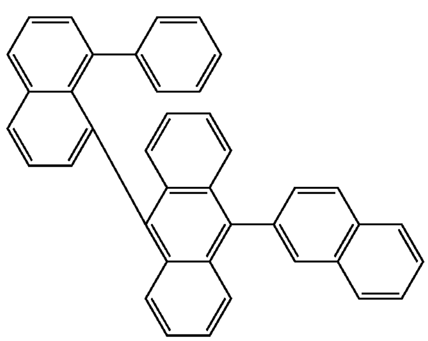 [SMILES: c1ccc(-c2cccc3cccc(-c4c5ccccc5c(-c5ccc6ccccc6c5)c5ccccc45)c23)cc1] | δ 7.18~7.27 (m, 2H), 7.35~7.45 (m, 4H), 7.53~7.65 (m, 7H), 7.75~7.83 (m, 4H), 7.84~7.90 (m, 5H), 7.94~8.02 (m, 2H), 8.04~8.10 (m, 2H) |

TABLE 5-continued

| Example No. | Chemical structure | ¹H NMR (CDCl₃, 200 MHz) |
|---|---|---|
| 24 | 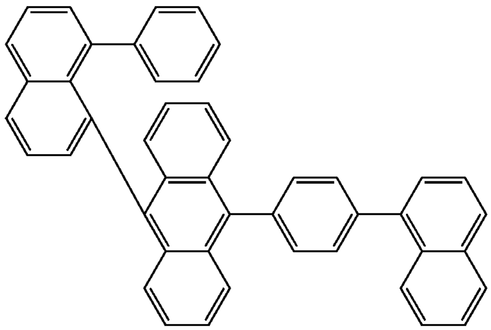 [SMILES: c1ccc(-c2cccc3cccc(-c4c5ccccc5c(-c5ccc(-c6cccc7ccccc67)cc5)c5ccccc45)c23)cc1] | δ 7.13~7.26 (m, 4H), 7.33~7.46 (m, 5H), 7.51~7.62 (m, 6H), 7.69~7.82 (m, 7H), 7.84~7.96 (m, 6H), 8.03~8.09 (m, 2H) |

TABLE 6

| Example No. | Chemical structure | ¹H NMR (CDCl₃, 200 MHz) |
|---|---|---|
| 25 | 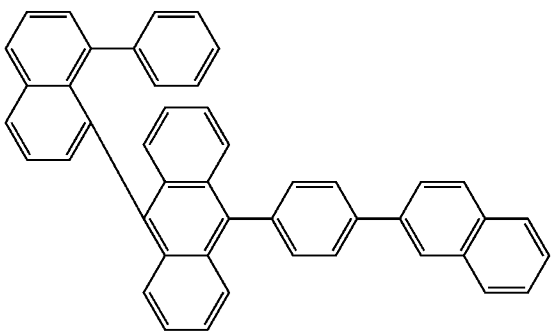 [SMILES: c1ccc(-c2cccc3cccc(-c4c5ccccc5c(-c5ccc(-c6ccc7ccccc7c6)cc5)c5ccccc45)c23)cc1] | δ 7.15~7.27 (m, 4H), 7.34~7.48 (m, 6H), 7.56~7.65 (m, 7H), 7.72~7.81 (m, 4H), 7.87~7.92 (m, 5H), 7.96~8.04 (m, 2H), 8.07~8.12 (m, 2H) |
| 26 | 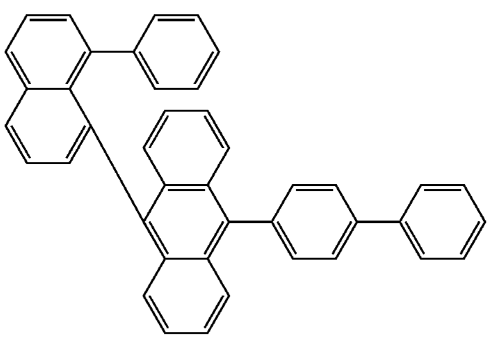 [SMILES: c1ccc(-c2ccc(-c3c4ccccc4c(-c4cccc5cccc(-c6ccccc6)c45)c4ccccc34)cc2)cc1] | δ 7.18~7.27 (m, 4H), 7.39~7.56 (m, 10H), 7.61~7.66 (m, 4H), 7.75~7.81 (m, 4H), 7.84~7.91 (m, 4H), 8.04~8.10 (m, 2H) |
| 27 | 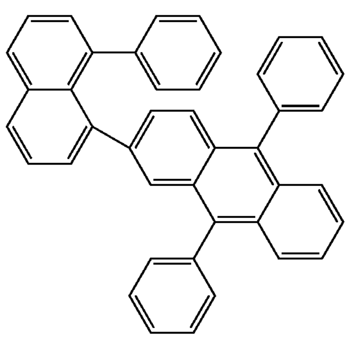 [SMILES: c1ccc(-c2c3ccccc3c(-c3ccccc3)c3cc(-c4cccc5cccc(-c6ccccc6)c45)ccc23)cc1] | δ 7.31~7.43 (m, 4H), 7.45~7.57 (m, 7H), 7.59~7.73 (m, 6H), 7.75~7.83 (m, 5H), 7.91~7.97 (m, 2H), 8.02~8.10 (m, 2H), 8.14~8.20 (m, 2H) |

TABLE 7

| Example No. | Chemical structure | ¹H NMR (CDCl₃, 200 MHz) |
|---|---|---|
| 28 | 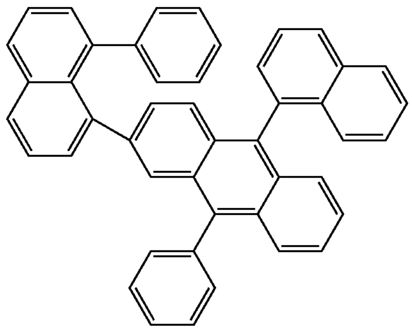 [SMILES: c1ccc(-c2c3ccccc3c(-c3cccc4ccccc34)c3ccc(-c4cccc5cccc(-c6ccccc6)c45)cc23)cc1] | δ 7.27~7.42 (m, 4H), 7.50~7.64 (m, 6H), 7.67~7.76 (m, 9H), 7.77~7.82 (m, 4H), 7.87~7.98 (m, 5H), 8.13~8.20 (m, 2H) |
| 29 | 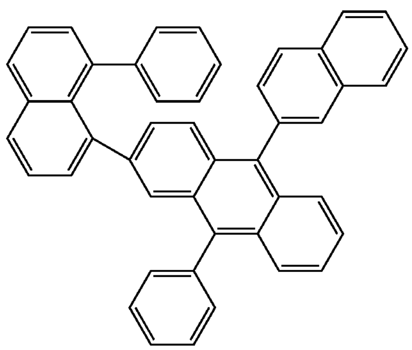 [SMILES: c1ccc(-c2c3ccccc3c(-c3ccc4ccccc4c3)c3ccc(-c4cccc5cccc(-c6ccccc6)c45)cc23)cc1] | δ 7.30~7.44 (m, 4H), 7.50~7.63 (m, 7H), 7.69~7.80 (m, 10H), 7.85~7.97 (m, 5H), 8.03~8.09 (m, 2H), 8.17~8.23 (m, 2H) |
| 30 | 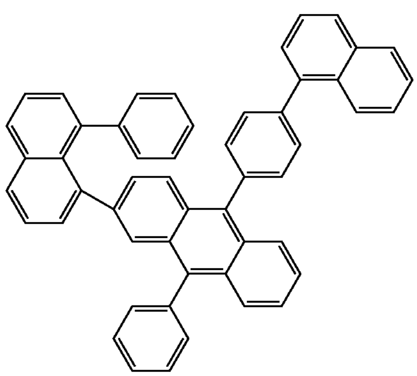 [SMILES: c1ccc(-c2c3ccccc3c(-c3ccc(-c4cccc5ccccc45)cc3)c3ccc(-c4cccc5cccc(-c6ccccc6)c45)cc23)cc1] | δ 7.19~7.26 (m, 4H), 7.33~7.48 (m, 8H), 7.54~7.83 (m, 15H), 7.84~7.95 (m, 5H), 8.19~8.24 (m, 2H) |
| 31 | 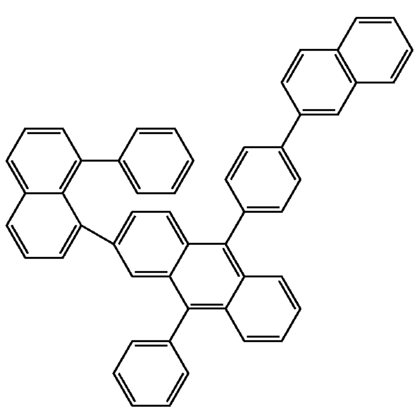 [SMILES: c1ccc(-c2c3ccccc3c(-c3ccc(-c4ccc5ccccc5c4)cc3)c3ccc(-c4cccc5cccc(-c6ccccc6)c45)cc23)cc1] | δ 7.18~7.25 (m, 4H), 7.37~7.51 (m, 8H), 7.57~7.82 (m, 13H), 7.86~7.97 (m, 5H), 8.04~8.11 (m, 2H), 8.19~8.24 (m, 2H) |

TABLE 7-continued

| Example No. | Chemical structure | $^1$H NMR (CDCl$_3$, 200 MHz) |
|---|---|---|
| 32 | 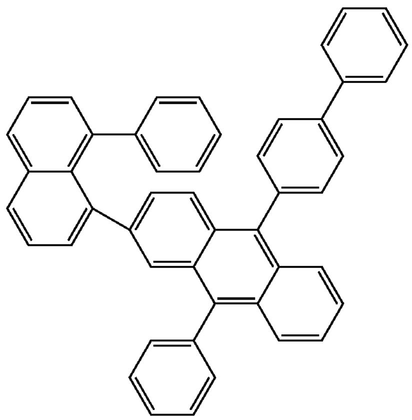 [SMILES: c1ccc(-c2ccc(-c3c4ccccc4c(-c4ccccc4)c4cc(-c5cccc6cccc(-c7ccccc7)c56)ccc34)cc2)cc1] | δ 7.20~7.26 (m, 4H), 7.37~7.53 (m, 11H), 7.59~7.77 (m, 7H), 7.78~7.85 (m, 4H), 7.89~7.93 (m, 2H), 8.03~8.11 (m, 2H), 8.18~8.22 (m, 2H) |

TABLE 8

| Example No. | Chemical structure | $^1$H NMR (CDCl$_3$, 200 MHz) |
|---|---|---|
| 33 | 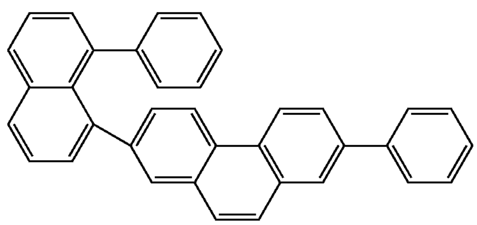 [SMILES: c1ccc(-c2ccc3c(ccc4cc(-c5cccc6cccc(-c7ccccc7)c56)ccc43)c2)cc1] | δ 7.32~7.46 (m, 6H), 7.58~7.65 (m, 4H), 7.71~7.86 (m, 6H), 7.93~8.02 (m, 2H), 8.23~8.34 (m, 4H), 8.57~8.66 (m, 2H) |
| 34 | 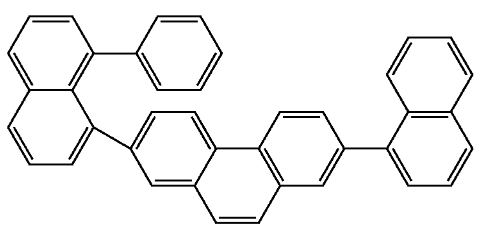 [SMILES: c1ccc(-c2cccc3cccc(-c4ccc5c(ccc6cc(-c7cccc8ccccc78)ccc65)c4)c23)cc1] | δ 7.27~7.38 (m, 3H), 7.48~7.70 (m, 8H), 7.70~7.82 (m, 6H), 7.87~7.96 (m, 3H), 8.20~8.32 (m, 4H), 8.53~8.64 (m, 2H) |
| 35 | 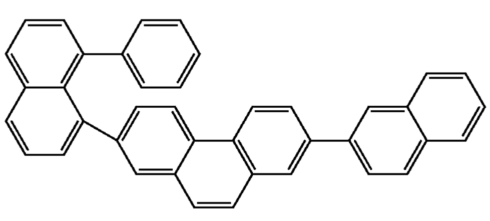 [SMILES: c1ccc(-c2cccc3cccc(-c4ccc5c(ccc6cc(-c7ccc8ccccc8c7)ccc65)c4)c23)cc1] | δ 7.32~7.42 (m, 3H), 7.61~7.83 (m, 12H), 7.87~7.93 (m, 2H), 7.94~8.06 (m, 3H), 8.22~8.33 (m, 4H), 8.57~8.67 (m, 2H) |

TABLE 9

| Example No. | Chemical structure | $^1$H NMR (CDCl$_3$, 200 MHz) |
|---|---|---|
| 36 | 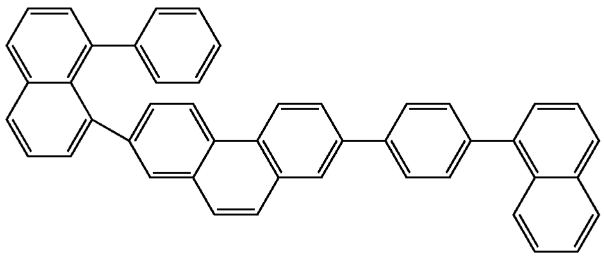 [SMILES: c1ccc(-c2cccc3cccc(-c4ccc5c(ccc6cc(-c7ccc(-c8cccc9ccccc89)cc7)ccc65)c4)c23)cc1] | δ 7.18~7.23 (m, 4H), 7.33~7.41 (m, 3H), 7.53~7.74 (m, 8H), 7.76~7.82 (m, 6H), 7.89~8.00 (m, 3H), 8.22~8.33 (m, 4H), 8.58~8.67 (m, 2H) |
| 37 | 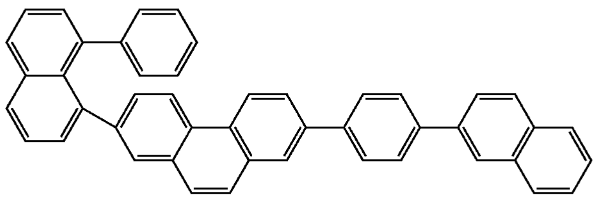 [SMILES: c1ccc(-c2cccc3cccc(-c4ccc5c(ccc6cc(-c7ccc(-c8ccc9ccccc9c8)cc7)ccc65)c4)c23)cc1] | δ 7.20~7.26 (m, 4H), 7.37~7.45 (m, 3H), 7.56~7.79 (m, 12H), 7.85~7.91 (m, 2H), 7.94~8.04 (m, 3H), 8.24~8.36 (m, 4H), 8.62~8.71 (m, 2H) |
| 38 | 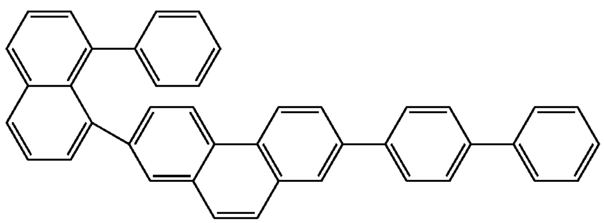 [SMILES: c1ccc(-c2ccc(-c3ccc4c(ccc5cc(-c6cccc7cccc(-c8ccccc8)c67)ccc54)c3)cc2)cc1] | δ 7.22~7.28 (m, 4H), 7.39~7.49 (m, 6H), 7.58~7.65 (m, 4H), 7.74~7.88 (m, 6H), 7.94~8.04 (m, 2H), 8.27~8.37 (m, 4H), 8.60~8.70 (m, 2H) |

Example 39

A compound of Example 39 was prepared according to the following preparation method.

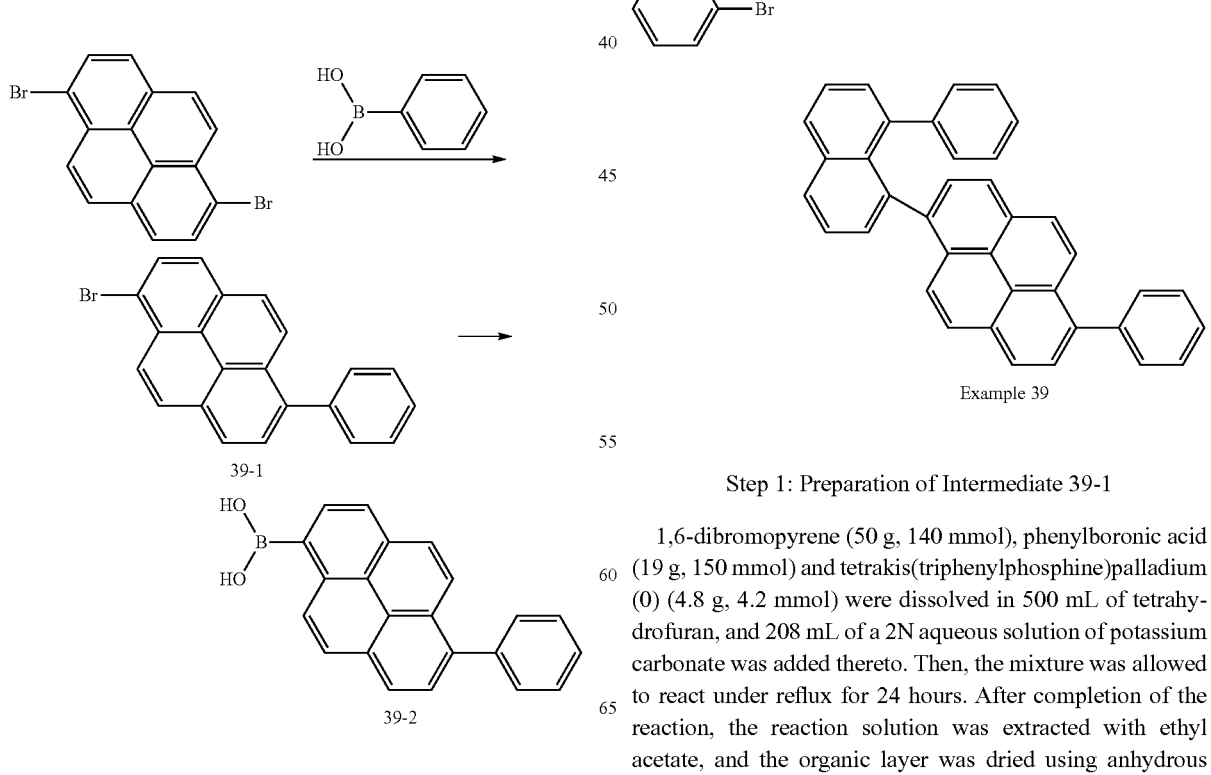

Step 1: Preparation of Intermediate 39-1

1,6-dibromopyrene (50 g, 140 mmol), phenylboronic acid (19 g, 150 mmol) and tetrakis(triphenylphosphine)palladium (0) (4.8 g, 4.2 mmol) were dissolved in 500 mL of tetrahydrofuran, and 208 mL of a 2N aqueous solution of potassium carbonate was added thereto. Then, the mixture was allowed to react under reflux for 24 hours. After completion of the reaction, the reaction solution was extracted with ethyl acetate, and the organic layer was dried using anhydrous magnesium sulfate, and then purified through a hexane column, thereby obtaining intermediate 39-1 at a yield of 69% (34 g).

Step 2: Preparation of Intermediate 39-2

Intermediate 39-1 (50 g, 140 mmol) was dissolved in 1000 mL of tetrahydrofuran under an argon atmosphere, and 1.6 M n-butyl lithium (96 mL) was added thereto at −78° C., followed by stirring for about 1 hour. Triethyl borate (29 mL, 170 mmol) was slowly added dropwise thereto at the same temperature, and the solution was stirred for 2 hours, followed by stirring at room temperature for 12 hours. After completion of the reaction, the reaction solution was extracted with ethyl acetate, and the organic layer was dried using anhydrous magnesium sulfate, and then purified through a dichloromethane column, thereby obtaining intermediate 39-2 at a yield of 75% (34 g).

Step 3: Preparation of Compound of Example 39

Intermediate 3-1 (10 g, 35 mmol) of Example 3, intermediate 39-2 (14 g, 42 mmol) and tetrakis(triphenylphosphine) palladium(0) (1.2 g, 1.1 mmol) were dissolved in 1000 mL of tetrahydrofuran, and 54 mL of a 2N aqueous solution of potassium carbonate was added thereto. Then, the mixture was allowed to react under reflux for 24 hours. After completion of the reaction, the reaction solution was extracted with ethyl acetate, and the organic layer was dried using anhydrous magnesium sulfate, and then purified through a hexane column, thereby obtaining a compound of Example 39 at a yield of 58% (11 g).

$^1$H-NMR (200 MHz, CDCl$_3$): δ 7.31-7.44 (m, 6H), 7.49-7.60 (m, 5H), 7.63-7.80 (m, 7H), 7.84-7.95 (m, 4H), 8.20-8.30 (m, 2H)

Examples 40 to 48

Compounds of Examples 40 to 48 were prepared in the same manner as described in Example 3, except that intermediates corresponding to the structures shown in Tables 10 and 11 below were used.

TABLE 10

| Example No. | Chemical structure | $^1$H NMR (CDCl$_3$, 200 MHz) |
|---|---|---|
| 40 | 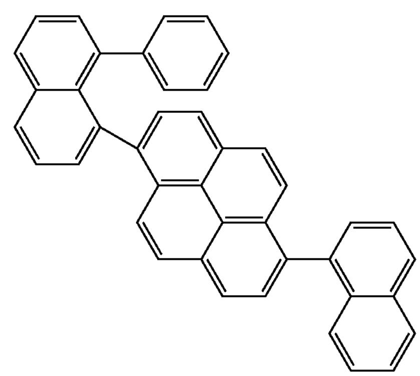 [SMILES: c1ccc(-c2cccc3cccc(-c4ccc5ccc6c(-c7cccc8ccccc78)ccc7ccc4c5c76)c23)cc1] | δ 7.31~7.39 (m, 3H), 7.45~7.68 (m, 8H), 7.72~7.85 (m, 6H), 7.88~8.05 (m, 5H), 8.20~8.29 (m, 2H) |
| 41 | 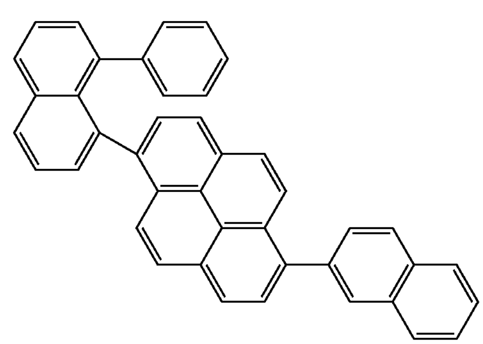 [SMILES: c1ccc(-c2cccc3cccc(-c4ccc5ccc6c(-c7ccc8ccccc8c7)ccc7ccc4c5c76)c23)cc1] | δ 7.32~7.44 (m, 4H), 7.47~7.58 (m, 5H), 7.62~7.80 (m, 8H), 7.85~7.97 (m, 5H), 8.04~8.16 (m, 2H), 8.18~8.26 (m, 2H) |

TABLE 10-continued

| Example No. | Chemical structure | $^1$H NMR (CDCl$_3$, 200 MHz) |
|---|---|---|
| 42 | 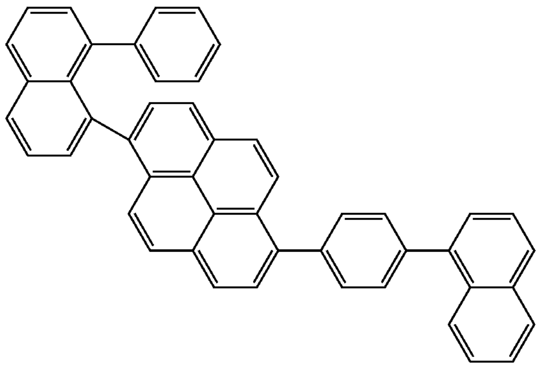 [SMILES: c1ccc(-c2cccc3cccc(-c4ccc5ccc6c(-c7ccc(-c8cccc9ccccc89)cc7)ccc7ccc4c5c76)c23)cc1] | δ 7.21~7.30 (m, 4H), 7.34~7.44 (m, 2H), 7.45~7.56 (m, 7H), 7.61~7.84 (m, 10H), 7.88~8.03 (m, 5H), 8.18~8.27 (m, 2H) |
| 43 | 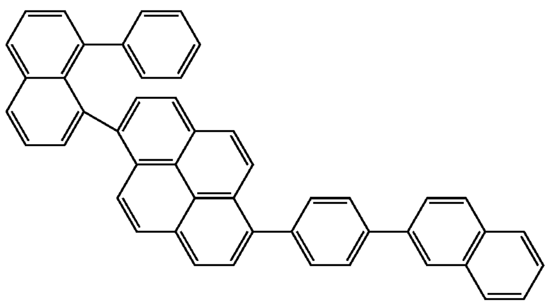 [SMILES: c1ccc(-c2cccc3cccc(-c4ccc5ccc6c(-c7ccc(-c8ccc9ccccc9c8)cc7)ccc7ccc4c5c76)c23)cc1] | δ 7.18~7.28 (m, 4H), 7.32~7.44 (m, 3H), 7.47~7.58 (m, 6H), 7.64~7.82 (m, 8H), 7.86~7.99 (m, 5H), 8.02~8.18 (m, 2H), 8.20~8.30 (m, 2H) |
| 44 | 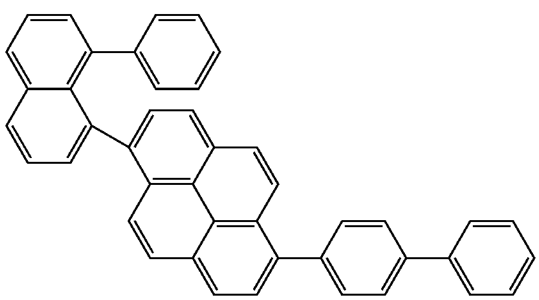 [SMILES: c1ccc(-c2ccc(-c3ccc4ccc5c(-c6cccc7cccc(-c8ccccc8)c67)ccc6ccc3c4c65)cc2)cc1] | δ 7.22~7.31 (m, 4H), 7.35~7.47 (m, 6H), 7.53~7.78 (m, 12H), 7.82~7.96 (m, 4H), 8.22~8.33 (m, 2H) |

TABLE 11

| Example No. | Chemical structure | $^1$H NMR (CDCl$_3$, 200 MHz) |
|---|---|---|
| 45 | 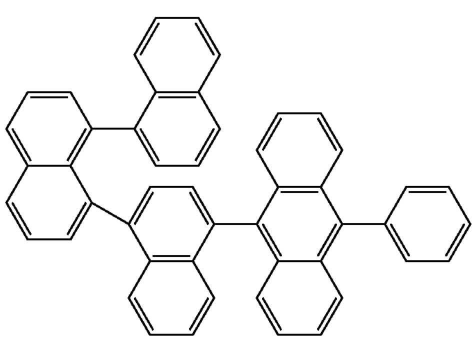 [SMILES: c1ccc(-c2c3ccccc3c(-c3ccc(-c4cccc5cccc(-c6cccc7ccccc67)c45)c4ccccc34)c3ccccc23)cc1] | δ 7.24~7.49 (m, 11H), 7.54~7.73 (m, 11H), 7.85~7.94 (m, 4H), 8.19~8.29 (m, 3H), 8.41~8.51 (m, 3H) |

TABLE 11-continued
| Example No. | Chemical structure | $^1$H NMR (CDCl$_3$, 200 MHz) |
|---|---|---|
| 46 | 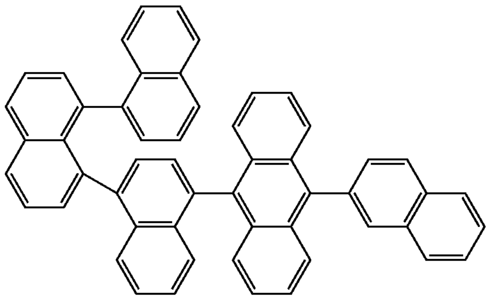 [SMILES: c1ccc2cc(-c3c4ccccc4c(-c4ccc(-c5cccc6cccc(-c7cccc8ccccc78)c56)c5ccccc45)c4ccccc34)ccc2c1] | δ 7.26~7.46 (m, 8H), 7.58~7.78 (m, 13H), 7.83~7.93 (m, 5H), 8.04~8.15 (m, 2H), 8.22~8.33 (m, 3H), 8.42~8.51 (m, 3H) |
| 47 | 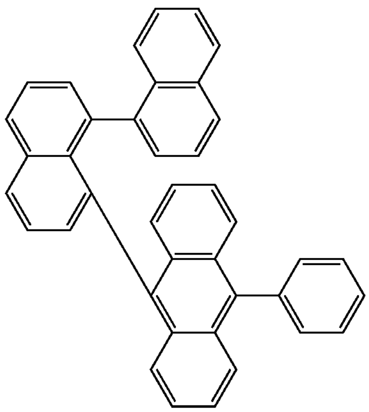 [SMILES: c1ccc(-c2c3ccccc3c(-c3cccc4cccc(-c5cccc6ccccc56)c34)c3ccccc23)cc1] | δ 7.23~7.45 (m, 9H), 7.56~7.77 (m, 9H), 7.88~7.95 (m, 4H), 8.27~8.39 (m, 4H) |
| 48 | 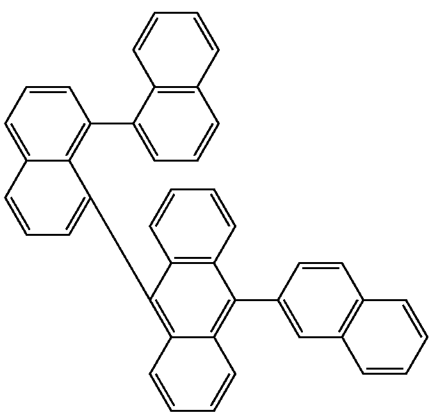 [SMILES: c1ccc2cc(-c3c4ccccc4c(-c4cccc5cccc(-c6cccc7ccccc67)c45)c4ccccc34)ccc2c1] | δ 7.27~7.48 (m, 6H), 7.54~7.72 (m, 11H), 7.86~7.95 (m, 5H), 8.01~8.13 (m, 2H), 8.25~8.38 (m, 4H) |
Example 49
A compound of Example 49 was prepared according to the following preparation method.
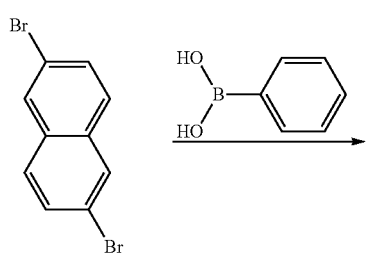
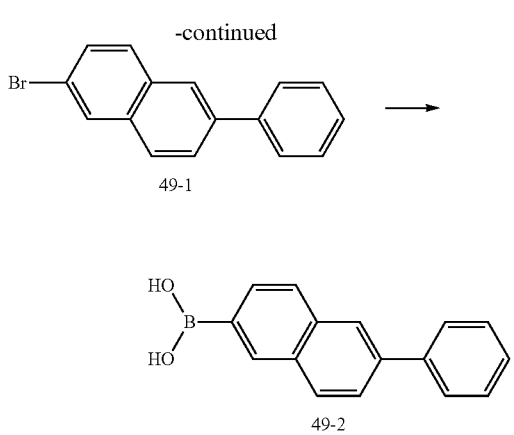

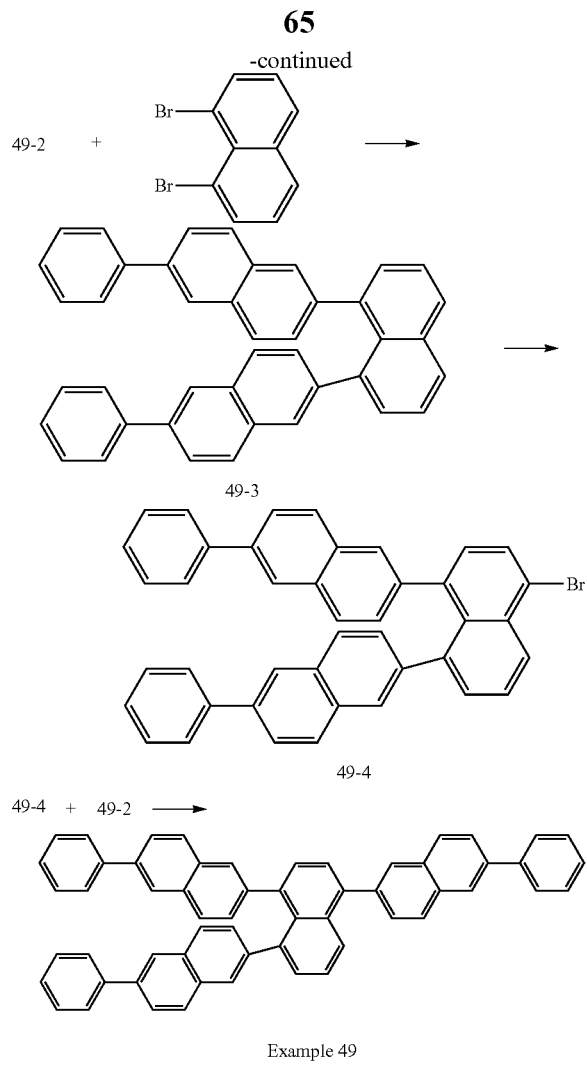

Example 49

Step 1: Preparation of Intermediate 49-1

2,6-dibromonaphthalene (50 g, 170 mmol), phenylboronic acid (23 g, 190 mmol) and tetrakis(triphenylphosphine)palladium(0) (6.1 g, 10 mmol) were dissolved in 500 mL of tetrahydrofuran, and 260 mL of a 2N aqueous solution of potassium carbonate was added thereto. Then, the mixture was allowed to react under reflux for 24 hours. After completion of the reaction, the reaction solution was extracted with ethyl acetate, and the organic layer was dried using anhydrous magnesium sulfate, and then purified through a hexane column, thereby obtaining intermediate 49-1 at a yield of 75% (37 g).

Step 2: Preparation of Intermediate 49-2

Intermediate 49-1 (50 g, 180 mmol) was dissolved in 1000 mL of tetrahydrofuran under an argon atmosphere, and 1.6 M n-butyl lithium (121 mL) was added thereto at −78° C., followed by stirring for 1 hour. Triethyl borate (36 mL, 210 mmol) was slowly added dropwise thereto at the same temperature, and the solution was stirred for 2 hours, followed by stirring at room temperature for 12 hours. After completion of the reaction, the reaction solution was extracted with ethyl acetate, and the organic layer was dried using anhydrous magnesium sulfate, and then purified through a dichloromethane column, thereby obtaining intermediate 49-2 at a yield of 78% (34 g).

Step 3: Preparation of Intermediate 49-3

1,8-dibromonaphthalene (10 g, 30 mmol), intermediate 49-2 (20 g, 80 mmol) and tetrakis(triphenylphosphine)palladium(0) (2 g, 1.7 mmol) were dissolved in 500 mL of tetrahydrofuran, and 70 mL of a 2N aqueous solution of potassium carbonate was added thereto. Then, the mixture was allowed to react under reflux for 24 hours. After completion of the reaction, the reaction solution was extracted with ethyl acetate, and the organic layer was dried using anhydrous magnesium sulfate, and then purified through a hexane column, thereby obtaining intermediate 49-3 at a yield of 70% (13 g).

Step 4: Preparation of Intermediate 49-4

Intermediate 49-3 (50 g, 94 mmol) was dissolved in 1000 mL of chloroform, and bromine (16 g, 103 mmol) was slowly added dropwise thereto. The mixture was allowed to react at room temperature for 6 hours, and then neutralized with an aqueous solution of caustic soda. The organic layer was separated, dried using anhydrous magnesium sulfate, and then recrystallized from toluene, thereby obtaining intermediate 49-4 at a yield of 91% (52 g).

Step 5: Preparation of Compound of Example 49

Intermediate 49-4 (10 g, 16 mmol), intermediate 49-2 (5.3 g, 21 mmol) and tetrakis(triphenylphosphine)palladium(0) (0.6 g, 0.5 mmol) were dissolved in 150 mL of tetrahydrofuran, and 25 mL of a 2N aqueous solution of potassium carbonate was added thereto. Then, the mixture was allowed to react under reflux for 24 hours. After completion of the reaction, the reaction solution was extracted with ethyl acetate, and the organic layer was dried using anhydrous magnesium sulfate, and then purified through a hexane column, thereby obtaining a compound of Example 49 at a yield of 70% (7 g).

$^1$H-NMR (200 MHz, CDCl$_3$): δ 7.35-7.53 (m, 10H), 7.56-7.62 (m, 8H), 7.71-7.83 (m, 12H), 7.90-7.96 (m, 6H), 8.35-8.47 (m, 2H)

Example 50

The following compound was prepared in the same manner as described in Example 49, except that 1,6'-binaphthyl-2'-ylboronic acid was used instead of intermediate 49-2.

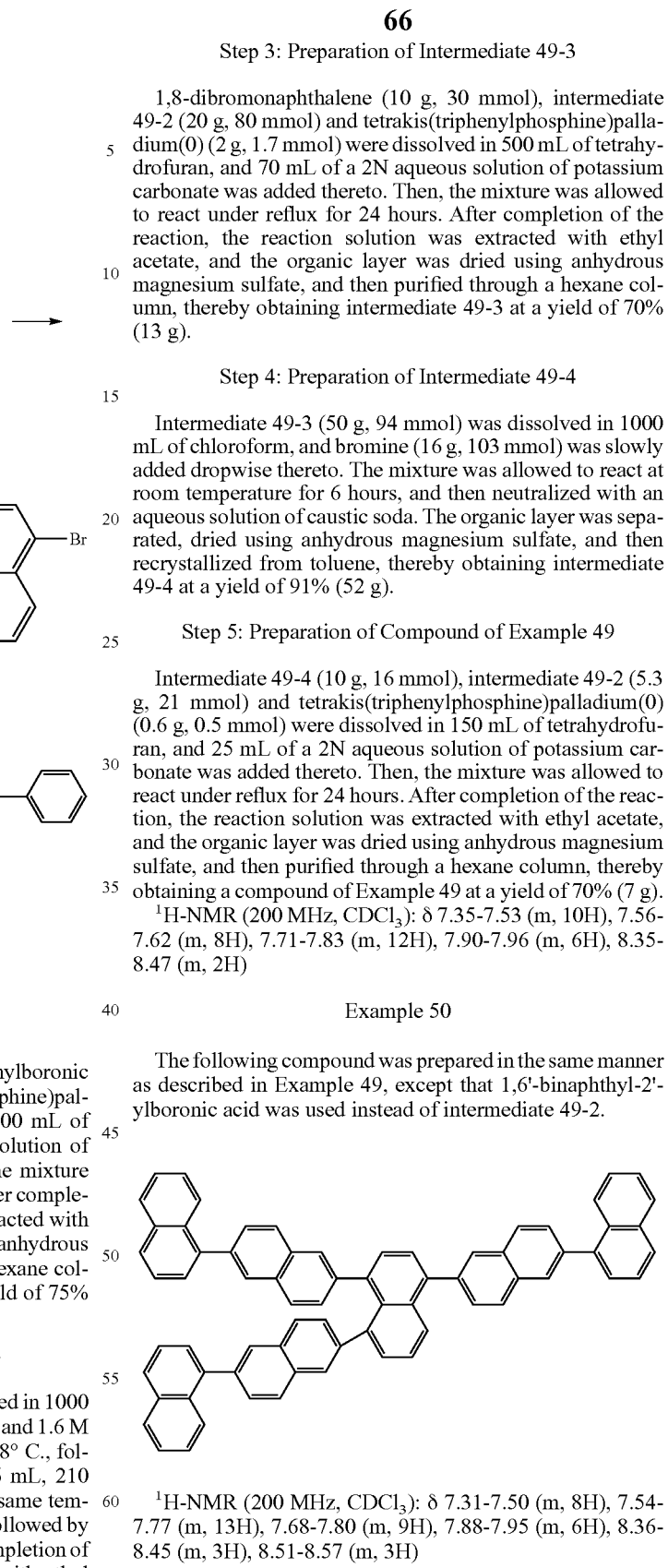

$^1$H-NMR (200 MHz, CDCl$_3$): δ 7.31-7.50 (m, 8H), 7.54-7.77 (m, 13H), 7.68-7.80 (m, 9H), 7.88-7.95 (m, 6H), 8.36-8.45 (m, 3H), 8.51-8.57 (m, 3H)

Example 51

A compound of Example 51 was prepared according to the following preparation method.

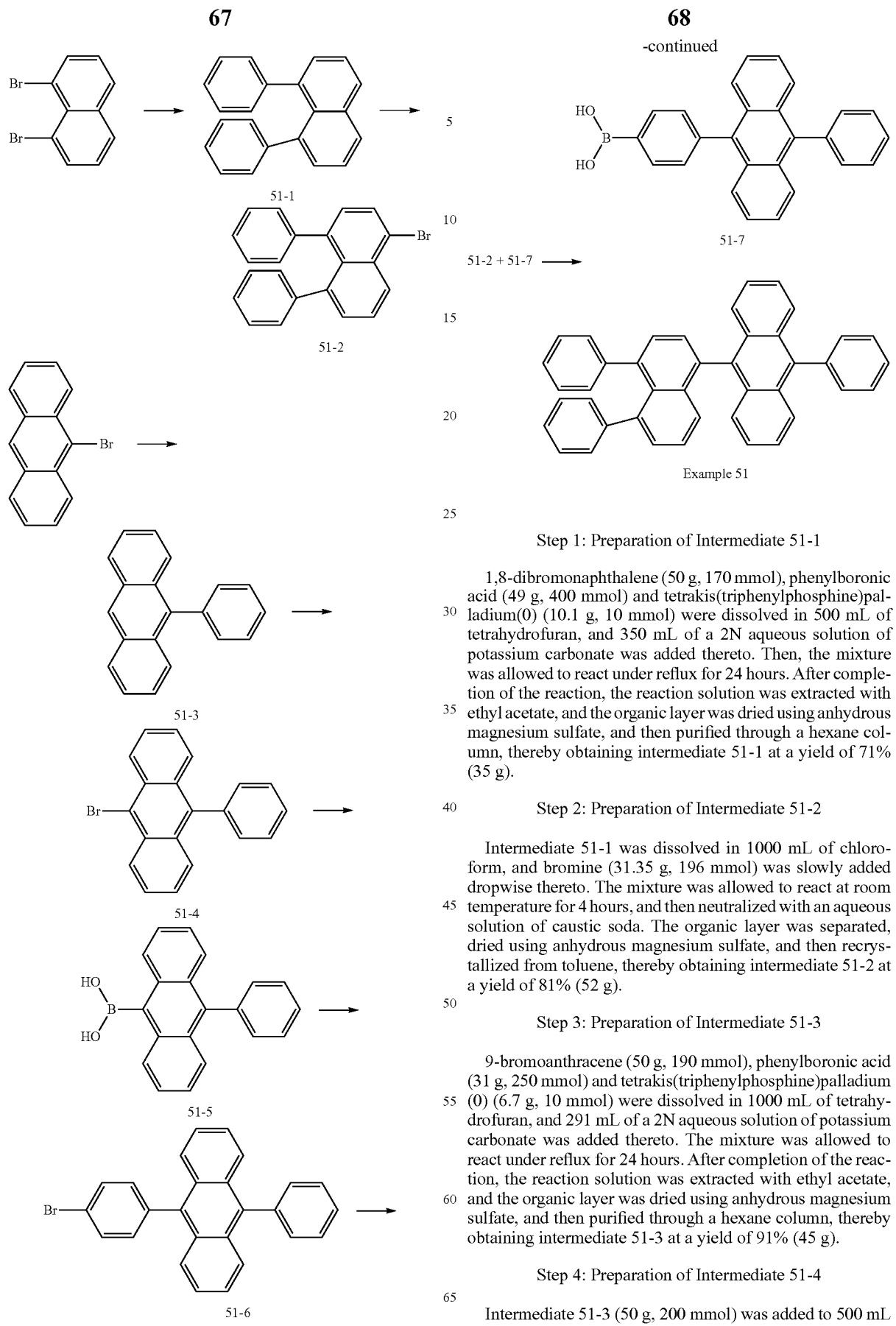

Step 1: Preparation of Intermediate 51-1

1,8-dibromonaphthalene (50 g, 170 mmol), phenylboronic acid (49 g, 400 mmol) and tetrakis(triphenylphosphine)palladium(0) (10.1 g, 10 mmol) were dissolved in 500 mL of tetrahydrofuran, and 350 mL of a 2N aqueous solution of potassium carbonate was added thereto. Then, the mixture was allowed to react under reflux for 24 hours. After completion of the reaction, the reaction solution was extracted with ethyl acetate, and the organic layer was dried using anhydrous magnesium sulfate, and then purified through a hexane column, thereby obtaining intermediate 51-1 at a yield of 71% (35 g).

Step 2: Preparation of Intermediate 51-2

Intermediate 51-1 was dissolved in 1000 mL of chloroform, and bromine (31.35 g, 196 mmol) was slowly added dropwise thereto. The mixture was allowed to react at room temperature for 4 hours, and then neutralized with an aqueous solution of caustic soda. The organic layer was separated, dried using anhydrous magnesium sulfate, and then recrystallized from toluene, thereby obtaining intermediate 51-2 at a yield of 81% (52 g).

Step 3: Preparation of Intermediate 51-3

9-bromoanthracene (50 g, 190 mmol), phenylboronic acid (31 g, 250 mmol) and tetrakis(triphenylphosphine)palladium (0) (6.7 g, 10 mmol) were dissolved in 1000 mL of tetrahydrofuran, and 291 mL of a 2N aqueous solution of potassium carbonate was added thereto. The mixture was allowed to react under reflux for 24 hours. After completion of the reaction, the reaction solution was extracted with ethyl acetate, and the organic layer was dried using anhydrous magnesium sulfate, and then purified through a hexane column, thereby obtaining intermediate 51-3 at a yield of 91% (45 g).

Step 4: Preparation of Intermediate 51-4

Intermediate 51-3 (50 g, 200 mmol) was added to 500 mL of dimethylformamide, and NBS (45 g, 260 mmol) was added thereto, followed by stirring at room temperature for 4 hours. 200 mL of water was added to the stirred solution, which was then stirred for 2 hours, and the produced solid material was filtered. The filtrate was washed with 100 mL of methanol, thereby obtaining intermediate 51-4 at a yield of 95% (62 g).

Step 5: Preparation of Intermediate 51-5

Intermediate 51-4 (50 g, 150 mmol) was dissolved in 1000 mL of tetrahydrofuran under an argon atmosphere, and 1.6 M n-butyl lithium (103 mL) was added thereto at −78° C., followed by stirring for about 1 hour. Triethyl borate (31 mL, 180 mmol) was slowly added dropwise thereto at the same temperature, and the solution was stirred for 2 hours, followed by stirring at room temperature for 12 hours. After completion of the reaction, the reaction solution was extracted with ethyl acetate, and the organic layer was dried using anhydrous magnesium sulfate, and then purified through a dichloromethane column, thereby obtaining intermediate 51-5 at a yield of 72% (32 g).

Step 6: Preparation of Intermediate 51-6

Intermediate 51-5 (50 g, 170 mmol), dibromobenzene (44 g, 180 mmol) and tetrakis(triphenylphosphine)palladium(0) (5.8 g, 10 mmol) were dissolved in 1000 mL of tetrahydrofuran, and 253 mL of a 2N aqueous solution of potassium carbonate was added thereto. The mixture was allowed to react under reflux for 24 hours. After completion of the reaction, the reaction solution was extracted with ethyl acetate, and the organic layer was dried using anhydrous magnesium sulfate, and then purified through a hexane column, thereby obtaining intermediate 51-6 at a yield of 67% (46 g).

Step 7: Preparation of Intermediate 51-7

Intermediate 51-6 (50 g, 120 mmol) was dissolved in 1000 mL of tetrahydrofuran under an argon atmosphere, and 1.6 M n-butyl lithium (84 mL) was added thereto at −78° C., followed by stirring for 1 hour. Triethyl borate (25 mL, 150 mmol) was slowly added dropwise thereto at the same temperature, and then the solution was stirred at the same temperature, followed by stirring at room temperature for 12 hours. After completion of the reaction, the reaction solution was extracted with ethyl acetate, and the organic layer was dried using anhydrous magnesium sulfate, and then purified through a dichloromethane column, thereby obtaining intermediate 51-7 at a yield of 74% (34 g).

Step 8: Preparation of Compound of Example 51

Intermediate 51-2 (10 g, 16 mmol), intermediate 51-7 (8 g, 21 mmol) and tetrakis(triphenylphosphine)palladium(0) (1.2 g, 1.1 mmol) were dissolved in 200 mL of tetrahydrofuran, and 25 mL of a 2N aqueous solution of potassium carbonate was added thereto. The mixture was allowed to react under reflux for 24 hours. After completion of the reaction, the reaction solution was extracted with ethyl acetate, and the organic layer was dried using anhydrous magnesium sulfate, and then purified through a hexane column, thereby obtaining a compound of Example 51 at a yield of 60% (6 g).

$^1$H-NMR (200 MHz, CDCl$_3$): δ 7.31-7.52 (m, 14H), 7.56-7.60 (m, 2H), 7.68-7.80 (m, 6H), 7.82-7.92 (m, 4H), 8.35-8.40 (m, 2H)

Examples 52 to 86

Compounds of Examples 52 to 85 were prepared in the same manner as described in Example 51, except that intermediates corresponding to the structures shown in Tables 12 to 19 below were used.

TABLE 12

| Example No. | Chemical structure | $^1$H NMR (CDCl$_3$, 200 MHz) |
|---|---|---|
| 52 | 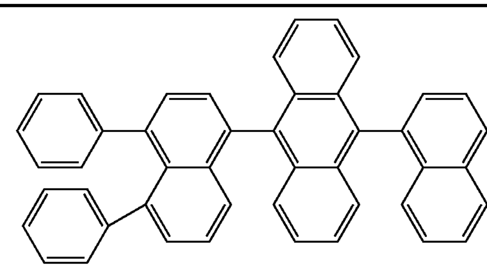 | δ 7.24~7.56 (m, 11H), 7.59~7.71 (m, 7H), 7.74~7.80 (m, 4H), 7.85~7.91 (m, 4H), 8.28~8.32 (m, 2H), 8.35~8.41 (m, 2H) |
| 53 | 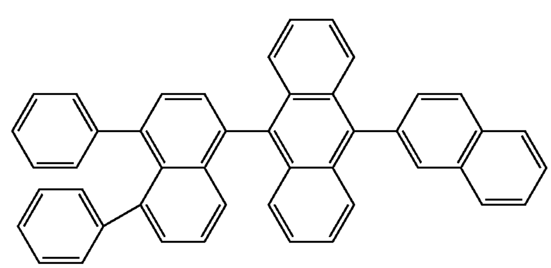 [SMILES: c1ccc(-c2cccc3c(-c4c5ccccc5c(-c5ccc6ccccc6c5)c5ccccc45)ccc(-c4ccccc4)c23)cc1] | δ 7.31~7.51 (m, 9H), 7.53~7.64 (m, 7H), 7.72~7.84 (m, 6H), 7.86~7.92 (m, 4H), 7.98~8.04 (m, 2H), 8.35~8.41 (m, 2H) |

TABLE 12-continued

| Example No. | Chemical structure | $^1$H NMR (CDCl$_3$, 200 MHz) |
|---|---|---|
| 54 | 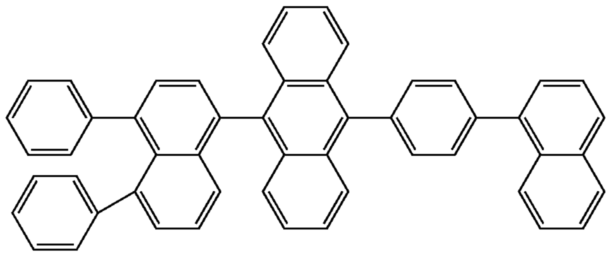 [SMILES: c1ccc(-c2cccc3c(-c4c5ccccc5c(-c5ccc(-c6cccc7ccccc67)cc5)c5ccccc45)ccc(-c4ccccc4)c23)cc1] | δ 7.19~7.50 (m, 17H), 7.60~7.69 (m, 5H), 7.76~7.82 (m, 4H), 7.88~7.93 (m, 4H), 8.30~8.34 (m, 2H), 8.36~8.41 (m, 2H) |
| 55 | 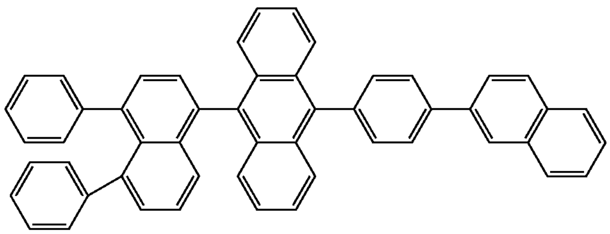 [SMILES: c1ccc(-c2cccc3c(-c4c5ccccc5c(-c5ccc(-c6ccc7ccccc7c6)cc5)c5ccccc45)ccc(-c4ccccc4)c23)cc1] | δ 7.20~7.26 (m 4H), 7.34~7.48 (m, 11H), 7.54~7.62 (m, 5H), 7.70~7.81 (m, 5H), 7.85~7.93 (m, 5H), 7.99~8.03 (m, 2H), 8.35~8.40 (m, 2H) |

TABLE 13

| Example No. | Chemical structure | $^1$H NMR (CDCl$_3$, 200 MHz) |
|---|---|---|
| 56 | 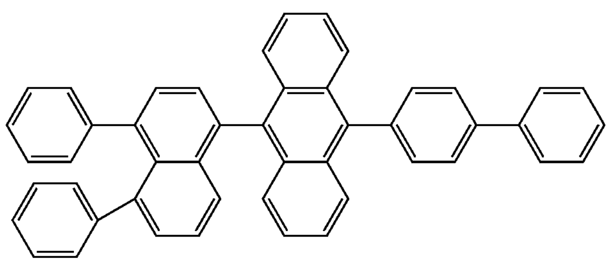 [SMILES: c1ccc(-c2ccc(-c3c4ccccc4c(-c4ccc(-c5ccccc5)c5c(-c6ccccc6)cccc45)c4ccccc34)cc2)cc1] | δ 7.22~7.27 (m, 4H), 7.38~7.51 (m, 14H), 7.58~7.61 (m, 2H), 7.72~7.83 (m, 6H), 7.86~7.93 (m, 4H), 8.37~8.41 (m, 2H) |
| 57 | 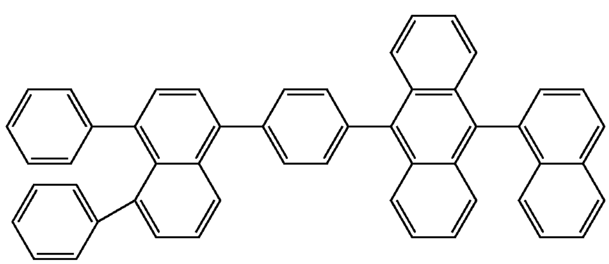 [SMILES: c1ccc(-c2cccc3c(-c4ccc(-c5c6ccccc6c(-c6cccc7ccccc67)c6ccccc56)cc4)ccc(-c4ccccc4)c23)cc1] | δ 7.24~7.53 (m, 17H), 7.59~7.70 (m, 5H), 7.72~7.81 (m, 3H), 7.83~7.94 (m, 5H), 8.35~8.44 (m, 4H) |
| 58 | 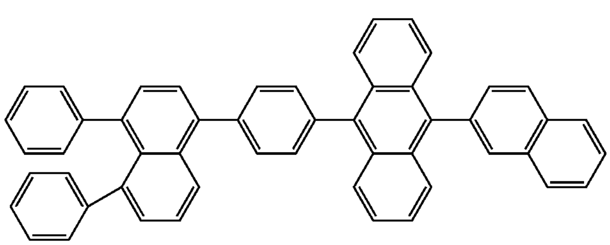 [SMILES: c1ccc(-c2cccc3c(-c4ccc(-c5c6ccccc6c(-c6ccc7ccccc7c6)c6ccccc56)cc4)ccc(-c4ccccc4)c23)cc1] | δ 7.22~7.25 (m, 4H), 7.33~7.45 (m, 9H), 7.47~7.60 (m, 7H), 7.65~7.78 (m, 5H), 7.84~7.92 (m, 5H), 8.01~8.04 (m, 2H), 8.34~8.40 (m, 2H) |

TABLE 14
| Example No. | Chemical structure | ¹H NMR (CDCl₃, 200 MHz) |
|---|---|---|
| 59 | 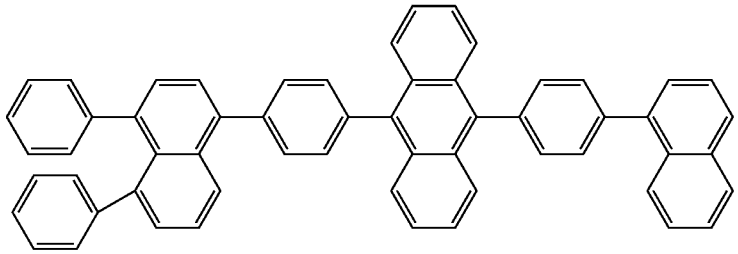 [SMILES: c1ccc(-c2cccc3c(-c4ccc(-c5c6ccccc6c(-c6ccc(-c7cccc8ccccc78)cc6)c6ccccc56)cc4)ccc(-c4ccccc4)c23)cc1] | δ 7.23~7.50 (m, 21H), 7.60~7.71 (m, 5H), 7.69~7.81 (m, 4H), 7.85~7.93 (m, 4H), 8.35~8.44 (m, 4H) |
| 60 | 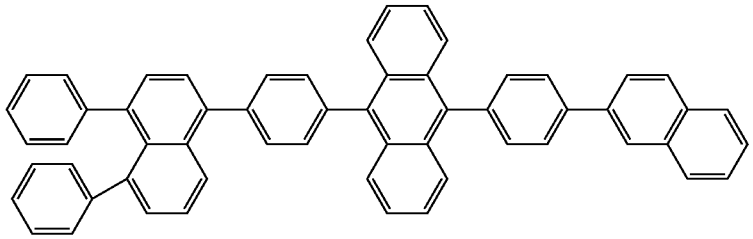 [SMILES: c1ccc(-c2cccc3c(-c4ccc(-c5c6ccccc6c(-c6ccc(-c7ccc8ccccc8c7)cc6)c6ccccc56)cc4)ccc(-c4ccccc4)c23)cc1] | δ 7.23~7.27 (m, 8H), 7.36~7.49 (m, 11H), 7.54~7.62 (m, 5H), 7.69~7.81 (m, 5H), 7.85~7.93 (m, 5H), 7.99~8.03 (m, 2H), 8.35~8.40 (m, 2H) |
| 61 | 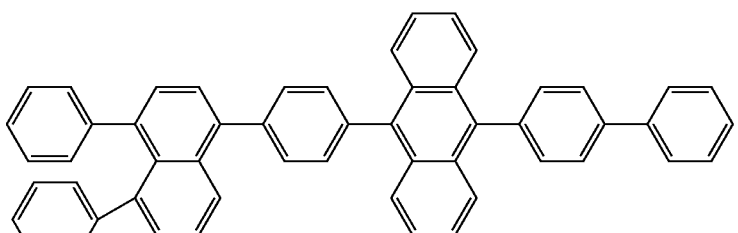 | δ 7.22~7.27 (m, 8H), 7.36~7.52 (m, 14H), 7.56~7.62 (m, 2H), 7.71~7.83 (m, 6H), 7.86~7.94 (m, 4H), 8.35~8.40 (m, 2H) |
| 62 | 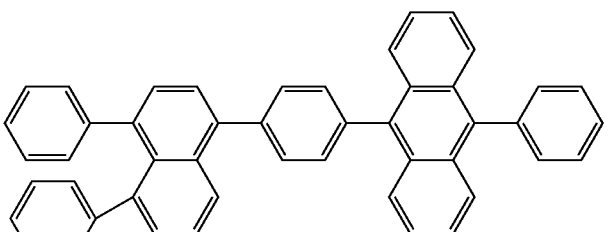 | δ 7.21~7.56 (m, 16H), 7.59~7.65 (m, 4H), 7.69~7.81 (m, 6H), 7.85~7.92 (m, 4H), 8.37~8.52 (m, 4H) |
| 63 | 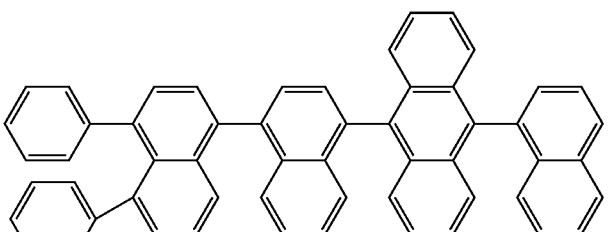 | δ 7.21~7.34 (m, 6H), 7.36~7.51 (m, 9H), 7.56~7.64 (m, 7H), 7.72~7.83 (m, 4H), 7.87~7.91 (m, 4H), 8.31~8.46 (m, 6H) |
| 64 | 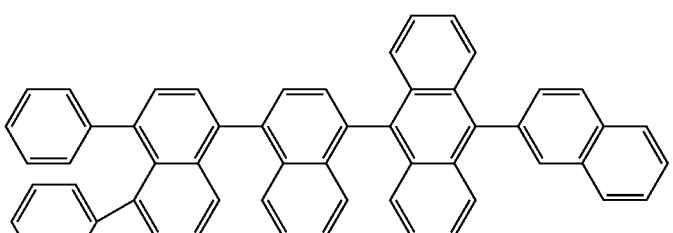 | δ 7.19~7.32 (m, 6H), 7.34~7.50 (m, 7H), 7.54~7.63 (m, 7H), 7.71~7.83 (m, 5H), 7.85~793 (m, 5H), 7.98~8.03 (m, 2H), 8.35~8.51 (m, 4H) |

TABLE 15

| Example No. | Chemical structure | ¹H NMR (CDCl₃, 200 MHz) |
|---|---|---|
| 65 | 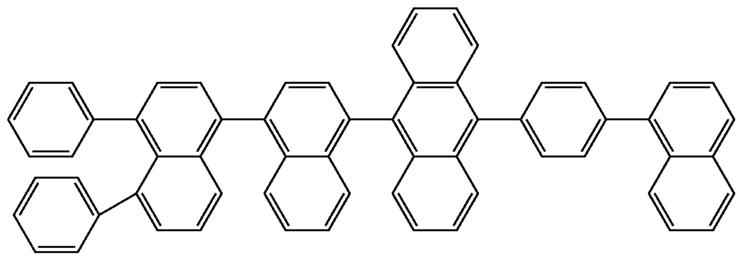 [SMILES: c1ccc(-c2cccc3c(-c4ccc(-c5c6ccccc6c(-c6ccc(-c7cccc8ccccc78)cc6)c6ccccc56)c5ccccc45)ccc(-c4ccccc4)c23)cc1] | δ 7.20~7.54 (m, 19H), 7.58~7.68 (m, 7H), 7.75~7.85 (m, 4H), 7.88~7.92 (m, 4H), 8.32~8.46 (m, 6H) |
| 66 | 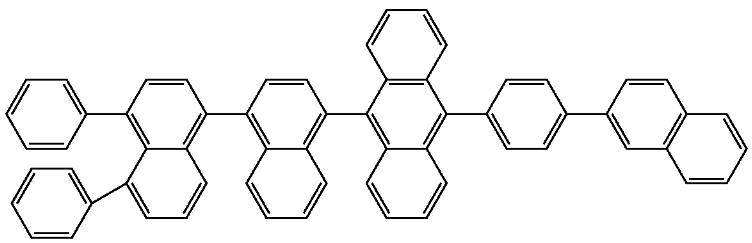 [SMILES: c1ccc(-c2cccc3c(-c4ccc(-c5c6ccccc6c(-c6ccc(-c7ccc8ccccc8c7)cc6)c6ccccc56)c5ccccc45)ccc(-c4ccccc4)c23)cc1] | δ 7.21~7.52 (m, 17H), 7.56~7.65 (m, 7H), 7.70~7.83 (m, 5H), 7.86~7.94 (m, 5H), 7.99~8.03 (m, 2H), 8.35~8.51 (m, 4H) |
| 67 | 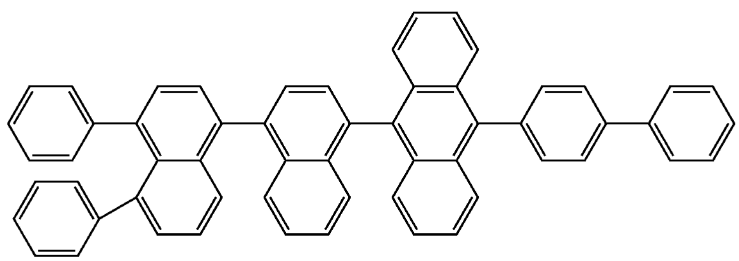 [SMILES: c1ccc(-c2ccc(-c3c4ccccc4c(-c4ccc(-c5ccc(-c6ccccc6)c6c(-c7ccccc7)cccc56)c5ccccc45)c4ccccc34)cc2)cc1] | δ 7.20~7.55 (m, 20H), 7.58~7.64 (m, 4H), 7.68~7.81 (m, 6H), 7.85~7.92 (m, 4H), 8.37~8.52 (m, 4H) |
| 68 | 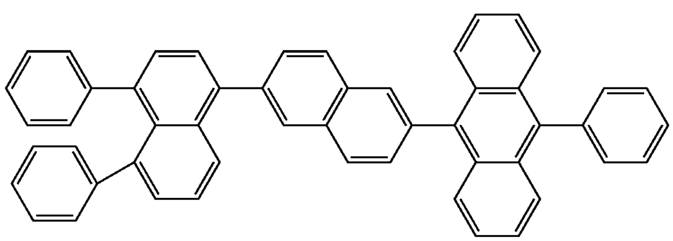 [SMILES: c1ccc(-c2c3ccccc3c(-c3ccc4cc(-c5ccc(-c6ccccc6)c6c(-c7ccccc7)cccc56)ccc4c3)c3ccccc23)cc1] | δ 7.23~7.26 (m, 2H), 7.34~7.57 (m, 12H), 7.60~7.68 (m, 4H), 7.72~7.85 (m, 8H), 7.88~7.96 (m, 6H), 8.37~8.49 (m, 2H) |

TABLE 16

| Example No. | Chemical structure | ¹H NMR (CDCl₃, 200 MHz) |
|---|---|---|
| 69 | 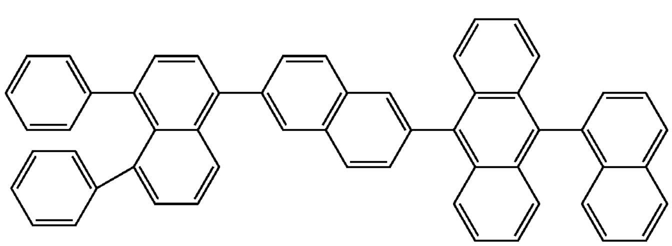 [SMILES: c1ccc(-c2cccc3c(-c4ccc5cc(-c6c7ccccc7c(-c7cccc8ccccc78)c7ccccc67)ccc5c4)ccc(-c4ccccc4)c23)cc1] | δ 7.32~7.52 (m, 13H), 7.58~7.82 (m, 13H), 7.86~7.94 (m, 6H), 8.37~8.52 (m, 4H) |

TABLE 16-continued
| Example No. | Chemical structure | $^1$H NMR (CDCl$_3$, 200 MHz) |
|---|---|---|
| 70 | 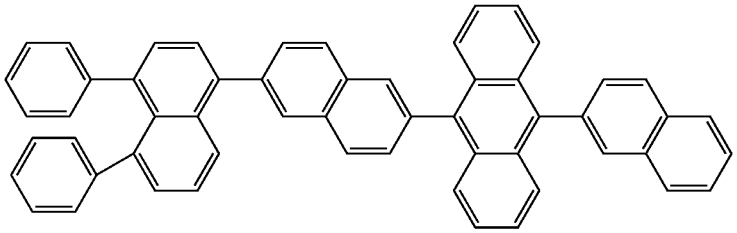 [SMILES: c1ccc(-c2cccc3c(-c4ccc5cc(-c6c7ccccc7c(-c7ccc8ccccc8c7)c7ccccc67)ccc5c4)ccc(-c4ccccc4)c23)cc1] | δ 7.36~7.52 (m, 11H), 7.56~7.66 (m, 7H), 7.71~7.82 (m, 7H), 7.84~7.92 (m, 7H), 8.00~8.04 (m, 2H), 8.40~8.51 (m, 2H) |
| 71 | 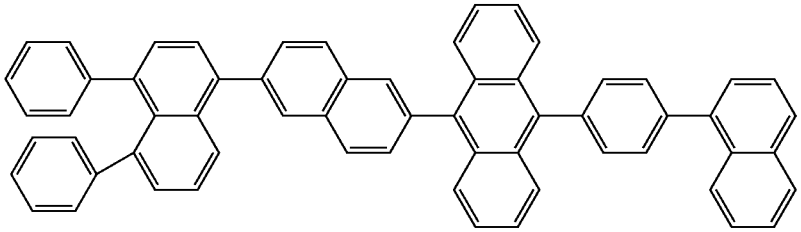 [SMILES: c1ccc(-c2cccc3c(-c4ccc5cc(-c6c7ccccc7c(-c7ccc(-c8cccc9ccccc89)cc7)c7ccccc67)ccc5c4)ccc(-c4ccccc4)c23)cc1] | δ 7.21~7.54 (m, 17H), 7.58~7.82 (m, 13H), 7.86~7.94 (m, 6H), 8.37~8.52 (m, 4H) |
| 72 | 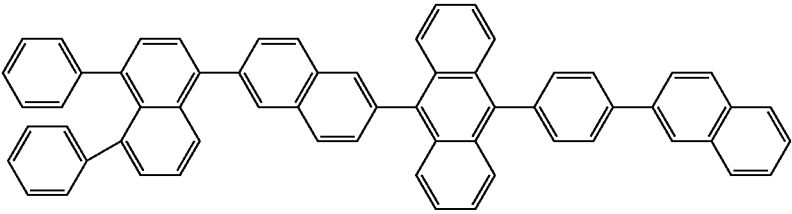 [SMILES: c1ccc(-c2cccc3c(-c4ccc5cc(-c6c7ccccc7c(-c7ccc(-c8ccc9ccccc9c8)cc7)c7ccccc67)ccc5c4)ccc(-c4ccccc4)c23)cc1] | δ 7.24~7.27 (m, 4H), 7.35~7.52 (m, 11H), 7.56~7.65 (m, 7H), 7.70~7.83 (m, 7H), 7.86~7.94 (m, 7H), 7.99~8.03 (m, 2H), 8.40~8.51 (m, 2H) |
| 73 | 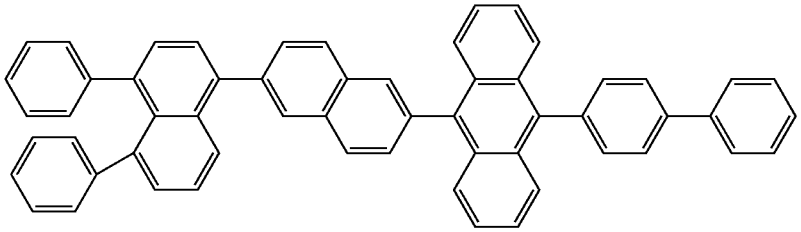 [SMILES: c1ccc(-c2ccc(-c3c4ccccc4c(-c4ccc5cc(-c6ccc(-c7ccccc7)c7c(-c8ccccc8)cccc67)ccc5c4)c4ccccc34)cc2)cc1] | δ 7.23~7.26 (m, 4H), 7.34~7.55 (m, 14H), 7.58~7.65 (m, 4H), 7.71~7.85 (m, 8H), 7.87~7.96 (m, 6H), 8.38~8.49 (m, 2H) |
TABLE 17
| Example No. | Chemical structure | $^1$H NMR (CDCl$_3$, 200 MHz) |
|---|---|---|
| 74 | 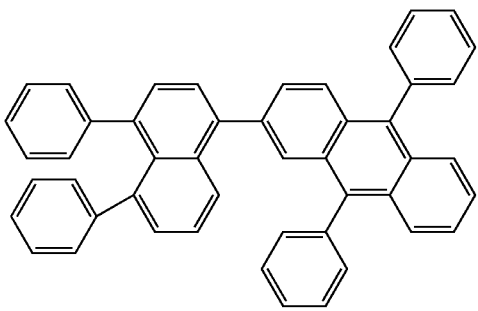 [SMILES: c1ccc(-c2c3ccccc3c(-c3ccccc3)c3cc(-c4ccc(-c5ccccc5)c5c(-c6ccccc6)cccc45)ccc23)cc1] | δ 7.21~7.31 (m, 5H), 7.37~7.57 (m, 8H), 7.61~7.73 (m, 7H), 7.76~7.81 (m, 4H), 7.85~7.94 (m, 3H), 8.12~8.14 (s, 1H), 8.41~8.52 (m, 4H) |

TABLE 17-continued

| Example No. | Chemical structure | ¹H NMR (CDCl₃, 200 MHz) |
|---|---|---|
| 75 | 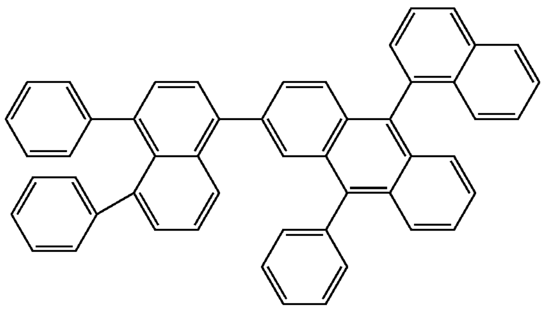 [SMILES: c1ccc(-c2c3ccccc3c(-c3cccc4ccccc34)c3ccc(-c4ccc(-c5ccccc5)c5c(-c6ccccc6)cccc45)cc23)cc1] | δ 7.23~7.32 (m, 5H), 7.34~7.55 (m, 9H), 7.58~7.69 (m, 8H), 7.76~7.81 (m, 4H), 7.86~7.97 (m, 3H), 8.11~8.13 (s, 1H), 8.40~8.52 (m, 4H) |
| 76 | 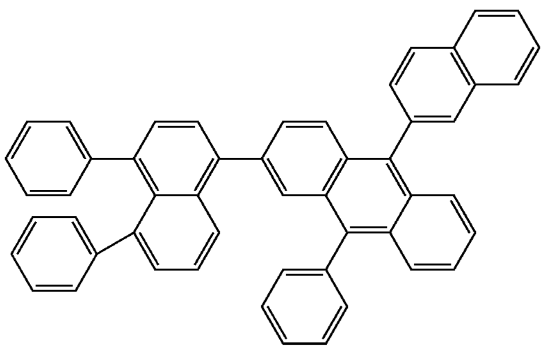 [SMILES: c1ccc(-c2c3ccccc3c(-c3ccc4ccccc4c3)c3ccc(-c4ccc(-c5ccccc5)c5c(-c6ccccc6)cccc45)cc23)cc1] | δ 7.32~7.56 (m, 12H), 7.58~7.66 (m, 8H), 7.70~7.82 (m, 5H), 7.88~8.04 (m, 5H), 8.08~8.15 (m, 2H), 8.42~8.51 (m, 2H) |
| 77 | 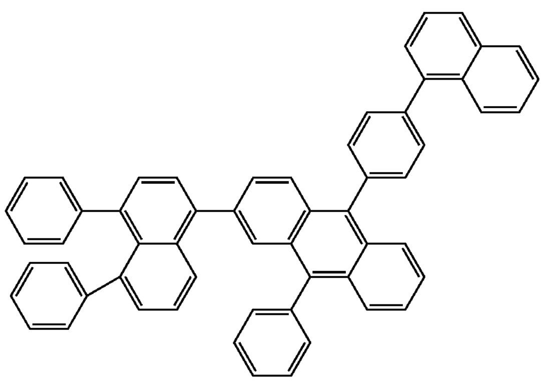 [SMILES: c1ccc(-c2c3ccccc3c(-c3ccc(-c4cccc5ccccc45)cc3)c3ccc(-c4ccc(-c5ccccc5)c5c(-c6ccccc6)cccc45)cc23)cc1] | δ 7.23~7.54 (m, 18H), 7.58~7.69 (m, 8H), 7.76~7.81 (m, 4H), 7.86~7.97 (m, 3H), 8.11~8.13 (s, 1H), 8.40~8.52 (m, 4H) |

TABLE 18

| Example No. | Chemical structure | ¹H NMR (CDCl₃, 200 MHz) |
|---|---|---|
| 78 | 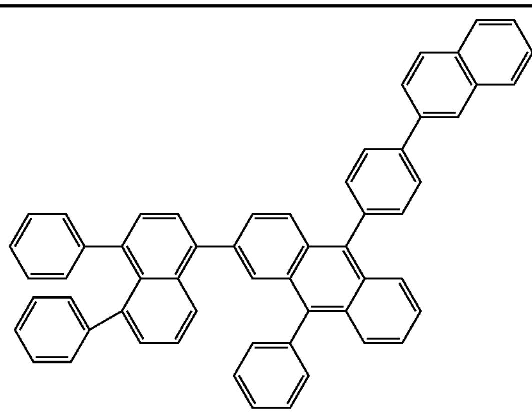 | δ 7.22~7.26 (m, 4H), 7.35~7.56 (m, 12H), 7.58~7.66 (m, 8H), 7.70~7.82 (m, 5H), 7.88~8.04 (m, 5H), 8.08~8.15 (m, 2H), 8.42~8.51 (m, 2H) |

TABLE 18-continued

| Example No. | Chemical structure | ¹H NMR (CDCl₃, 200 MHz) |
|---|---|---|
| 79 | 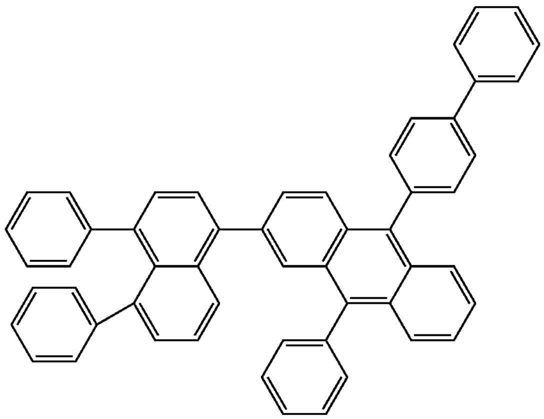 [SMILES: c1ccc(-c2ccc(-c3c4ccccc4c(-c4ccccc4)c4cc(-c5ccc(-c6ccccc6)c6c(-c7ccccc7)cccc56)ccc34)cc2)cc1] | δ 7.23~7.26 (m, 4H), 7.34~7.56 (m, 15H), 7.58~7.67 (m, 5H), 7.71~7.84 (m, 6H), 7.88~7.96 (m, 4H), 8.41~8.50 (m, 2H) |
| 80 | 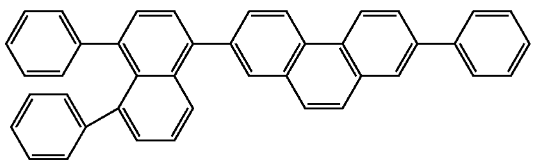 [SMILES: c1ccc(-c2ccc3c(ccc4cc(-c5ccc(-c6ccccc6)c6c(-c7ccccc7)cccc56)ccc43)c2)cc1] | δ 7.32~7.49 (m, 10H), 7.54~7.60 (m, 2H), 7.70~7.81 (m, 8H), 7.97~8.10 (m, 2H), 8.32~8.48 (m, 4H), 8.76~8.91 (m, 2H) |
| 81 | 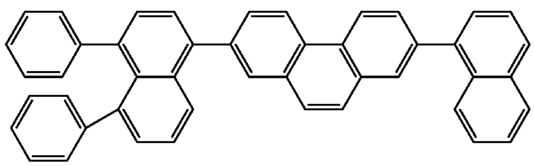 [SMILES: c1ccc(-c2cccc3c(-c4ccc5c(ccc6cc(-c7cccc8ccccc78)ccc65)c4)ccc(-c4ccccc4)c23)cc1] | δ 7.26~7.50 (m, 9H), 7.59~7.83 (m, 11H), 7.95~8.01 (m, 2H), 8.29~8.47 (s, 6H), 8.76~8.90 (m, 2H) |

TABLE 19

| Example No. | Chemical structure | ¹H NMR (CDCl₃, 200 MHz) |
|---|---|---|
| 82 | 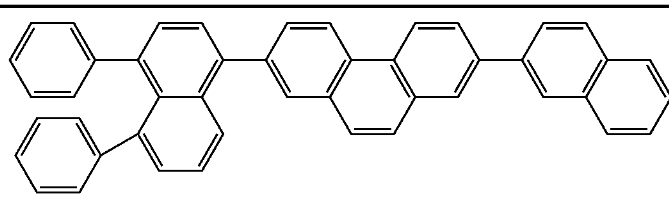 | δ 7.30~7.48 (m, 7H), 7.54~7.62 (m, 5H), 7.67~7.82 (m, 7H), 7.95~8.15 (m, 5H), 8.34~8.49 (m, 4H), 8.76~8.91 (m, 2H) |
| 83 | 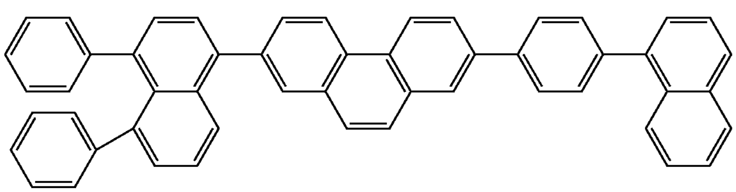 [SMILES: c1ccc(-c2cccc3c(-c4ccc5c(ccc6cc(-c7ccc(-c8cccc9ccccc89)cc7)ccc65)c4)ccc(-c4ccccc4)c23)cc1] | δ 7.22~7.51 (m, 13H), 7.58~7.82 (m, 11H), 7.96~8.01 (m, 2H), 8.31~8.50 (s, 6H), 8.78~8.91 (m, 2H) |
| 84 | 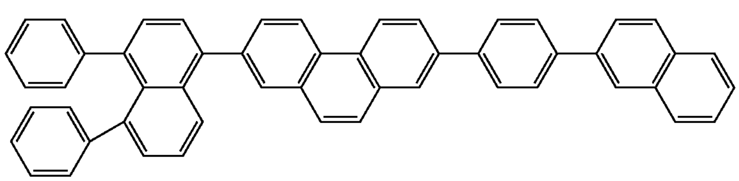 [SMILES: c1ccc(-c2cccc3c(-c4ccc5c(ccc6cc(-c7ccc(-c8ccc9ccccc9c8)cc7)ccc65)c4)ccc(-c4ccccc4)c23)cc1] | δ 7.23~7.26 (m, 4H), 7.32~7.50 (m, 7H), 7.56~7.64 (m, 5H), 7.69~7.83 (m, 7H), 7.94~8.14 (m, 5H), 8.34~8.49 (m, 4H), 8.76~8.91 (m, 2H) |

TABLE 19-continued

| Example No. | Chemical structure | $^1$H NMR (CDCl$_3$, 200 MHz) |
|---|---|---|
| 85 | 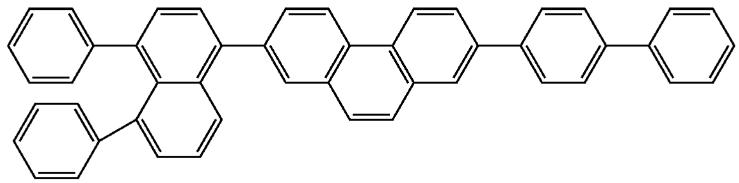 [SMILES: c1ccc(-c2ccc(-c3ccc4c(ccc5cc(-c6ccc(-c7ccccc7)c7c(-c8ccccc8)cccc67)ccc54)c3)cc2)cc1] | δ 7.23~7.26 (m, 4H), 734~7.51 (m, 10H), 7.57~7.62 (m, 2H), 7.73~7.82 (m, 8H), 7.99~8.11 (m, 2H), 8.33~8.49 (m, 4H), 8.76~8.91 (m, 2H) |

Example 86

A compound of Example 86 was prepared according to the following preparation method.

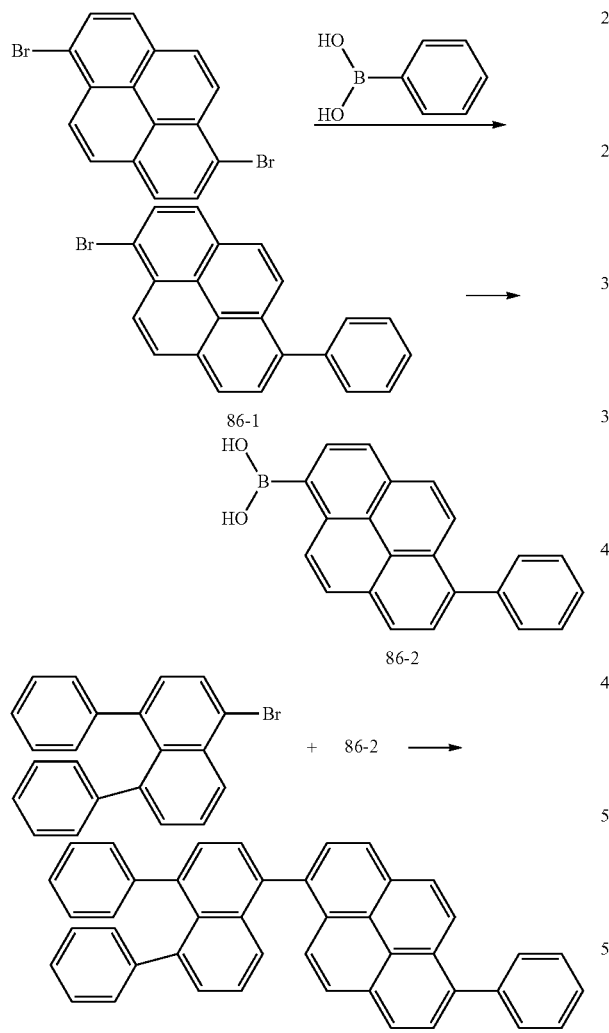

Example 86

Step 1: Preparation of Intermediate 86-1

1,6-dibromopyrene (50 g, 140 mmol), phenylboronic acid (19 g, 150 mmol) and tetrakis(triphenylphosphine)palladium (0) (4.8 g, 4.2 mmol) were dissolved in 500 mL of tetrahydrofuran, and 208 mL of a 2N aqueous solution of potassium carbonate was added thereto. The mixture was allowed to react under reflux for 24 hours. After completion of the reaction, the reaction solution was extracted with ethyl acetate, and the organic layer was dried using anhydrous magnesium sulfate, and then purified through a hexane column, thereby obtaining intermediate 86-1 at a yield of 69% (34 g).

Step 2: Preparation of Intermediate 86-2

Intermediate 86-1 (50 g, 140 mmol) was dissolved in 1000 mL of tetrahydrofuran, and 1.6 M n-butyl lithium (96 mL) was added thereto at −78° C., followed by stirring for about 1 hour. Triethyl borate (29 mL, 170 mmol) was slowly added dropwise thereto at the same temperature, and then the solution was stirred for 2 hours, followed by stirring at room temperature for 12 hours. After completion of the reaction, the reaction solution was extracted with ethyl acetate, and the organic layer was dried using anhydrous magnesium sulfate, and then purified through a dichloromethane column, thereby obtaining intermediate 86-2 at a yield of 75% (34 g).

Step 3: Preparation of Compound of Example 86

Intermediate 86-2 (10 g, 16 mmol), intermediate 38-2 (6.9 g, 21 mmol) and tetrakis(triphenylphosphine)palladium(0) (0.6 g, 0.5 mmol) were dissolved in 200 mL of tetrahydrofuran, and 25 mL of a 2N aqueous solution of potassium carbonate was added thereto. The mixture was allowed to react under reflux for 24 hours. After completion of the reaction, the reaction solution was extracted with ethyl acetate, and the organic layer was dried using anhydrous magnesium sulfate, and then purified through a hexane column, thereby obtaining a compound of Example 86 at a yield of 66% (6 g).

$^1$H-NMR (200 MHz, CDCl$_3$): δ 7.34-7.47 (m, 6H), 7.48-7.54 (m, 4H), 7.56-7.61 (m, 2H), 7.67-7.85 (m, 10H), 7.95-8.14 (m, 4H), 8.33-8.45 (m, 2H)

Examples 87 to 95

Compounds of Examples 87 to 95 were prepared in the same manner as described in Example 86, except that intermediates corresponding to the structures shown in Tables 20 and 21 below were used instead of intermediates 51-2 and 86-2, respectively.

TABLE 20

| Example No. | Chemical structure | $^1$H NMR (CDCl$_3$, 200 MHz) |
|---|---|---|
| 87 | 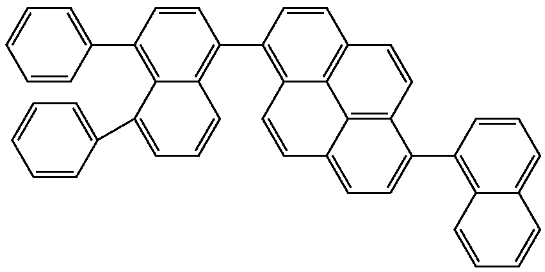 [SMILES: c1ccc(-c2cccc3c(-c4ccc5ccc6c(-c7cccc8ccccc78)ccc7ccc4c5c76)ccc(-c4ccccc4)c23)cc1] | δ 7.31~7.51 (m, 9H), 7.58~7.82 (m, 13H), 7.89~7.94 (m, 2H), 7.98~8.08 (m, 2H), 8.31~8.46 (m, 4H) |
| 88 | 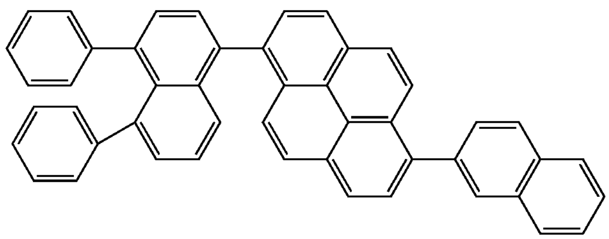 [SMILES: c1ccc(-c2cccc3c(-c4ccc5ccc6c(-c7ccc8ccccc8c7)ccc7ccc4c5c76)ccc(-c4ccccc4)c23)cc1] | δ 7.33~7.52 (m, 8H), 7.56~7.63 (m, 4H), 7.67~7.83 (m, 9H), 7.92~8.13 (m, 7H), 8.31~8.45 (m, 2H) |
| 89 | 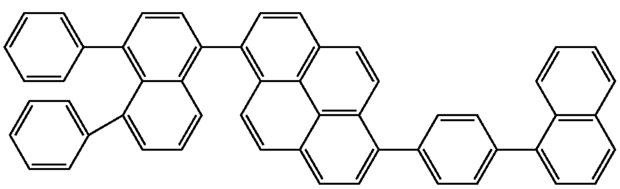 [SMILES: c1ccc(-c2cccc3c(-c4ccc5ccc6c(-c7ccc(-c8cccc9ccccc89)cc7)ccc7ccc4c5c76)ccc(-c4ccccc4)c23)cc1] | δ 7.23~7.52 (m, 13H), 7.58~7.82 (m, 13H), 7.89~7.93 (m, 2H), 7.97~8.06 (m, 2H), 8.32~8.46 (m, 4H) |
| 90 | 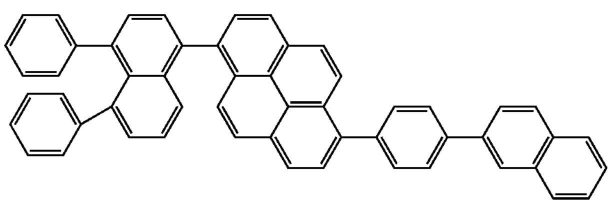 [SMILES: c1ccc(-c2cccc3c(-c4ccc5ccc6c(-c7ccc(-c8ccc9ccccc9c8)cc7)ccc7ccc4c5c76)ccc(-c4ccccc4)c23)cc1] | δ 7.23~7.26 (m, 4H), 7.34~7.50 (m, 7H), 7.54~7.62 (m, 5H), 7.68~7.82 (m, 9H), 7.94~8.14 (m, 7H), 8.31~8.45 (m, 2H) |
| 91 | 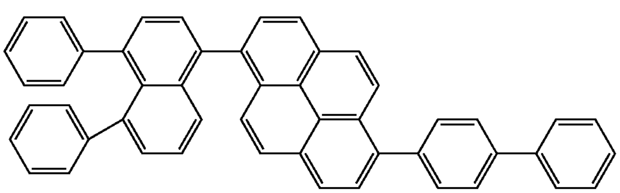 [SMILES: c1ccc(-c2ccc(-c3ccc4ccc5c(-c6ccc(-c7ccccc7)c7c(-c8ccccc8)cccc67)ccc6ccc3c4c65)cc2)cc1] | δ 7.22~7.27 (m, 4H), 7.36~7.52 (m, 10H), 7.57~7.62 (m, 2H), 7.69~7.84 (m, 10H), 7.94~8.14 (m, 4H), 8.32~8.45 (m, 2H) |

TABLE 21

| Example No. | Chemical structure | $^1$H NMR (CDCl$_3$, 200 MHz) |
|---|---|---|
| 92 | 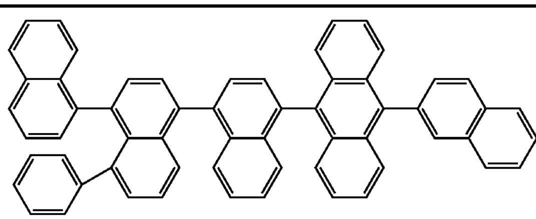 | δ 7.30~7.52 (m, 12H), 7.57~7.71 (m, 13H), 7.87~7.94 (m, 5H), 7.99~8.07 (m, 2H), 8.37~8.43 (m, 2H), 8.46~8.57 (m, 4H) |

TABLE 21-continued

| Example No. | Chemical structure | $^1$H NMR (CDCl$_3$, 200 MHz) |
|---|---|---|
| 93 | 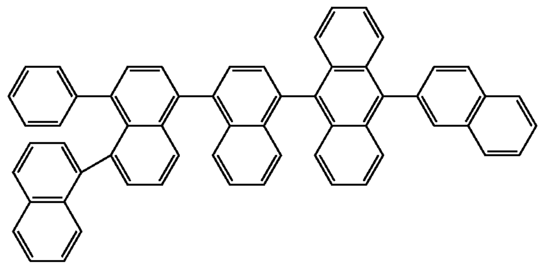 [SMILES: c1ccc(-c2ccc(-c3ccc(-c4c5ccccc5c(-c5ccc6ccccc6c5)c5ccccc45)c4ccccc34)c3cccc(-c4cccc5ccccc45)c23)cc1] | δ 7.32~7.50 (m, 12H), 7.57~7.81 (m, 13H), 7.89~7.93 (m, 5H), 7.99~8.06 (m, 2H), 8.40~8.52 (m, 6H) |
| 94 | 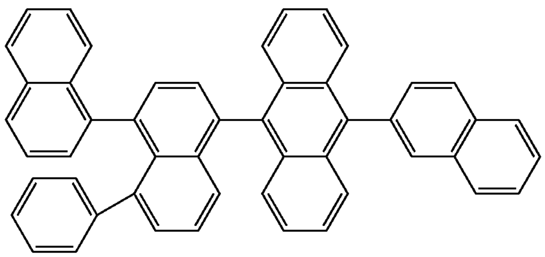 [SMILES: c1ccc(-c2cccc3c(-c4c5ccccc5c(-c5ccc6ccccc6c5)c5ccccc45)ccc(-c4cccc5ccccc45)c23)cc1] | δ 7.30~7.51 (m, 10H), 7.55~7.79 (m, 11H), 7.89~7.93 (m, 5H), 7.99~8.06 (m, 2H), 8.40~8.52 (m, 4H) |
| 95 | 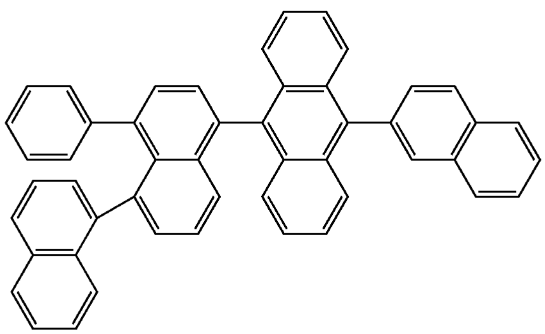 [SMILES: c1ccc(-c2ccc(-c3c4ccccc4c(-c4ccc5ccccc5c4)c4ccccc34)c3cccc(-c4cccc5ccccc45)c23)cc1] | δ 7.32~7.50 (m, 10H), 7.57~7.81 (m, 11H), 7.87~7.92 (m, 5H), 7.99~8.06 (m, 2H), 8.41~8.53 (m, 4H) |

TEST EXAMPLES

Preparation of Organic Electroluminescent Device

Test Example 1

Preparation of Organic Electroluminescent Device Using Compound of Example 3

A substrate having a size of 40 mm×40 mm×0.7 mm and comprising an ITO (indium tin oxide) transparent electrode having a thin film thickness of 100 nm was washed ultrasonically in detergent-containing distilled water for 10 minutes, and washed twice with distilled water for 10 minutes.

After completion of washing with distilled water, the substrate was ultrasonically washed sequentially with solvents, including isopropyl alcohol, acetone and methanol, followed by drying. After wet washing, the substrate was subjected to dry washing using oxygen/argon plasma, and then the glass substrate having transparent electrode lines was mounted on the substrate holder of a vacuum deposition system. On the surface of the substrate side having the transparent electrode lines formed thereon, an N,N'-diphenyl-N,N'-bis-[4-(phenyl-m-tolylamino)phenyl]-biphenyl-4,4'-diamine film (hereinafter, referred to as "DNTPD film") having a thickness of 60 nm was formed so as to cover the transparent electrode. The DNTPD film functions as a hole-injecting layer. Next, on the DNTPD film, a 4,4'-bis[N-(1-naphthyl)-N-phenylamino]biphenyl film (hereinafter, referred to as "NPB film") having a thickness of nm was formed. The NPB film functions as a hole-transporting layer.

Next, the compound of Example 3 and a compound having the following structural formula were mixed at a weight ratio of 100:5 and deposited on the NPB film, thereby forming a light-emitting layer having a film thickness of 30 nm.

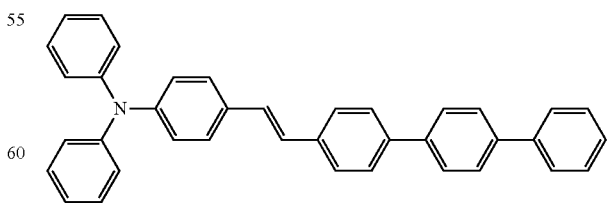

The compound of Example 3 functions as a host in the light-emitting layer, and the compound having the above structural formula functions as a dopant in the light-emitting layer. On the film, a tris(8-quinolinol)aluminum film (hereinafter, referred to as "Alq film") having a thickness of nm was formed. The Alq film functions as an electron-transporting layer.

Next, LiF was deposited to form an electron-injecting layer. On the LiF film, metal aluminum was deposited to form a metal cathode, thereby fabricating an organic electroluminescent device. Measurements were performed for the fabricated organic electroluminescent device at a voltage of 7V, and as a result, the current density was 77.7 mA/cm$^2$, and a spectrum having a brightness of 3,599 cd/m$^2$ corresponding to x=0.148 and y=0.141 of the 1931 CIE color coordinates was observed. The luminous efficiency of the device was measured to be 4.93 cd/A at 7V, and this luminous efficiency value was calculated to be a luminous efficiency/y of 35.0.

Test Example 2

Preparation of Organic Electroluminescent Device Using Compound of Example 5

An organic electroluminescent device was fabricated in the same manner as described in Test Example 1, except that the compound of Example 5 was used instead of the compound of Example 3 as the light-emitting material. Measurements were performed for the fabricated organic electroluminescent device at a voltage of 7V, and as a result, the current density was 82.5 mA/cm$^2$, and a spectrum having a brightness of 4,197 cd/m$^2$ corresponding to x=0.146 and y=0.142 of the 1931 CIE color coordinates was observed. The luminous efficiency of the device was measured to be 5.39 cd/A at 7V, and this luminous efficiency value was calculated to be a luminous efficiency/y of 38.0.

Test Example 3

Preparation of Organic Electroluminescent Device Using Compounds of Examples 6, 7, 8, 23 and 39

Organic electroluminescent devices were fabricated in the same manner as described in Test Example 1, except that the compounds of Examples 6, 7, 8, 23 and 39 were used instead of the compound of Example 3 as the light-emitting material. Measurements were carried out on the fabricated device.

Test Example 4

Preparation of Organic Electroluminescent Device Using Compounds of Examples 51, 52, 53, 54, 57, 59, 64 and 88

An organic electroluminescent device was fabricated in the same manner as described in Test Example 1, except that the compounds of Examples 51, 52, 53, 54, 57, 59, 64 and 88 were used instead of the compound of Example 3 as the light-emitting material. Measurements were carried out on the fabricated device.

Test Example 5

Preparation of Organic Electroluminescent Device Using Compound AN

An organic electroluminescent device was fabricated in the same manner as described in Test Example 1, except that compound AN having the following structural formula was used instead of the compound of Example 3 as the light-emitting material.

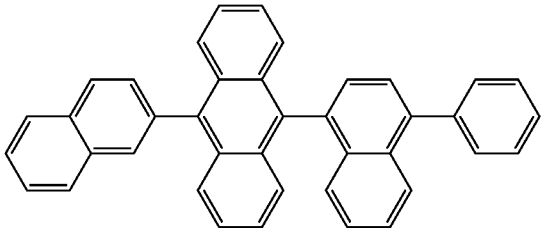

Molecular Formula: $C_{40}H_{26}$
Formula Weight: 506.63444

Measurements were performed for the fabricated organic electroluminescent device at a voltage of 7V, and as a result, the current density was 75.3 mA/cm$^2$, and a spectrum having a brightness of 3.121 cd/m$^2$ corresponding to x=0.151 and y=0.142 of the 1931 CIE color coordinates was observed. The luminous efficiency of the device was measured to be 4.87 cd/A at 7V, and this luminous efficiency value was calculated to be a luminous efficiency/y of 34.3.

Test Example 6

Preparation of Organic Electroluminescent Device Using Compound ADN

An organic electroluminescent device was fabricated in the same manner as described in Test Example 1, except that compound ADN having the following structural formula was used instead of the compound AN used in Test Example 1 as the light-emitting material.

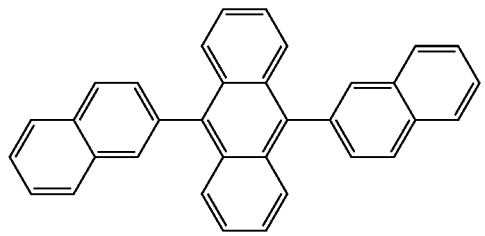

Molecular Formula: $C_{34}H_{22}$
Formula Weight: 430.53848

Measurements were performed for the fabricated organic electroluminescent device at a voltage of 7V, and as a result, the current density was 80.5 mA/cm$^2$, and a spectrum having a brightness of 2,964 cd/m$^2$ corresponding to x=0.143 and y=0.145 of the 1931 CIE color coordinates was observed. The luminous efficiency of the device was measured to be 4.80 cd/A at 7V, and this luminous efficiency value was calculated to be a luminous efficiency/y of 33.1.

The results of the above measurements are summarized in Tables 22 and 23 below. Lifetime in Table 22 is expressed as a percentage relative to 100% of compound AN in accelerated lifetime (1000 nit), and lifetime in Table 23 is expressed as a percentage relative to 100% of compound ADN in accelerated lifetime (1000 nit).

TABLE 22

| Host material | Dopant material | Electroluminescence (nm) (EL) | Luminous efficiency (cd/A) @ 7 V | Luminous efficiency/ CIEy | Color coordinates @ 7 V CIEx | CIEy | Lifetime 1000 cd/m² |
|---|---|---|---|---|---|---|---|
| Example 3 | BD | 461 | 4.93 | 35.0 | 0.148 | 0.141 | 93% |
| Example 4 |  | 462 | 5.39 | 38.0 | 0.146 | 0.142 | 113% |
| Example 6 |  | 461 | 5.22 | 36.0 | 0.147 | 0.145 | 108% |
| Example 7 |  | 463 | 5.53 | 39.2 | 0.145 | 0.141 | 112% |
| Example 9 |  | 460 | 4.88 | 33.4 | 0.145 | 0.146 | 92% |
| Example 23 |  | 461 | 5.12 | 36.8 | 0.145 | 0.139 | 98% |
| Example 39 |  | 462 | 5.42 | 36.4 | 0.146 | 0.149 | 107% |
| AN |  | 460 | 4.87 | 34.3 | 0.151 | 0.142 | 100% |
| ADN |  | 462 | 4.80 | 33.1 | 0.143 | 0.145 | 91% |

TABLE 23

| Host material | Dopant material | Electroluminescence (nm) (EL) | Luminous efficiency (cd/A) @ 7 V | Luminous efficiency/ CIEy | Color coordinates @ 7 V CIEx | CIEy | Lifetime 1000 cd/m² |
|---|---|---|---|---|---|---|---|
| Example 51 | BD | 462 | 5.12 | 36.3 | 0.146 | 0.141 | 91% |
| Example |  | 461 | 5.34 | 37.3 | 0.144 | 0.143 | 110% |
| Example |  | 461 | 5.36 | 37.2 | 0.145 | 0.144 | 103% |
| Example |  | 462 | 5.42 | 38.7 | 0.144 | 0.140 | 112% |
| Example |  | 462 | 5.24 | 37.7 | 0.145 | 0.139 | 117% |
| Example |  | 461 | 5.35 | 40.2 | 0.143 | 0.133 | 98% |
| Example |  | 462 | 5.17 | 36.7 | 0.145 | 0.141 | 93% |
| Example |  | 462 | 5.23 | 38.2 | 0.147 | 0.137 | 111% |
| ADN |  | 462 | 4.80 | 33.1 | 0.143 | 0.145 | 100% |

As can be seen in Tables 22 and 23 above, the compounds of the Examples have excellent luminous efficiency and lifetime compared to the compounds of the Comparative Examples.

As described above, the inventive compound represented by formula 1 has a low degree of crystallization, because it is asymmetrical. Thus, the thin film of the organic electroluminescent device comprising the inventive compound of formula 1 has high stability and a long lifetime. In addition, the compound of formula 1 has high color purity and high luminous efficiency, depending on the substituents thereof, and the organic electroluminescent device comprising the compound of formula 1 can be driven at low voltages. Accordingly, the inventive compound represented by formula 1 can be used in various organic electroluminescent devices, including backlight units for displays or flat panel displays such as wall-mounted televisions, lighting devices, and the like.

What is claimed is:
1. A compound represented by the following formula 1:

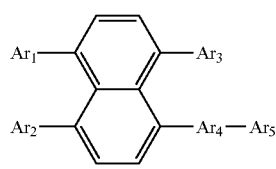

[Formula 1]

Wherein:
Ar₁ is hydrogen or a $C_{6-10}$ monovalent aromatic group, wherein the $C_{6-10}$ monovalent aromatic group is unsubstituted or substituted with phenyl or naphthyl,
Ar₂ is hydrogen or a $C_{6-10}$ monovalent aromatic group, wherein the $C_{6-10}$ monovalent aromatic group is unsubstituted or substituted with phenyl or naphthyl,
Ar₃ is hydrogen; phenyl; or naphthyl,
Ar₄ is naphthylene; phenylene; pyrenylene; phenanthrylene; or anthracenylene unsubstituted or substituted with phenyl, and
Ar₅ is naphthyl; biphenyl; phenyl unsubstituted or substituted with naphthyl; or anthracenyl unsubstituted or substituted with naphthyl, phenyl, naphthyl-substituted phenyl, or biphenyl,
with the proviso that when Ar₃ is phenyl or naphthyl, Ar₁ and Ar₂ are each hydrogen, when Ar₃ is hydrogen, Ar₁ and Ar₂ are each a C6-10 monovalent aromatic group, and when Ar₄ is naphthylene or phenylene, Ar₅ is anthracenyl unsubstituted or substituted with naphthyl, phenyl, naphthyl-substituted phenyl, or biphenyl.

2. The compound of claim 1, wherein
Ar₁ and Ar₂ are each hydrogen,
Ar₃ is naphthyl,
Ar₄ is naphthylene or anthracenylene, and
Ar₅ is naphthyl; phenyl; or anthracenyl substituted with naphthyl or phenyl,
with the proviso that when Ar₄ is naphthylene, Ar₅ is anthracenyl substituted with naphthyl or phenyl.

3. The compound of claim 1, wherein
Ar₁ and Ar₂ are each hydrogen,
Ar₃ is phenyl,
Ar₄ is phenylene, and
Ar₅ is anthracenyl substituted with biphenyl.

4. The compound of claim 1, wherein
Ar₁ and Ar₂ are each hydrogen,
Ar₃ is phenyl,
Ar₄ is pyrenyl; or phenanthrylene, and Ar$_5$ is naphthyl; biphenyl; or phenyl unsubstituted or substituted with naphthyl.

5. The compound of claim 1, wherein
Ar$_1$ and Ar$_2$ are each hydrogen,
Ar$_3$ is phenyl or naphthyl,
Ar$_4$ is anthracenylene unsubstituted or substituted with phenyl; and
Ar$_5$ is naphthyl; biphenyl; or phenyl unsubstituted or substituted with naphthyl.

6. The compound of claim 1, wherein
Ar$_1$ and Ar$_2$ are each hydrogen, and
Ar$_3$ is phenyl; 1-naphthyl or 2-naphthyl.

7. The compound of claim 1, wherein
Ar$_1$ is phenyl; or naphthyl unsubstituted or substituted with phenyl or naphthyl,
Ar$_2$ is phenyl; or naphthyl unsubstituted or substituted with phenyl or naphthyl,
Ar$_3$ is hydrogen,
Ar$_4$ is naphthylene; phenylene; pyrenylene; phenanthrylene; or anthracenylene unsubstituted or substituted with phenyl, and
Ar$_5$ is naphthyl; biphenyl; phenyl unsubstituted or substituted with naphthyl; or anthracenyl unsubstituted or substituted with naphthyl, phenyl, naphthyl-substituted phenyl, or biphenyl,
with the proviso that when Ar$_4$ is naphthylene or phenylene, Ar$_5$ is anthracenyl unsubstituted or substituted with naphthyl, phenyl, naphthyl-substituted phenyl, or biphenyl.

8. The compound of claim 1, wherein
Ar$_1$ is naphthyl unsubstituted or substituted with phenyl or naphthyl,
Ar$_2$ is naphthyl unsubstituted or substituted with phenyl or naphthyl,
Ar$_3$ is hydrogen,
Ar$_4$ is naphthylene or anthracenylene, and
Ar$_5$ is naphthyl; phenyl; or anthracenyl substituted with naphthyl or phenyl,
with the proviso that when Ar$_4$ is naphthylene, Ar$_5$ is anthracenyl substituted with naphthyl or phenyl.

9. The compound of claim 1, wherein
Ar$_1$ is phenyl,
Ar$_2$ is phenyl,
Ar$_3$ is hydrogen,
Ar$_4$ is phenylene, and
Ar$_5$ is anthracenyl substituted with biphenyl.

10. The compound of claim 1, wherein
Ar$_1$ is phenyl,
Ar$_2$ is phenyl,
Ar$_3$ is hydrogen,
Ar$_4$ is pyrenyl or phenanthrylene, and
Ar$_5$ is naphthyl; biphenyl; or phenyl unsubstituted or substituted with naphthyl.

11. The compound of claim 1, wherein
Ar$_1$ is phenyl or naphthyl,
Ar$_2$ is phenyl or naphthyl,
Ar$_3$ is hydrogen,
Ar$_4$ is anthracenylene unsubstituted or substituted with phenyl, and
Ar$_5$ is naphthyl; biphenyl; or phenyl unsubstituted or substituted with naphthyl.

12. The compound of claim 1, wherein
Ar$_1$ and Ar$_2$ are each phenyl; 1-naphthyl; 2-naphthyl; 6-phenyl-2-naphthyl; or 6-(1-naphthyl)-2-naphthyl, and
Ar$_3$ is hydrogen.

13. The compound of claim 1, wherein
Ar$_1$ and Ar$_2$ are phenyl, and
Ar$_3$ is hydrogen.

14. The compound of claim 1, wherein
Ar$_4$ is 1,4-naphthylene; 2,6-naphthylene; 1,4-penylene; 1,6-pyrenylene; 2,7-phenanthrylene; 9,10-anthracenylene; or 9-phenyl-2,10-anthracenylene.

15. The compound of claim 1, wherein
Ar$_5$ is 1-naphthyl; 2-naphthyl; biphenyl-4-yl; phenyl; 4-(1-naphthyl)-phenyl; 4-(2-naphthyl)-phenyl; 10-(1-naphthyl)-9-anthracenyl; 10-(2-naphthyl)-9-anthracenyl; 10-phenyl-9-anthracenyl; 10-(4-(1-naphthyl)phenyl)-9-anthracenyl; 10-(4-(2-naphthyl)phenyl)-9-anthracenyl; or 10-(biphenyl-4-yl)-9-anthracenyl.

16. The compound of claim 1, wherein the compound of formula 1 is selected from the group consisting of the following compounds:

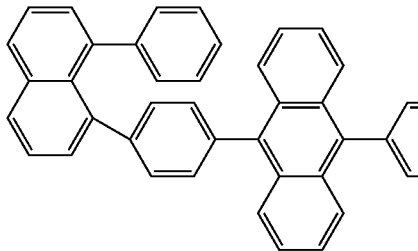
,
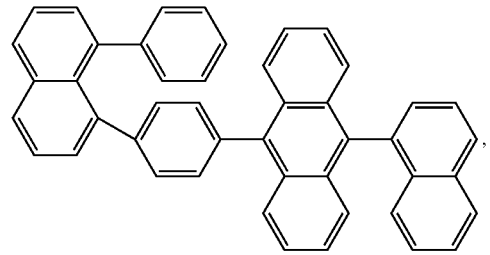
,
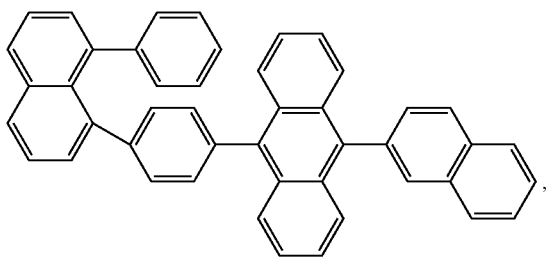
,
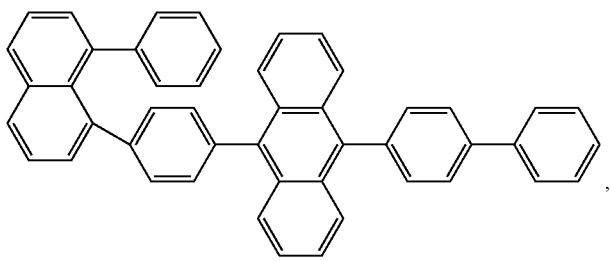
,

-continued
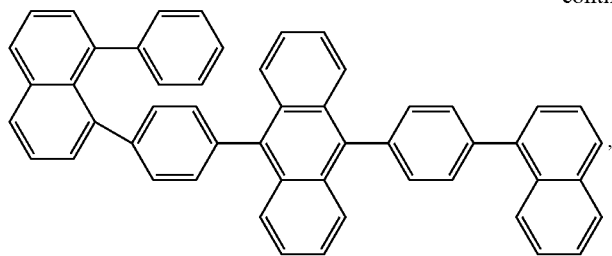

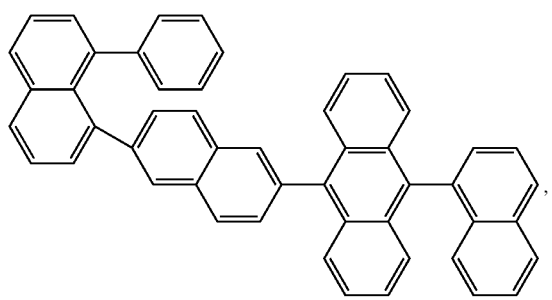
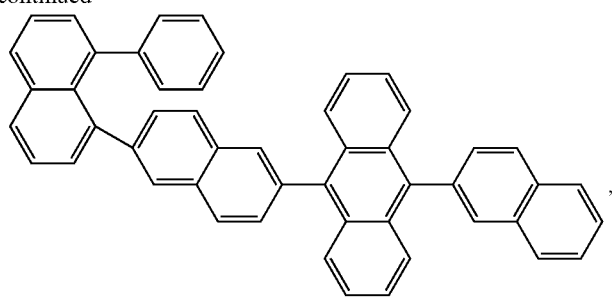
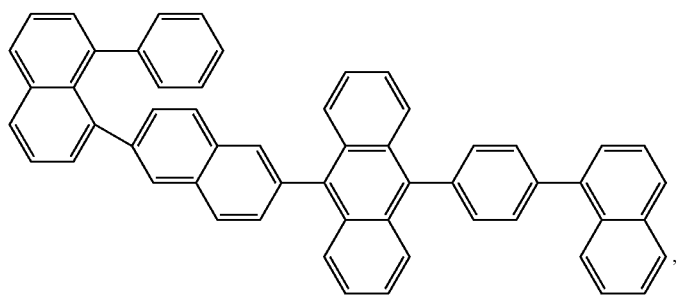
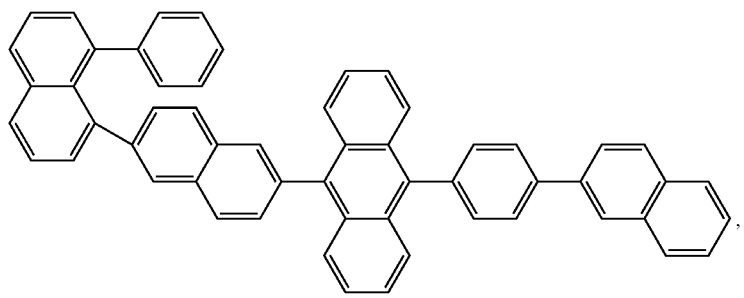
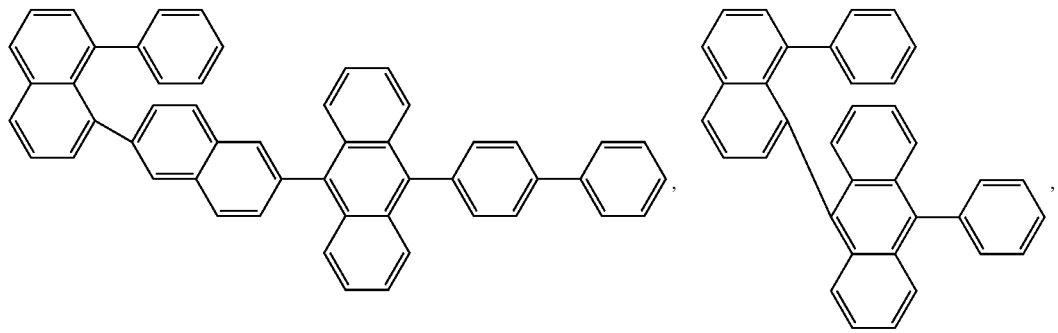
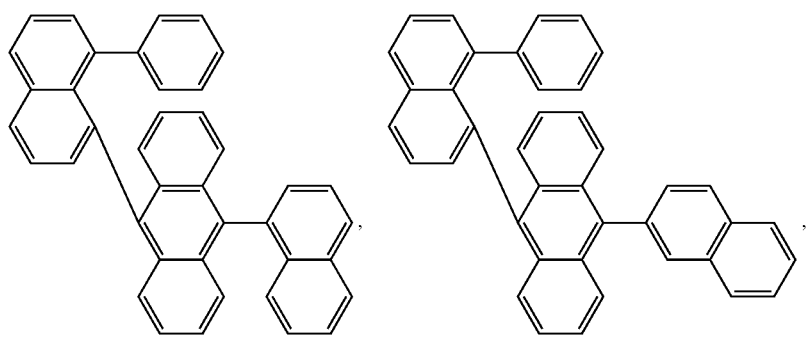

-continued
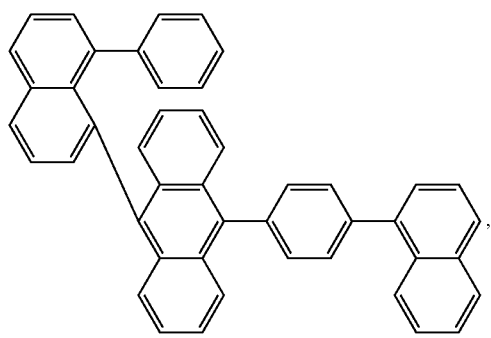
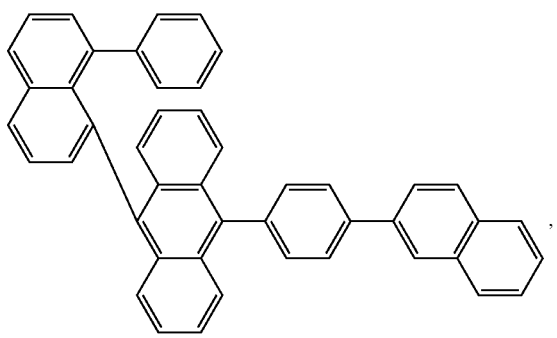
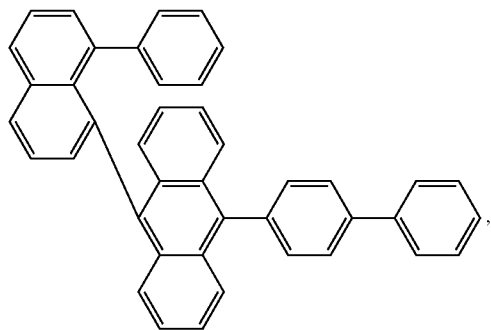
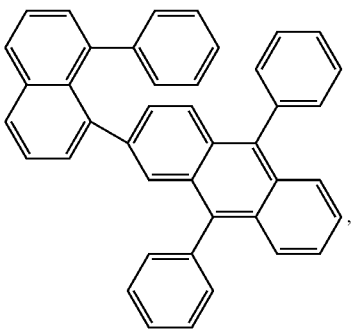
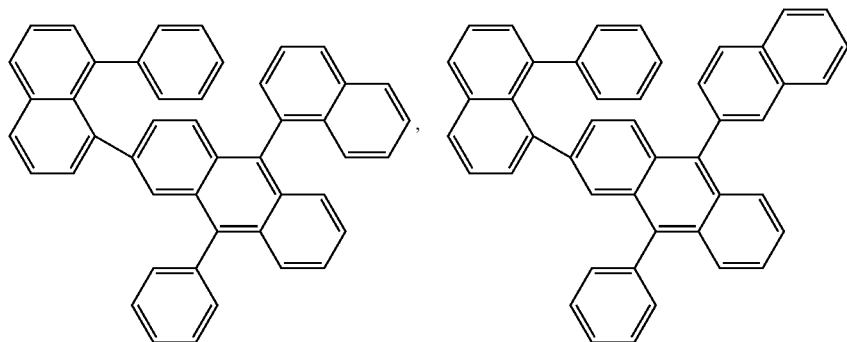
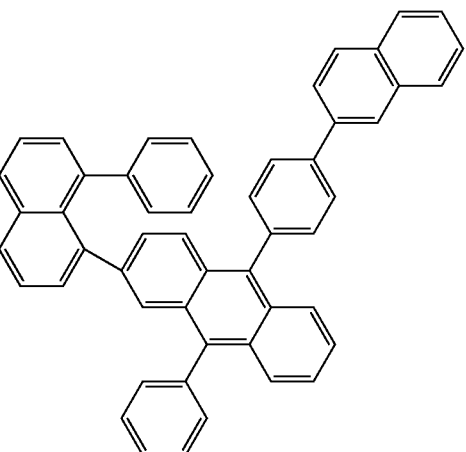

-continued
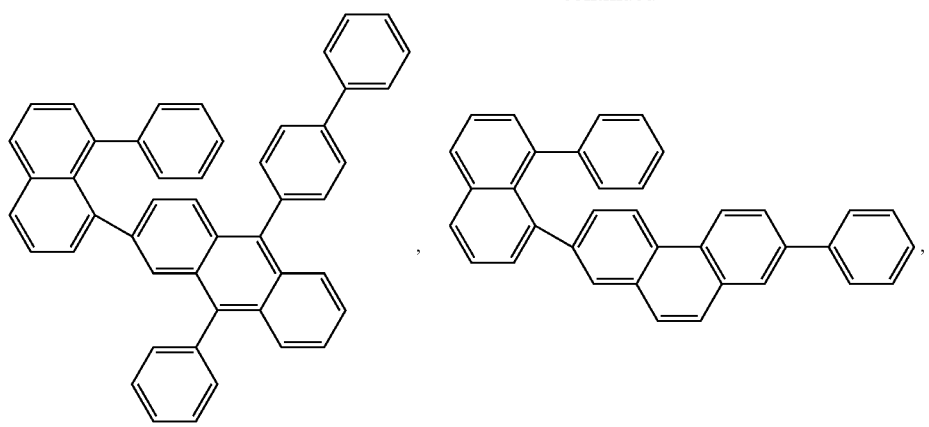
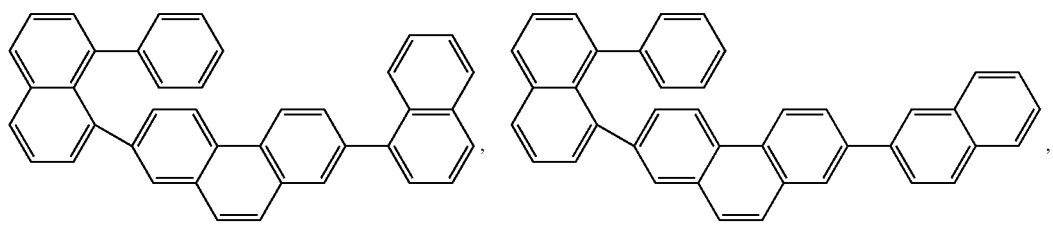
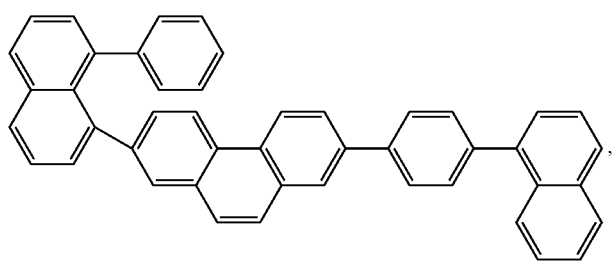
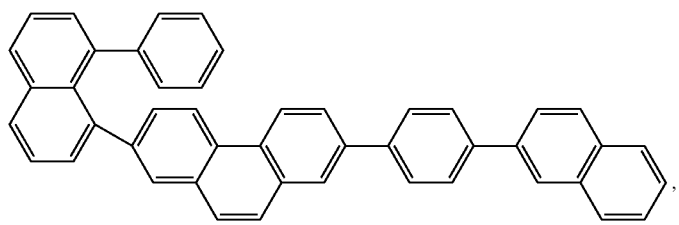
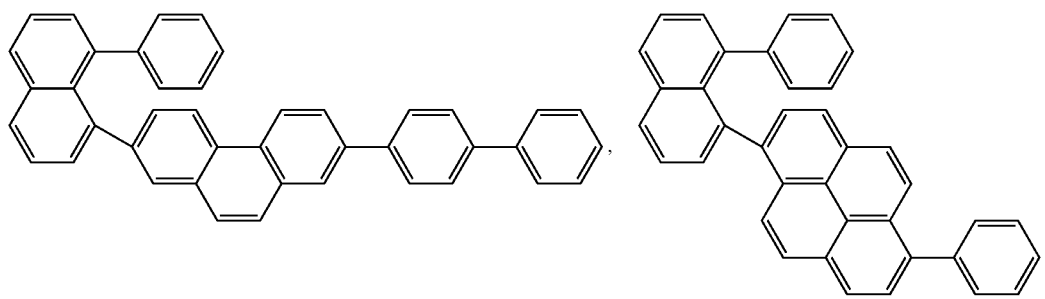

-continued
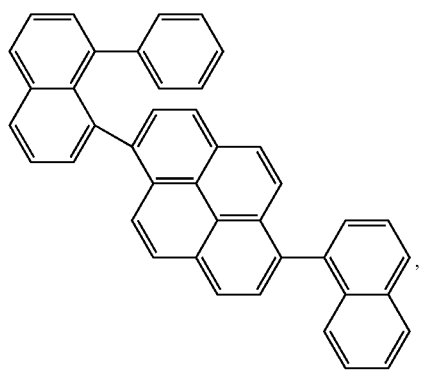
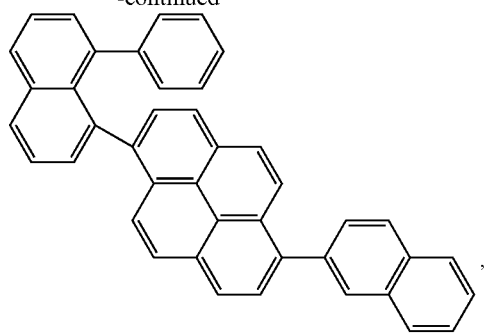
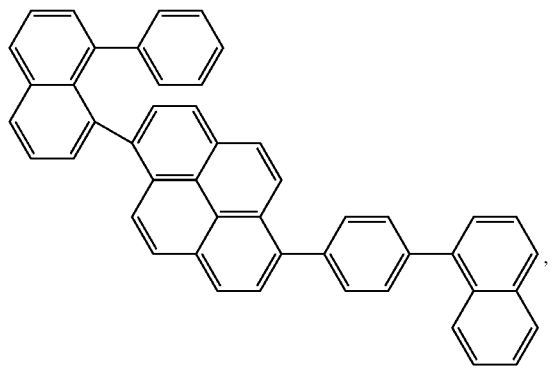
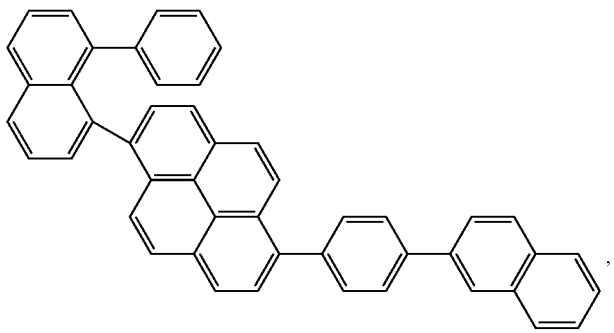
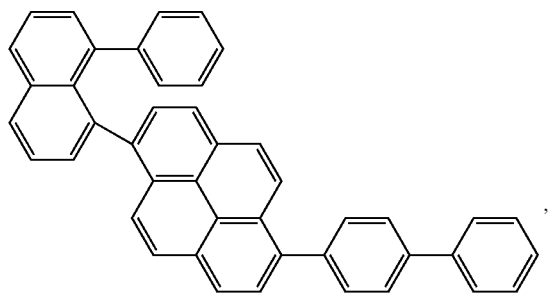
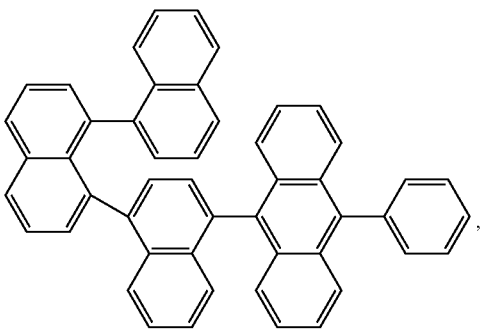
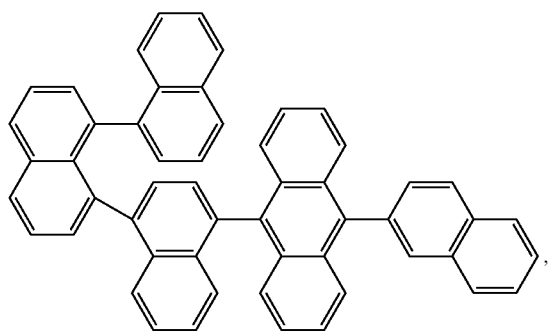
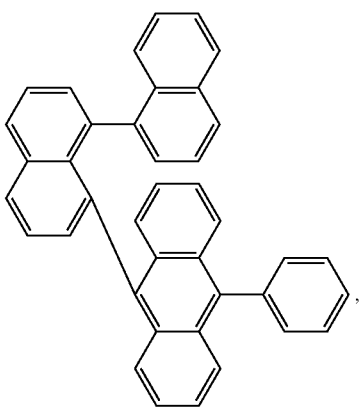

-continued
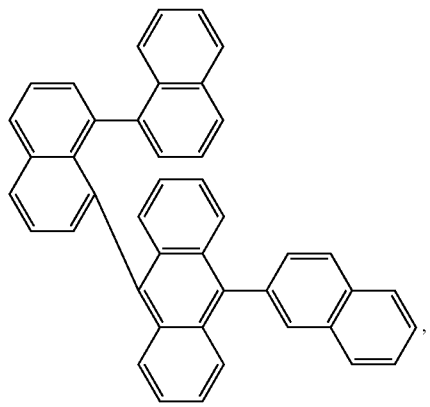
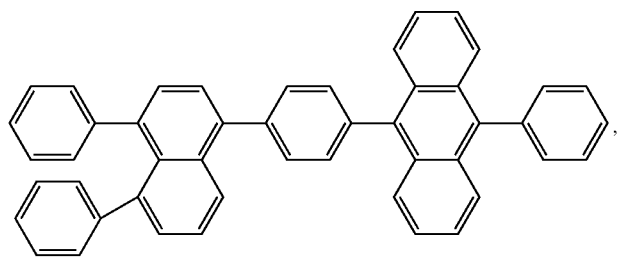
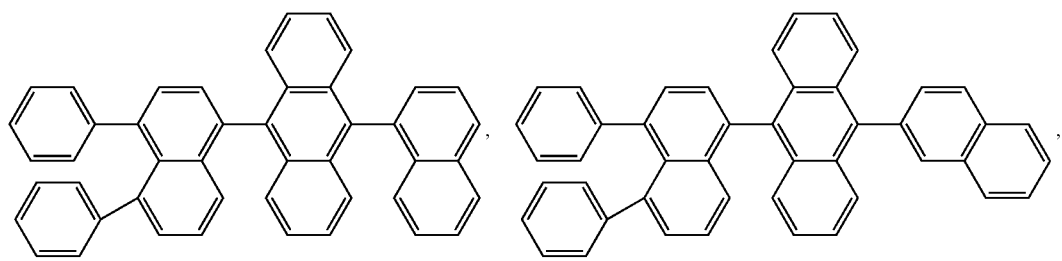
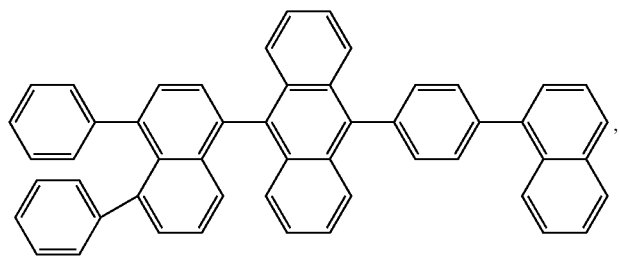
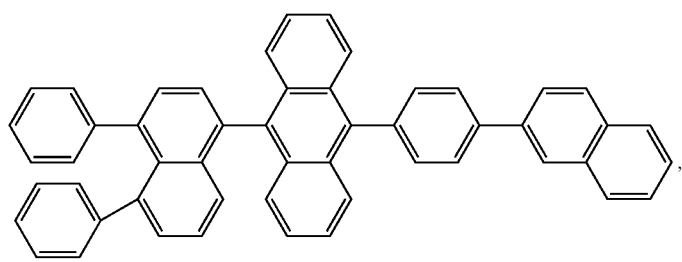
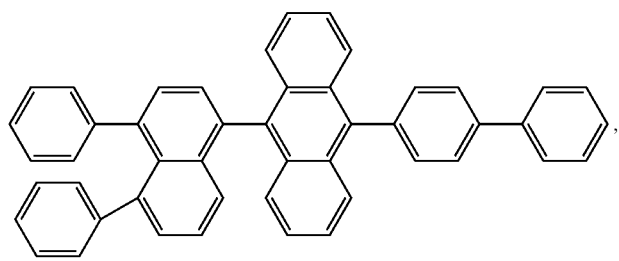

-continued
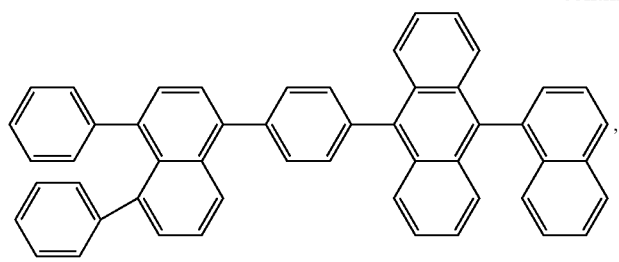
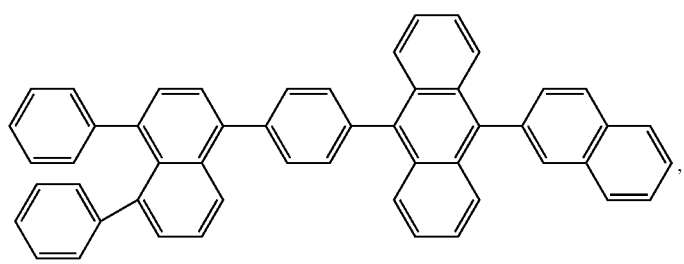
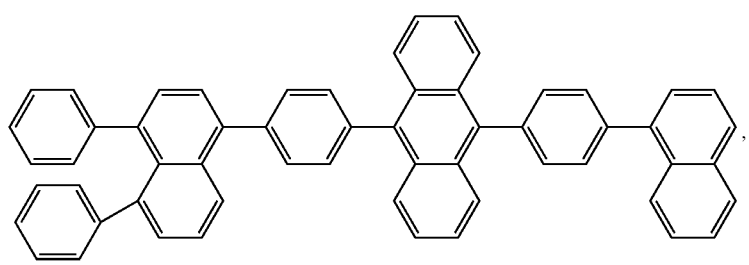
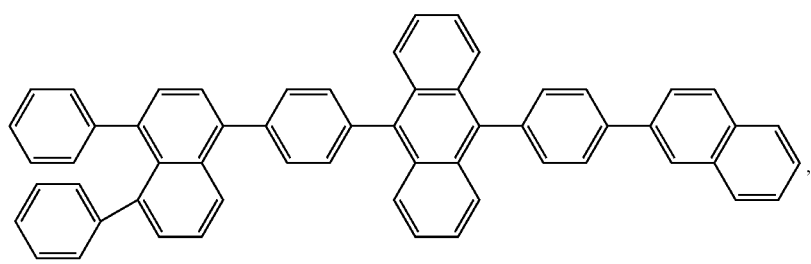
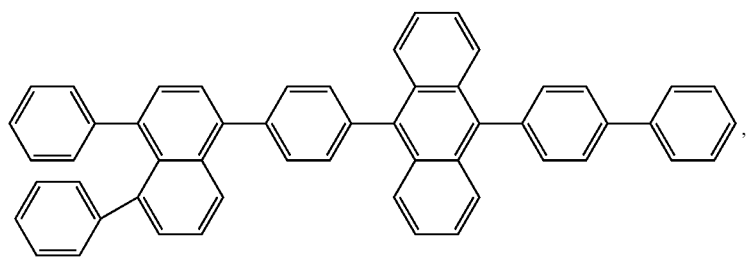
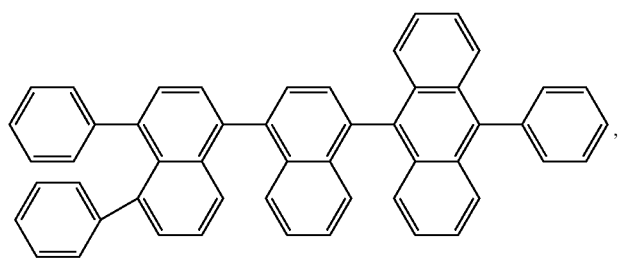

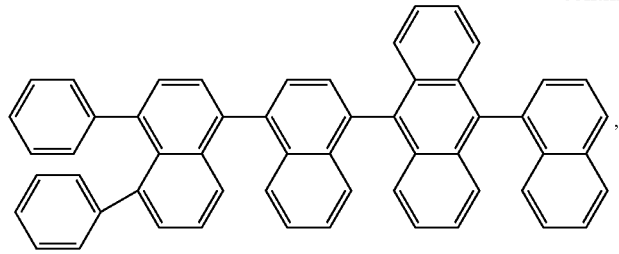,
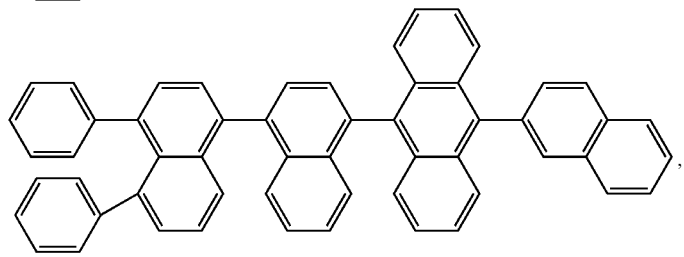,
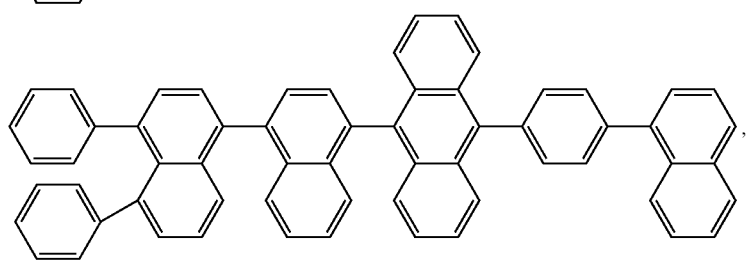,
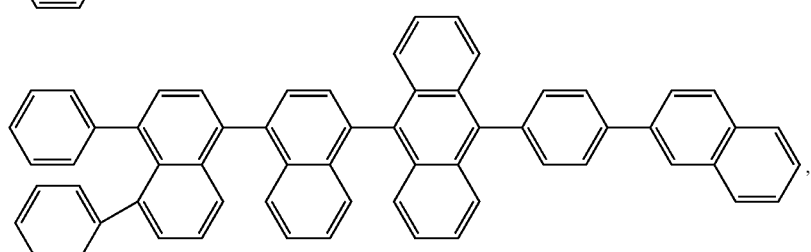,
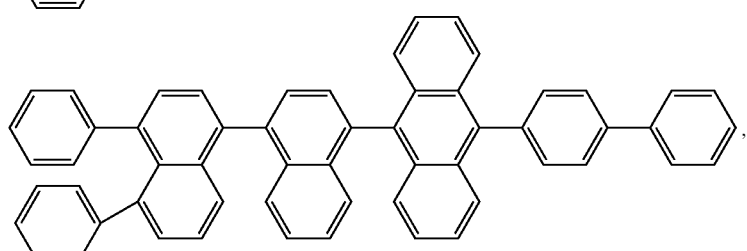,
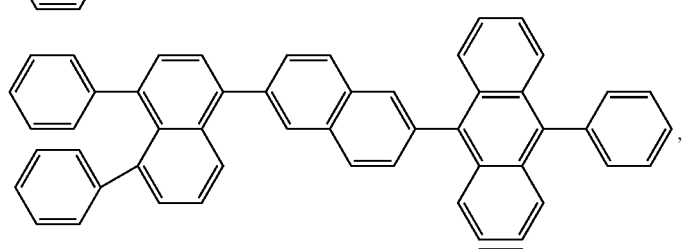,
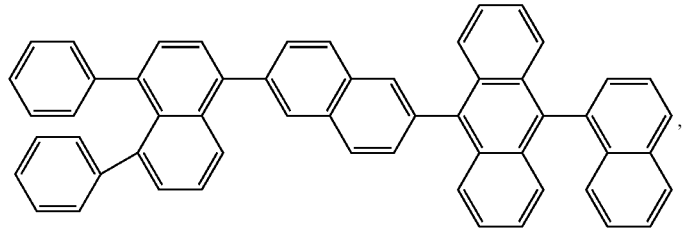, -continued
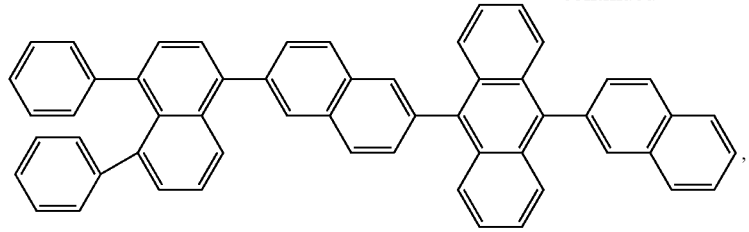
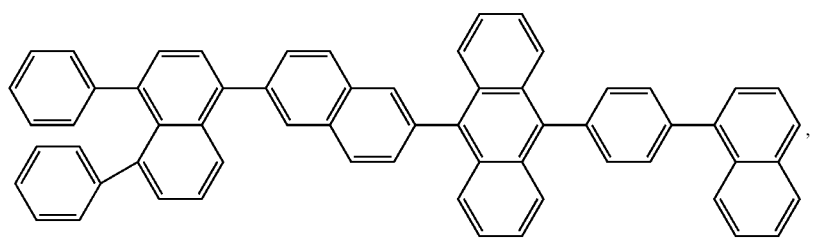
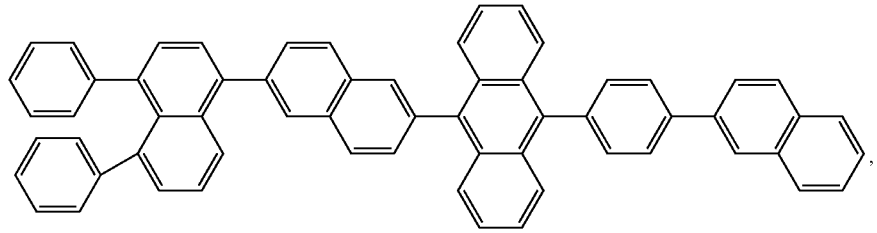
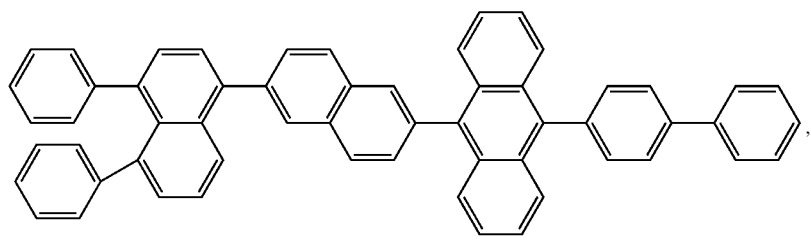
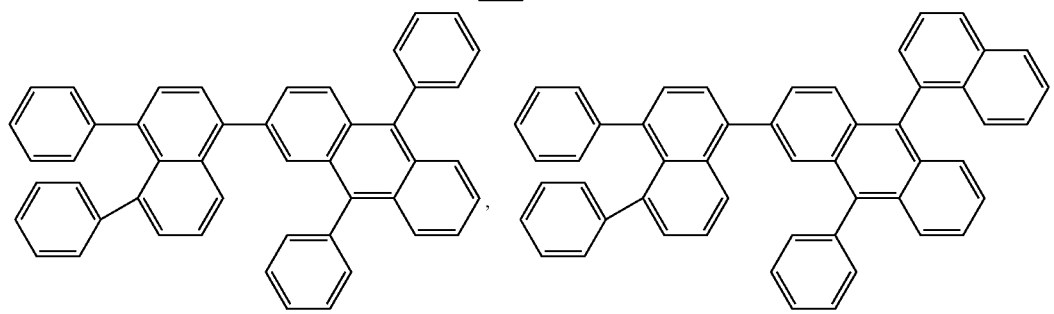
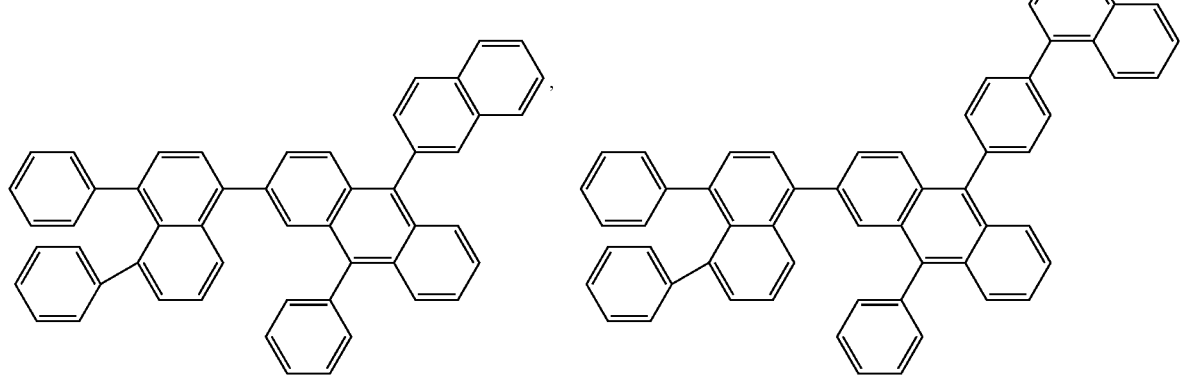

-continued
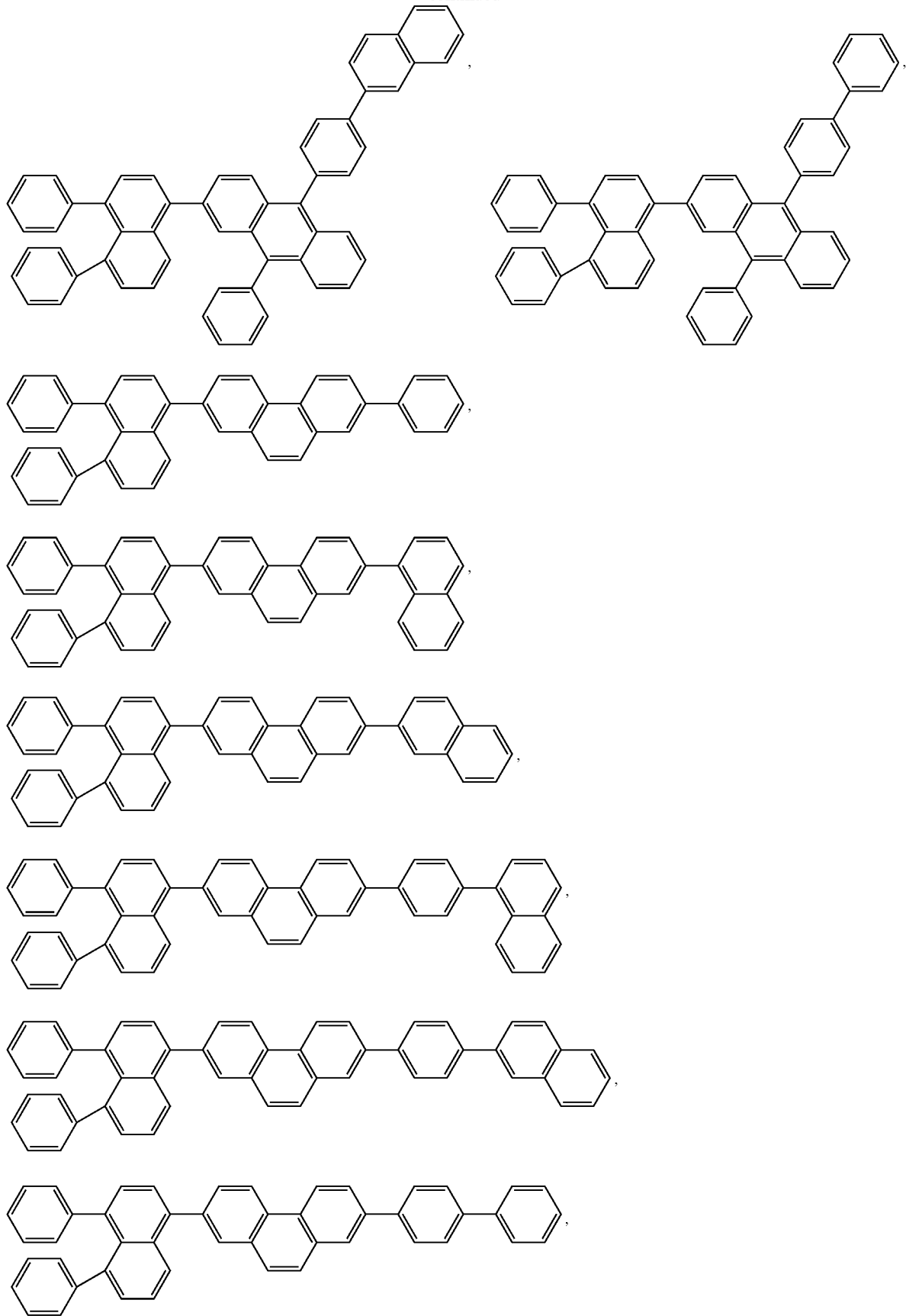

115
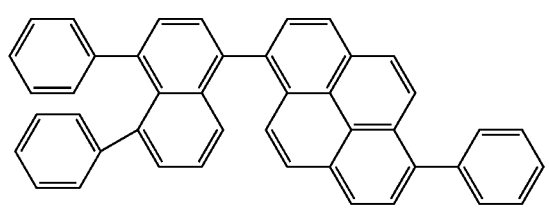
116
-continued
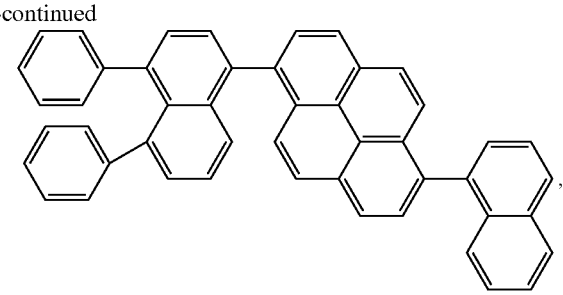
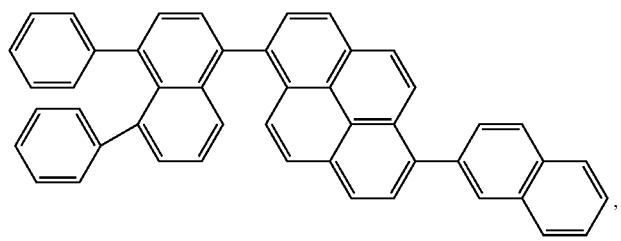
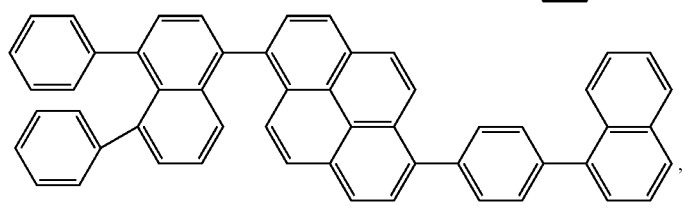
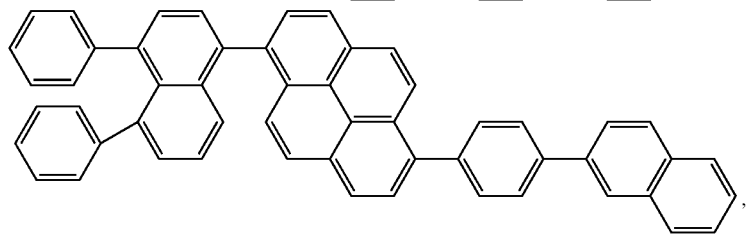
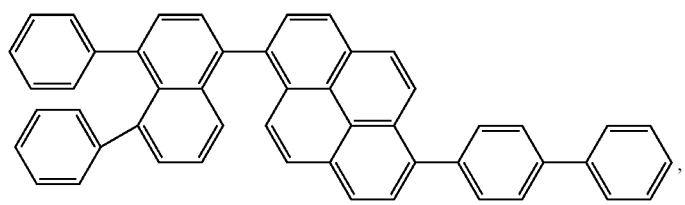
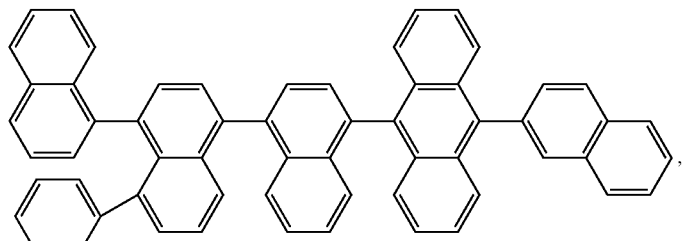
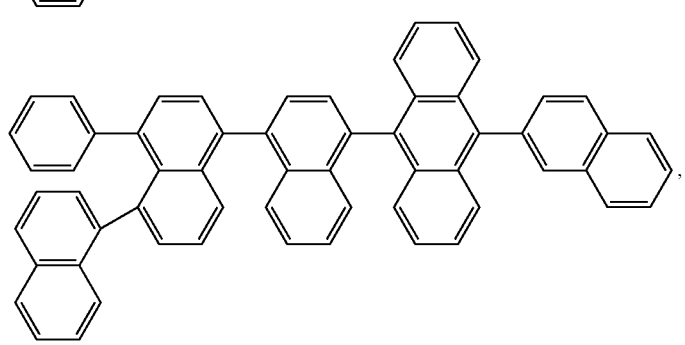

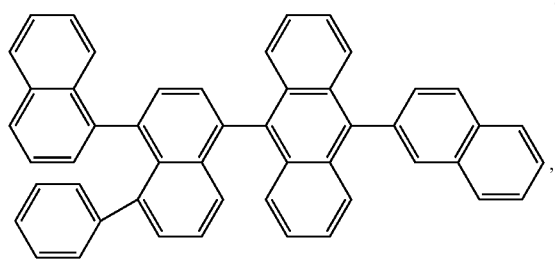 , and 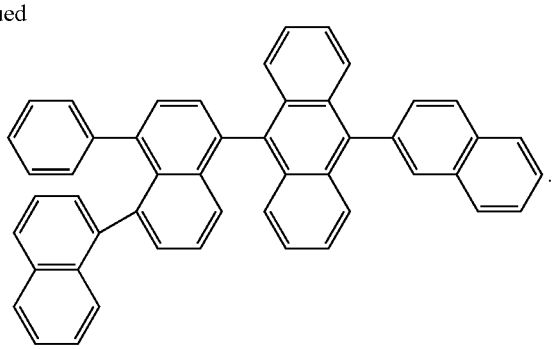 .

17. A material for an organic electroluminescent device, which comprises the compound of claim 1.

18. An organic electroluminescent device which comprises one or more organic thin film layers including at least one light-emitting layer and sandwiched between a cathode and an anode,
wherein at least one of the organic thin film layers contains the material of claim 17.

* * * * *